(12) United States Patent
Kaulich et al.

(10) Patent No.: US 12,286,624 B2
(45) Date of Patent: Apr. 29, 2025

(54) METHOD FOR GENERATING A GENE EDITING VECTOR WITH FIXED GUIDE RNA PAIRS

(71) Applicant: Johann Wolfgang Goethe-Universität Frankfurt am Main, Frankfurt am Main (DE)

(72) Inventors: Manuel Kaulich, Frankfurt am Main (DE); Ivan Dikic, Frankfurt am Main (DE); Martin Wegner, Bad Nauheim (DE); Yves Matthess, Fulda (DE); Koraljka Husnjak, Frankfurt am Main (DE)

(73) Assignee: JOHANN WOLFGANG GOETHE-UNIVERSITÄT FRANKFURT AM MAIN, Frankfurt (DE)

( * ) Notice: Subject to any disclaimer, the term of this patent is extended or adjusted under 35 U.S.C. 154(b) by 1114 days.

(21) Appl. No.: 16/973,011

(22) PCT Filed: Jun. 11, 2019

(86) PCT No.: PCT/EP2019/065167
§ 371 (c)(1),
(2) Date: Dec. 7, 2020

(87) PCT Pub. No.: WO2019/234258
PCT Pub. Date: Dec. 12, 2019

(65) Prior Publication Data
US 2021/0261954 A1 Aug. 26, 2021

(30) Foreign Application Priority Data
Jun. 8, 2018 (EP) .................................... 18176677

(51) Int. Cl.
C12N 15/11 (2006.01)
(52) U.S. Cl.
CPC .......... *C12N 15/11* (2013.01); *C12N 2310/20* (2017.05); *C12N 2330/51* (2013.01)
(58) Field of Classification Search
CPC . C12N 15/11; C12N 2310/20; C12N 2330/51
See application file for complete search history.

(56) References Cited

U.S. PATENT DOCUMENTS

2014/0363850 A1* 12/2014 Salerno ................ C12Q 1/6844
435/194

FOREIGN PATENT DOCUMENTS

| WO | WO 2014/039684 | 3/2014 | |
|----|----|----|----|
| WO | WO 2014/093595 | 6/2014 | |
| WO | WO 2014/093701 | 6/2014 | |
| WO | WO-2014093701 A1 * | 6/2014 | ........... C12N 15/01 |
| WO | WO 2014/204724 | 12/2014 | |
| WO | WO 2015/040075 | 3/2015 | |
| WO | WO 2015/065964 | 5/2015 | |
| WO | WO-2016025131 A1 * | 2/2016 | ........... C12N 15/102 |
| WO | WO 2016/106236 | 6/2016 | |
| WO | WO 2017/005807 | 1/2017 | |
| WO | WO 2017/040511 | 3/2017 | |
| WO | WO 2017/049129 | 3/2017 | |
| WO | WO 2017/132112 | 8/2017 | |
| WO | WO 2017/155714 | 9/2017 | |
| WO | WO 2018/122248 | 7/2018 | |

OTHER PUBLICATIONS

Sakuma et al. ("Multiplex genome engineering in human cells using all-in-one CRISPR/Cas9 vector system." Scientific reports 4.1 (2014): 1-6) (Year: 2014).*
Koferle et al. ("CORALINA: a universal method for the generation of gRNA libraries for CRISPR-based screening." BMC genomics 17.1 (2016): 1-13 ) (Year: 2016).*
Barlett et al. "Recombination between directly repeated origins of conjugative transfer cloned in M13 bacteriophage DNA models ligation of the transferred plasmid strand." *Nucleic acids research* (1990) 18.12: 3579-3586.
Chen et al. "Dynamic imaging of genomic loci in living human cells by an optimized CRISPR/Cas system." *Cell* (2013) 155.7: 1479-1491.
Cong et al. "Multiplex genome engineering using CRISPR/Cas systems." *Science* (2013) 339.6121: 819-823.
Han et al. "Synergistic drug combinations for cancer identified in a CRISPR screen for pairwise genetic interactions." *Nature biotechnology* (2017) 35.5: 463-474.
Hou et al. "Efficient genome engineering in human pluripotent stem cells using Cas9 from Neisseria meningitidis." *Proceedings of the National Academy of Sciences* (2013) 110.39: 15644-15649.
Kim et al. "In vivo high-throughput profiling of CRISPR-Cpf1 activity." *Nature methods* (2017) 14.2: 153-159.
Kleinstiver et al. "Genome-wide specificities of CRISPR-Cas Cpf1 nucleases in human cells." *Nature biotechnology* (2016) 34.8: 869-874.
Konermann et al. "Genome-scale transcriptional activation by an engineered CRISPR-Cas9 complex." *Nature* (2015) 517.7536: 583-588.
Kuate et al. "Analysis of partial recombinants in lentiviral vector preparations." *Human gene therapy methods* (2014) 25.2: 126-135.
Lorenz et al. "ViennaRNA Package 2.0." *Algorithms for molecular biology* (2011) 6.1: 1-14.

(Continued)

*Primary Examiner* — Sahana S Kaup
(74) *Attorney, Agent, or Firm* — Morrison & Foerster LLP

(57) ABSTRACT

The present invention pertains to a novel method for the generation of a vector construct suitable for gene editing applications which comprises a fixed pair of predetermined expressible guide RNA (gRNA) sequences. The method of the invention allows for an easy construction of such vectors and provides in addition thereto vector libraries for the expression of fixed pairs of gRNAs. The vectors of the invention may be advantageously used to cut out larger genomic DNA sequences, or alternatively, to simultaneously introduce mutations in the genome without a loss or larger genomic sequences. Hence, the system of the invention provides for many molecular genetic approaches for genome alteration.

10 Claims, 35 Drawing Sheets

Figure 1:
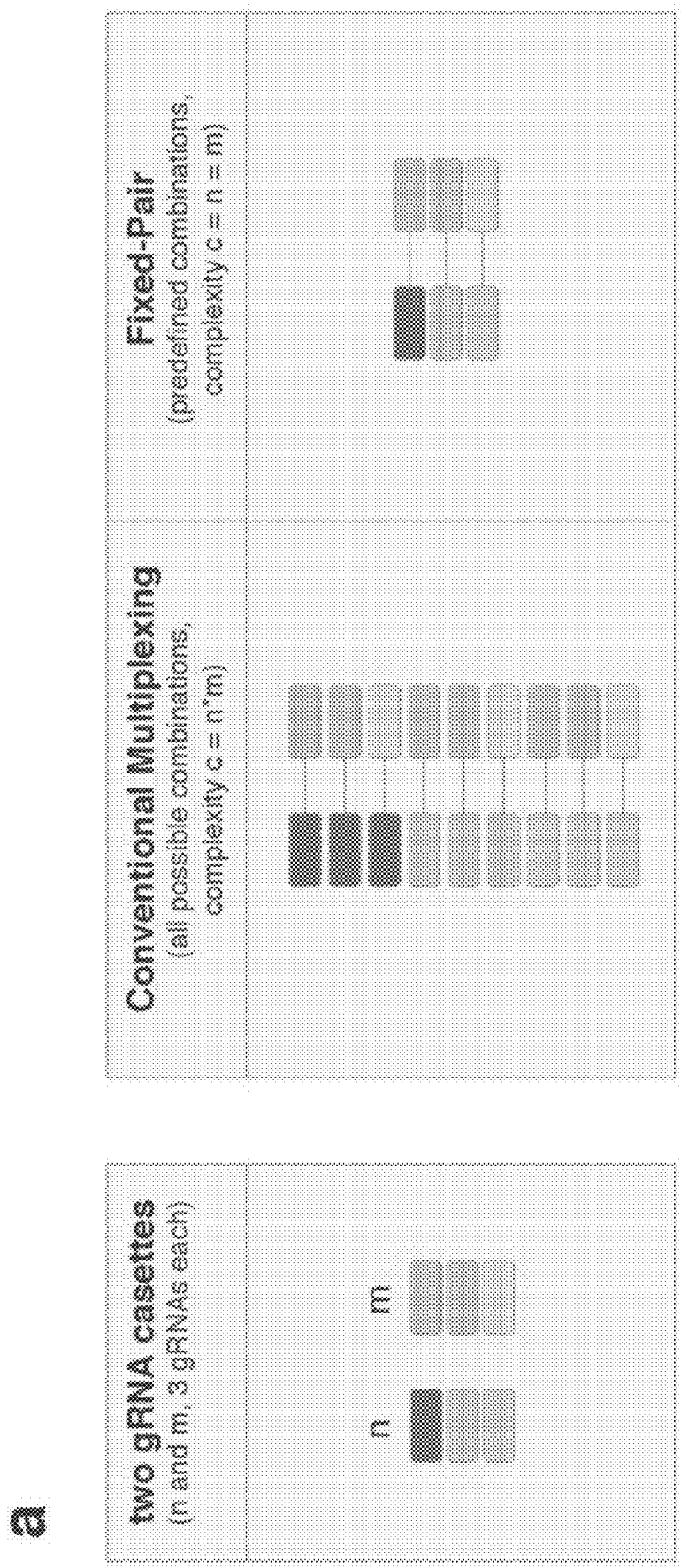
Figure 1:
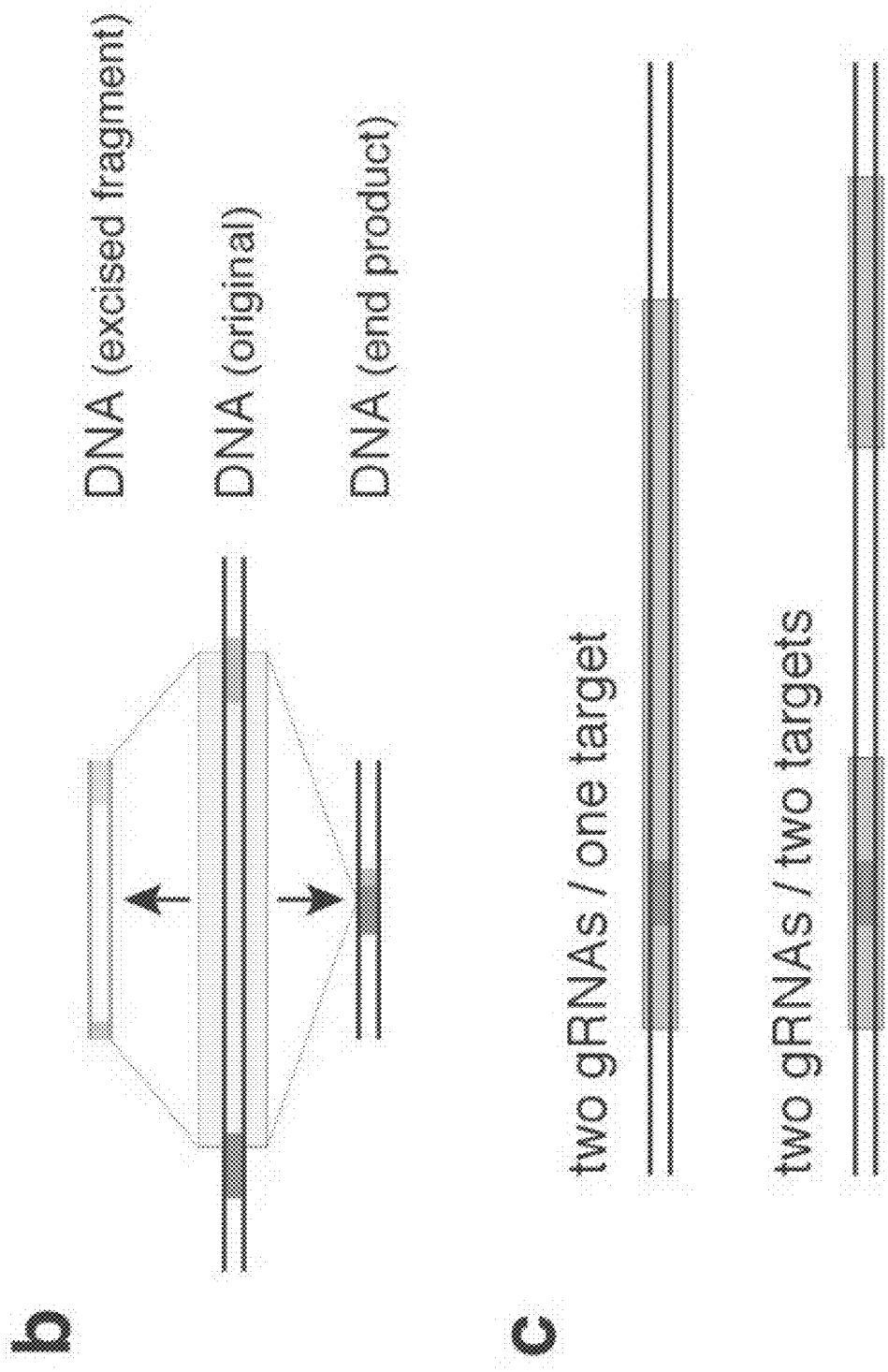
Figure 1:
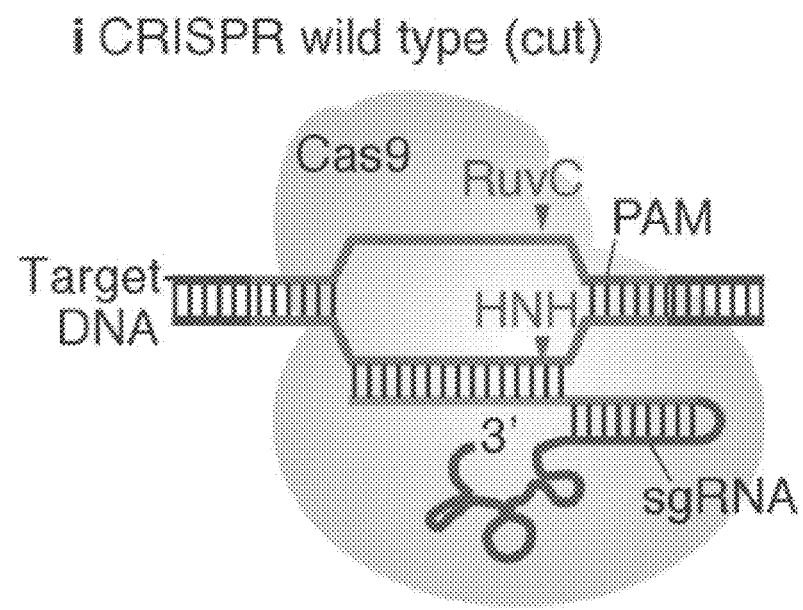
Figure 1:
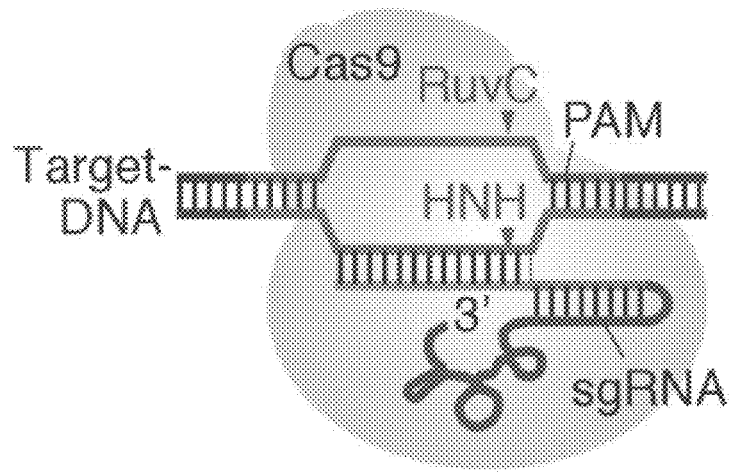
Figure 1:
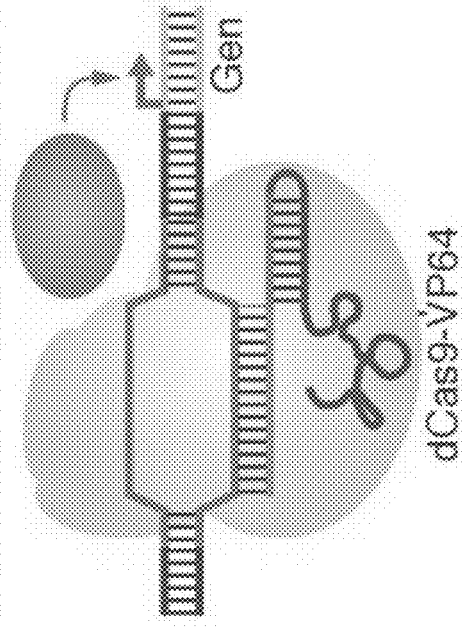
Figure 1:
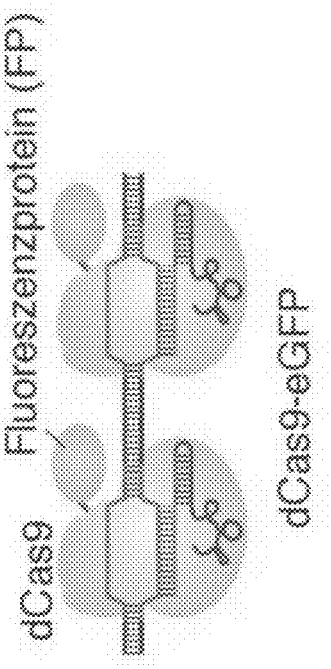
Figure 1:
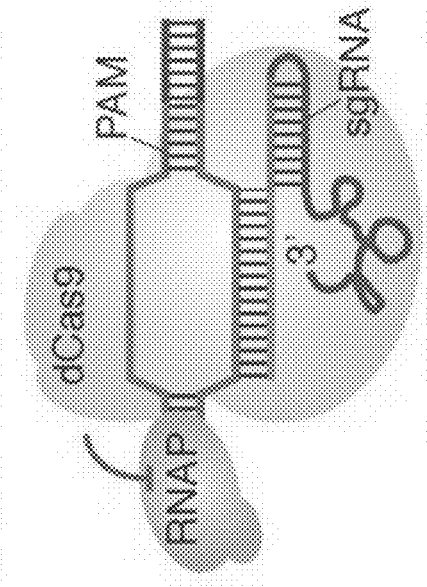
Figure 1:
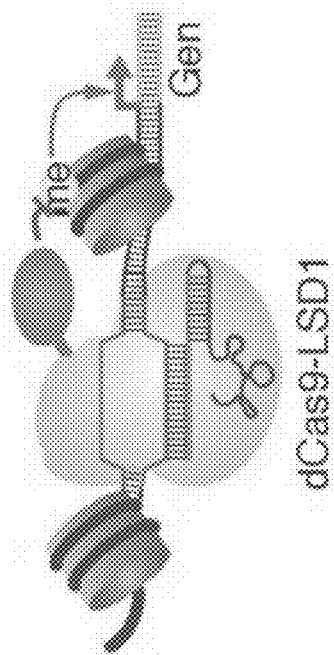

Specification includes a Sequence Listing.

(56) References Cited

OTHER PUBLICATIONS

Mali et al. "RNA-guided human genome engineering via Cas9." *Science* (2013) 339.6121: 823-826.

Miller et al. "Redesign of retrovirus packaging cell lines to avoid recombination leading to helper virus production." *Molecular and Cellular Biology* (1986) 6.8: 2895-2902.

Ran et al. "In vivo genome editing using *Staphylococcus aureus* Cas9." *Nature* (2015) 520.7546: 186-191.

Sack et al. "Sources of error in mammalian genetic screens." *G3: Genes, Genomes, Genetics* (2016) 6.9: 2781-2790.

Tzelepis et al. "A CRISPR dropout screen identifies genetic vulnerabilities and therapeutic targets in acute myeloid leukemia." *Cell reports* (2016) 17.4: 1193-1205.

Alonso-Padilla et al., "Development of Novel Adenoviral Vectors to Overcome Challenges Observed With HAdV-5-based Constructs," Mol Ther (2016) 24(1):6-16.

Chylinski et al., "The tracrRNA and Cas9 families of type II CRISPR-Cas immunity Systems," RNA Biology (2013) 10(5):762-737.

Heintze et al., "A CRtSPR CASe for high-throughput silencing," Frontier Genetics (2013) 4(193): doi: 10.3389/fgene.2013.00193.

Horwitz et al., "Efficient Multiplexed Integration of Synergistic Alleles and Metabolie Pathways in Yeasts via CRISPR-Cas," Cell Systems (2015) 1:88-96.

International Search Report and Written Opinion for PCT/EP2019/065167, dated Sep. 9, 2019, 24 pages.

Karvelis et al., "crRNA and tracrRNA guide Cas9-mediated DNA interference in *Streptococcus thermophiles*," RNA Biology (2013)10(5):841-851.

Koferle et al., "CORALINA: a universal method for the generation of gRNA libraries for CRISPR-based screening," BMC Genomics (2016) 17:917.

Schiwon et al., "One-Vector System for Multiplexed CRISPR/Cas9 against Hepatitis B Virus cccDNA Utilizing High-Capacity Adenoviral Vectors," Mol Ther (2018) 12:242-253.

Seeger et al., "Complete Spectrum of CRISPR/Cas9-induced Mutations on HBV cccDNA," Mol Ther (2016) 24(7):1258-1266.

\* cited by examiner d i CRISPR wild type (cut)

ii CRISPR single active center (nickase)

Figure 3 cont.:

b SpCas9 tracrRNAs

WT(v1):
GTTTTAGAGCTAGAAATAGCAAGTTAAAATAAGGCTAGTCCGTTATCAACTTGAAAAAGTGGCACCGAGTCGGTGC

V2:
GTTTAAGAGCTATGctggaaacagcatAGCAAGTTTAAATAAGGCTAGTCCGTTATCAACTTGAAAAAGTGGCACCGAGTCGGTGC our(V3):
GTTTTAGAGCTAGAgagctcCTAGCCAAGTTAAAATAAGGCTAGTCCGaatagAACTTCCACAAGTGGCAggcAgtgccTGC Spv1.Spv2

Spv2.Spv3

Spv2.Sa

Spv2.Nm

Spv2.AsCpf1 a b b c

METHOD FOR GENERATING A GENE EDITING VECTOR WITH FIXED GUIDE RNA PAIRS

CROSS REFERENCE TO RELATED APPLICATIONS

This application is a national stage application under 35 U.S.C. § 371 of International Application No. PCT/EP2019/065167, filed internationally on Jun. 11, 2019, which claims the benefit of priority to European Application No. 18176677.5, filed Jun. 8, 2018, the contents of which are hereby incorporated by reference in their entirety for all purposes.

SUBMISSION OF SEQUENCE LISTING ON ASCII TEXT FILE

The present application is being filed along with a Sequence Listing in electronic format. The Sequence Listing is provided as a file entitled 595282002900SeqList.txt, created Dec. 7, 2020, which is 4,876 bytes in size. The information in the electronic format of the Sequence Listing is incorporated by reference in its entirety.

FIELD OF THE INVENTION

The present invention pertains to a novel method for the generation of a vector construct suitable for gene editing applications which comprises a fixed pair of predetermined expressible guide RNA (gRNA) sequences. The method of the invention allows for an easy construction of such vectors and provides in addition thereto vector libraries for the expression of fixed pairs of gRNAs. The vectors of the invention may be advantageously used to cut out larger genomic DNA sequences, or alternatively, to simultaneously introduce mutations in the genome without a loss or larger genomic sequences. Hence, the system of the invention provides for many molecular genetic approaches for genome alteration.

DESCRIPTION

The clustered regularly interspaced short palindromic repeats (CRISPR)/Cas system was initially discovered in bacterial and archaeal species as a defense mechanism against foreign genetic material (e.g. plasmids and bacteriophages). The naturally occurring CRISPR/Cas systems rely on expression of three components: 1) a guide RNA sequence that is complementary to a target sequence, 2) a scaffold RNA that aids in recruiting the third component, an endonuclease, to the site. Though in many bacterial and archaeal species CRISPR/Cas systems are used to degrade foreign genetic material, the system has been adapted for use in a wide variety of prokaryotic and eukaryotic organisms and has been used for many methods including gene knockout, mutagenesis, and expression activation or repression (Hsu, et al. Cell (2014) 157(6): 1262-1278). In genetically engineered CRISPR/Cas systems, the requirement for three independent components can be circumvented by expression of a small guide RNA (sgRNA, or simply guide RNA-gRNA) that contains both the CRISPR guide RNA sequence for binding a target sequence and the scaffold RNA that together mimics the structure formed by the individual guide RNA sequence and scaffold sequence and is sufficient to recruit the endonuclease to the appropriate target site (Jinek, et al. Science (2012) 337(6096):816-821). An additional prerequisite for successful DNA targeting of the Cas-gRNA complex is the presence of a protospacer-adjacent motif (PAM) DNA sequence in the target DNA, for which the exact sequence depends on the bacterial Cas-enzyme. For the most widely used *Streptococcus pyogenes* Cas9 (Sp-Cas9) this sequence has the format of NGG, where N can be any nucleotide. Most notably, the Cas enzyme can be expressed in human cells and, by providing a human DNA-directed gRNA, induce a highly specific DNA double strand break that cannot be repaired, leading to insertion and deletion (InDel) mutations. Phenotypes of InDel mutations range from in-frame deletions to complete gene knockouts. Recently, the CRISPR/Cas system has been demonstrated to efficiently correct a mutation responsible for sickle cell disease by using patient-derived stem and progenitor cells. Hence, the CRISPR/Cas system is a programmable gene-editing tool with enormous potential, ranging from standard cell biology to therapeutic applications.

Single genetic changes can be used to generate well-controlled model systems, but these do not allow for unbiased screenings. To perform genetic screens, a multitude of gRNA sequences can be combined to generate libraries, targeting specific regions in the human and other genomes. Major advantages of these genetic screens are their unbiased application and ease of use. As of today, only a couple of genome-wide CRISPR/Cas knockout screens have been published, but the pace in which these experiments are performed and respective results are reported has accelerated tremendously. In addition to knockout screens, a handful of laboratories have demonstrated the benefits of genome-wide CRISPR/Cas transcriptional activation and repression screens. Areas covered by these screens include drug resistance, cellular growth, recessive and essential genes, long-non-coding RNAs (lncRNAs) as well as NF-kappaB activating/repressive genes, or metastasis inducing genes.

Conventional pooled gRNA cloning is labor intense, error prone and results in reagents with severe sequence bias and cloning artefacts[1]. Besides these technological shortcomings, the field of applied CRISPR/Cas screenings has made major steps towards the generation of single and multiplexed gRNA libraries that allow the generation of complex libraries in which each gRNA is randomly combined with all gRNAs (FIG. 1a)[2]. The complexity (c) of such a reagent is the product of n oligonucleotides targeting the first and m oligonucleotides targeting the second gRNA expressing cassette. Hence, with increasing numbers of gRNAs, the complexity of such gRNA libraries quickly becomes too large for economically feasible screening experiments[2]. Additionally, not all possible gRNA combinations in multiplexed gRNA libraries are biologically relevant. Therefore, defining the exact combination of two gRNAs on a single plasmid ("fixed-pair") is often desired (FIG. 1a). Until today there is no technological solution for the generation of pooled defined fixed-pair gene perturbation reagents.

Predetermining the combination of two, or more, gRNAs on a single plasmid is of enormous scientific relevance and multiple applications can greatly benefit from such a technology:

DNA excision: Two gRNAs can induce two synchronized DNA double stand breaks simultaneously that are located in close two- or three-dimensional proximity. Proximity can result in the excision of the DNA fragment that lies between the two gRNA target sequences (FIG. 1b). As such, coding and noncoding genetic elements can be precisely excised in order to investigate their biological function and the consequences of a loss of the respective DNA sequence.

Two (or more) gRNAs—one target: To dissect target relevance with improved confidence, fixed-pair 3Cs reagents enable directing two (or more) gRNAs to the same target, thereby improving the efficiency of the editing event (cutting, modification, etc.) (FIG. 1c).

Two (or more) gRNAs—two (or more) targets: Fixed-pair gRNAs enable the precise predetermination of target pairs (or target groups) to be analyzed, thereby enabling direct dissection of the target-to-target interactions, without the need of having all theoretically possible interactions analyzed (FIG. 1c,d,e).

CRISPR activation and inhibition: To induce or block target transcription, multiple gRNAs are required for efficient changes; therefore, multiple defined gRNAs on the same plasmid improve activation or inhibition rates while maintaining low complexity gRNA reagents.

Drug efficacy and resistance screens: Fixed pair 3Cs reagents enable the use of two (or more) gRNAs to monitor the efficacy of or dissect molecular mechanisms underlying the action of or resistance against FDA-approved or novel drugs without the need for actually applying the drugs.

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

I. Generating gRNA Vectors and Vector Libraries Using Covalently Closed Circular (ccc) DNA Recently the inventors developed a new system for the generation of higher order gRNA libraries by generating a cccDNA based small RNA or expression vector library. This method included basically the following steps of (a) Providing a single stranded (ss) phagemid vector comprising (i) at least one small RNA/DNA expression cassette comprising a RNA/DNA promoter and an empty target-small-RNA/DNA-sequence-introduction-site or a small RNA/DNA coding sequence and/or a DNA/RNA nuclease target sequence, or partial sequence thereof, (ii) at least one origin for replication (ORI) of single strand DNA such as a phage ORI, and in particular a f1-origin, and (b) Providing at least one species of mutagenic RNA or DNA-Primer, wherein the mutagenic RNA or DNA-primer has the following structure in 3' to 5' direction: a first homology region, a target sequence region encoding for a small RNA/DNA to be expressed, and a second homology region, wherein the first homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 5' side, and wherein the second homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 3' side, (c) Annealing of at least one species of mutagenic RNA or DNA-primer to the ss-phagemid vector construct and amplifying a covalently closed circularized (ccc) heteroduplex dsDNA therefrom, (d) removing residual wild type phagemid vector DNA.

The method is fully disclosed in International patent application No. PCT/EP2017/084625 which shall be included herein by reference in its entirety. The method is further described in comparative example 1. The above method may be used not only for the generation of a higher order library, but also for the creation of single or multiple (but not higher order) vector(s). Hence, the present invention may in some embodiments specifically refer to steps of the method, or materials, as disclosed in PCT/EP2017/084625, which is in the following repeated as being related to the present invention.

In context of the herein disclosed invention removing residual wild type phagemid vector DNA endonuclease digestion may be applied. For example, an endonuclease target site is provided in the single stranded (ss) phagemid vector construct within its' at least one small RNA/DNA expression cassette. Preferably the endonuclease target site is located in the single stranded (ss) phagemid vector construct between the regions which are complementary to the first homology region of the mutagenic DNA-Primer and the region complementary to the second homology region of the mutagenic primer. Thus, the endonuclease target site is located at a position which is not duplicated in 3Cs synthesis and is therefore present only in the wild type ss-phagemid vector construct. Hence, the method comprises here within step (d), enzymatically digesting the 3Cs DNA with an endonuclease specific for the target site. For example, as endonucleases in some embodiments restriction enzymes and their target sites are used. Exemplary restriction enzymes and their target sites are I-PpoI, SmaI, HpaI, I-SceI or I-CeuI. Any restriction recognition site can be used that do not occur in the template ss DNA nor in the introduced sequence I the mutagenic primer. In addition to the use of restriction endonucleases also any one of the following enzymes can be used to remove residual wild type plasmid: I-CeuI, I-PpoI, I-SceI, all homing endonucleases are preferred, all non-homing endonucleases, the usage of gene-perturbation target sequences for e.g. TALEN, ZFN, CRISPR/Cas and similar enzymes, the usage of prokaryotic and/or eukaryotic toxic nucleotide sequences with the aim of suppressing the amplification of such sequences and the usage of homology and/or recombination-based cloning sequences.

Another possibility to remove wild type DNA vector is to use the Kunkel method. Hence, the above problem is solved by the present invention by a method for the generation of a small RNA/DNA expressing (or encoding) vector, or a method of introducing a small RNA/DNA coding sequence into a vector, using the method of Kunkel for mutagenesis (Kunkel method). Preferred aspects therefore pertain to a method of introducing a small RNA/DNA sequence into a vector using the Kunkel method or Kunkel mutagenesis. The Kunkel method or Kunkel mutagenesis in context of the invention refers to the following procedure: the DNA fragment to be mutated is inserted into a phagemid (any f1 ori containing vector such as M13mp18/19) and is then transformed into an *E. coli* strain deficient in two enzymes, dUTPase (dut) and uracil deglycosidase (ung). Both enzymes are part of a DNA repair pathway that protects the bacterial chromosome from mutations by the spontaneous deamination of dCTP to dUTP. The dUTPase deficiency prevents the breakdown of dUTP, resulting in a high level of dUTP in the cell. The uracil deglycosidase deficiency prevents the removal of uracil from newly synthesized DNA. As the double-mutant E. coli replicates the phage DNA, its enzymatic machinery may, therefore, misincorporate dUTP instead of dTTP, resulting in single-strand DNA that contains some uracils (ssUDNA). The ssUDNA is extracted from the bacteriophage that is released into the medium, and then used as template for mutagenesis. An oligonucleotide containing the desired mutation or change in nucleotide sequence is used for primer extension. The formed heteroduplex DNA consists of one parental non-mutated strand containing dUTP and a mutated strand containing dTTP. The DNA is then transformed into an E. coli strain carrying the wildtype dut and ung genes. Here, the uracil-containing parental DNA strand is degraded, so that nearly all of the resulting DNA consists of the mutated strand. The method of the invention is in particular suitable for introducing guide RNA sequences into a genome editing vector for targeted genome editing.

A "Kunkel method" in context of the invention is a method comprising the amplification with a mutated primer using a single stranded uracilated DNA as a template, preferably a circular single stranded uracilated DNA. "Uracilated" shall refer to any DNA molecule containing one or more uracil bases in a nucleotide.

In the former invention a method is disclosed for generating a covalently closed circularized (ccc) DNA based small RNA/DNA expression vector or vector library, the method comprising the steps of
(a) Providing a single stranded (ss) phagemid vector construct comprising at least one uracil base and/or a DNA/RNA nuclease target site; the ss-phagemid vector construct comprising (i) at least one small RNA/DNA expression cassette comprising a RNA/DNA promoter and an empty target-small-RNA/DNA-sequence-introduction-site or a small RNA/DNA coding sequence, or partial sequence thereof, (ii) at least one origin for replication (ORI) of single strand DNA such as a phage ORI, and in particular a f1-origin, and
(b) Providing at least one species of mutagenic DNA-primer, wherein the mutagenic DNA-primer has the following structure in 3' to 5' direction: a first homology region, a target sequence region encoding for a small RNA/DNA to be expressed, and a second homology region, wherein the first homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 5' side, and wherein the second homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 3' side,
(c) Annealing of at least one species of mutagenic DNA primer to the ss-phagemid vector construct and amplifying a covalently closed circularized (ccc)heteroduplex dsDNA,
(d) Replacing the uracil-containing strand in the ccc-heteroduplex dsDNA with a non-uracil containing complementary DNA strand to obtain a cccDNA based small RNA/DNA expression vector or vector library.

In any case, herein, the term "phagemid" shall refer to a phage genome which has been converted into a plasmid.

In some preferred embodiments of the invention and the disclosure, the single stranded (ss) phagemid vector construct comprises additionally within its at least one small RNA/DNA expression cassette a restriction enzyme recognition site (restriction site). Preferably the restriction site is located in the single stranded (ss) phagemid vector construct between the regions which are complementary to the first homology region of the mutagenic DNA-Primer and the region complementary to the second homology region of the mutagenic primer. Thus, the restriction site is located at a position which is not duplicated in 3Cs synthesis and is therefore present only in the uracil containing ss-phagemid vector construct. The embodiment allows the additional digest of residual uracilated wild type DNA. Hence, the method in one embodiment further comprises a step of (c') between steps (c) and (d), comprising enzymatically digesting the 3Cs DNA with a restriction enzyme capable of a selective introduction of a double strand break at the restriction site. In context of the embodiment restriction sites, and their corresponding enzymes, are used which have a recognition sites which is rarely found in genomes. Exemplary restriction enzymes and their target sites are I-PpoI, SmaI, HpaI, I-SceI or I-CeuI. Any restriction recognition site can be used that do not occur in the template uricilated ss DNA. In addition to the use of restriction endonucleases also any one of the following enzymes can be used to remove residual wild type plasmid: I-CeuI, I-PpoI, I-SceI, all homing endonucleases are preferred, all non-homing endonucleases, the usage of gene-perturbation target sequences for e.g. TALEN, ZFN, CRISPR/Cas and similar enzymes, the usage of prokaryotic and/or eukaryotic toxic nucleotide sequences with the aim of suppressing the amplification of such sequences and the usage of homology and/or recombination-based cloning sequences.

In one preferred embodiment the invention provides a single stranded (ss) phagemid vector construct as described before, comprising at least two small RNA/DNA expression cassettes, more preferably at least three, 4, 5, 6, 7, 8, 9, 10, 15, 20, 30 and more small RNA/DNA expression cassettes as described herein before. In this embodiment, referred to as "multiplex", the vector molecule is able to generate a multitude of small RNA/DNAs to be expressed simultaneously.

In one additional embodiment, the at least one small RNA/DNA expression cassette, is at least two or more small RNA/DNA expression cassettes (multiplex expression of gRNA or other small RNA/DNA). In other preferred embodiments, the restriction sites used within the two or more small RNA/DNA expression cassettes are identical, similar or different.

The term "covalently closed circularized DNA" or "cccDNA" as used herein refers to DNA molecules that have assumed a circular form in contrast to linear DNA molecules such as eukaryotic chromosomal DNA or bacterial chromosomal DNA that comprises a nick or comprises a free 3'- or 5'-end. Moreover, the circular structure of the above referenced DNA molecules is covalently closed. cccDNA is well known in the art and is further described, for example, in KG. Hardy (ed) "Plasmids, a practical approach", IRL Press Oxford U.K., Washington D.C., U.S.A., 1987.

As used herein, the term "vector library" refers to a plurality of vectors (or plasmids) comprising a plurality of unique small RNA/DNA sequences to be expressed (e.g., siRNA, shRNA, gRNA or similar sequences) inserted in a RNA/DNA expression cassette. In preferred embodiments, vector libraries comprise at least $10^1$ or $10^2$, more preferably, at least $10^3$, even more preferably at least $10^4$, and still further more preferably, at least $10^5$, $10^6$, $10^7$, $10^8$ or $10^9$ unique vector sequences (meaning RNA/DNA sequences contained in each vector or plasmid).

In context of the present invention a small RNA shall be understood to include an siRNA, shRNA, an anti-miR, a guide RNA (gRNA) or guide DNA (gDNA). Most preferred is that the small RNA is a gRNA, and wherein the ss-phagemid vector construct comprises further, but is not limited to the presence of, a genome editing nuclease expression sequence, optionally operably linked to a promoter. It shall be understood that the invention pertaining to the provision of fixed pair gRNA vectors, the small RNA shall be a gRNA or sgRNA.

The present disclosure in some aspects provides a new method for the generation of higher order libraries of small RNA/DNA expressing vectors. In context of the invention, the term "higher order" shall mean that the library comprises multiple species of vectors which are different in the sequence of the small RNA/DNA to be expressed by/via the vector. The present method uses the mutagenic DNA-primer to introduce such sequences into the vector of choice. Therefore, in some embodiments the at least one species of mutagenic DNA-primer is at least two species of mutagenic DNA-primer, preferably is at least three, more preferably at least 4, 5, 6, 10, 50, 100, 1000, $10^4$, $10^5$, $10^6$, $10^7$, $10^8$, $10^9$, $10^{10}$, $10^{11}$ or $10^{12}$, species of mutagenic DNA-primer, and wherein each species of cccDNA has a different sequence in the small RNA/DNA coding sequence of choice.

In some embodiments of the present invention, the multitude of mutagenic DNA-primer sequence species are provided by introducing into the small RNA/DNA coding sequence (as contained in the mutagenic DNA-primer of the invention) of choice at least one or more IUPAC-encoded bases (e.g. degenerated base). A "degenerate base" or "degenerate position" is in the sequence nomenclature referred to as an "n". In context of the present invention a degenerate base is not a type of nucleotide base but denotes the possibility that in a preparation of nucleic acids having essentially the same sequence, the position "n" in said sequence allows the possibility of multiple kinds of bases at this position. Therefore, a preparation of nucleic acids having a sequence containing at least one "n" position denotes a mixture of nucleic acids having either adenine, guanine, thymine, or cytosine (with equal probability) at the position n. For example, if oligonucleotides are synthesized, the reaction at one or more positions may be conducted using as donor nucleotides an equal amount of adenine, guanine, thymine, and cytosine containing nucleotides. In such a reaction, each of these nucleotides have an equal chance to be added to the growing oligonucleotide chain, and therefore allows the creation of a mixture of molecules with different bases at the position "n". The same principle can be used if at one positions only two or three different bases are intended to be introduced. In the present disclosure the following nomenclature is used: R=G, A (purine), Y=T, C (pyrimidine), K=G, T (keto), M=A, C (amino), B=G, T, C (all but A), D=G, A, T (all but C), H=A, C, T (all but G), V=G, C, A (all but T) and N=A, G, C, T (any).

In other embodiments of the present invention the small RNA/DNA coding sequence is at least 10 nucleotides to 200 nucleotides long, more preferably 10 to 100, more preferably 10 to 50, more preferably 10 to 30, more preferably 15 to 30, more preferably 15 to 25, most preferably 17 to 23, most preferably about 20. The sequence length may be adjusted by the skilled artisan depending on the type of small RNA/DNA to be expressed. The preferred length of guide RNA and shRNA or siRNA are different but are well known to the skilled artisan.

The mutagenic DNA-primer of the disclosure comprises flanking homology regions which are used to anneal the primer with the ss circular uracilated vector molecule used in the reaction of the invention. The flanking regions are therefore preferably of a length that allows for an annealing of the mutagenic DNA-primer to the template at conditions suitable for primer extension. The lengths of the 3' or 5' homology regions may be identical or different. In some embodiments, each of the homology regions has a length of at least 5 nucleotides, preferably at least 10 nucleotides, more preferably 5 to 40 nucleotides, most preferably 10 to 30, or 10 to 20, most preferably 13 to 18, and even more preferably about 15 nucleotides. Most preferred are 5-40 nucleotides.

In some embodiments of the methods of the invention the single stranded (ss) phagemid vector construct is provided by the following additional method steps:
 (aa) amplification of a dsDNA phagemid vector of the same sequence in a bacterial strain deficient for dUTPase and/or uracil glycosylase, and/or their homologs, paralogs or orthologues, preferably in the CJ236 strain, to obtain uracil containing heteroduplex dsDNA phagemid vectors and
 (bb) generation of phage particles comprising an uracil containing ssDNA, and
 (cc) purifying from said phage particles said uracil containing ssDNA to obtain the ss-phagemid vector construct comprising at least one uracil base.

In another embodiment preferred according to the various aspects of the invention, the bacterial strain deficient for dUTPase and/or uracil glycosylase, and/or their homologs, paralogs or orthologues, preferably the CJ236 strain, comprises a helper phagemid, or wherein in step (bb) said bacterial strain deficient for dUTPase and/or uracil glycosylase, and/or their homologs, paralogs or orthologues, preferably in the CJ236 strain in infected with a helper phage, wherein the helper phagemid or helper phage is preferably M13K07.

In some embodiments it is preferred that step (d) of the method for generating the library vector according to I is performed by transforming and amplifying said ccc-heteroduplex dsDNA in a bacterium having a functional dUTPase and/or uracil glycosylase activity, such as XL1 or SS320, to obtain said cccDNA.

In some embodiments of the present invention the amplification of a covalently closed circularized (ccc)-heteroduplex dsDNA in step (c) is performed by using an enzyme having DNA polymerase activity, for example a T7 DNA polymerase, optionally in conjunction with a DNA ligase, such as T4 DNA ligase or alternatives thereof, which are known to the skilled artisan.

In another aspect, the object of the invention is solved by providing a vector or vector library generated according to the method of the invention as disclosed herein. The vector library produced according to the invention is preferably characterized by comprising at least $10^6$, more preferably $10^7$, $10^8$, and most preferably $10^9$ different species of vector sequences as described herein.

Furthermore, there is provided a method of genome wide screening cellular phenotypes, the method comprising the use of a vector library produced according to a method of the invention.

The screening method of the invention may comprise the steps of introducing the vector library of the invention—in particular the genome wide library—into a population of target cells, and phenotyping the transduced cells using any assay of interest. Any cell having a phenotype of interest can in a next step be analyzed for the identity of the transduced gRNA or RNAi, in order to identify a gene or genomic region involved in the generation of the phenotype. For example, the cells may be contacted with a cell-death inducing agent, and the surviving cells are analyzed for the transduced 3Cs vector in order to identify the genetic perturbation responsible for the resistance against the cell death-inducing agent.

In another aspect of the invention there is a kit provided for performing the method as described herein above, the kit comprising
(a) phagemid vector construct comprising
  (i) at least one guide RNA (gRNA)/guide DNA (gDNA) expression cassette comprising a gRNA/gDNA promoter, an empty gRNA/gDNA targeting sequence introduction site or a gRNA/gDNA targeting sequence,
  (ii) at least one phage replication origin, and
  (iii) at least one expression cassette comprising a sequence coding for a genome editing nuclease under control of a promoter sequence;
(b) a DNA polymerase, optionally a DNA ligase;
(c) a preparation of bacterial cells which have a functional dUTPase and/or uracil glycosylase activity,
(d) and, optionally, instructions for the use of the kit of the invention.

In some embodiments the DNA polymerase is a T7 DNA polymerase, and/or the DNA ligase is a T4 DNA ligase, or any generally known alternatives of thereof.

In other embodiments of the invention, the phagemid vector construct of the invention is a single stranded (ss)-phagemid vector construct comprising at least one uracil base.

In further embodiments, the phagemid vector is a dsDNA vector.

The kit of the invention may in some embodiments comprise a preparation, sample or culture of bacterial cells deficient for dUTPase and/or uracil glycosylase, and/or their homologs, paralogs or orthologues, preferably the CJ236 strain. Such strains are generally known in the pertinent art.

In other embodiments pertaining to the kit of the invention, the bacterial cells further comprise/contain a helper phagemid, preferably M13K07.

In other embodiments of the invention the kit according to the invention further comprises a preparation of helper phagemid, or helper phages, wherein the helper phagemid, or helper phages, are preferably M13K07 particles.

II. Generating Fixed Pair gRNA Vectors and Vector Libraries Using cccDNA

For the present invention it was a particular objective to allow the easy and quick generation of gRNA vectors that comprise two or more expressible gRNA sequences ("fixed pair"). In order to solve this problem, the inventors applied and varied the above described cccDNA and Kunkel based method. The above disclosure, in particular any definitions equally apply to the following description of the particular aspects and embodiments of the present invention, of course where it is technically reasonable.

In context of the present invention the term "fixed pair" shall refer to two or more distinct and different small RNA sequences, in particular gRNA sequences suitable for the targeted editing of genomes (CRISPR based genome editing). A fixed pair according to the invention preferably pertains to a multitude of such sequences, such as 2, 3, 4, 5, 6, 7, 8 or more small RNA sequences. In some preferred aspects and embodiments, the term pertains to two such sequences.

The above described objective of the current invention is solved in a first aspect by a nucleic acid, comprising a modified tracrRNA sequence having a sequence identity of between 50% and 95% compared to the respective wild type sequence of the tracrRNA, and wherein the modified tracrRNA sequence comprises at least one, preferably at least two or three, sequence variation(s) compared to the wild type tracrRNA sequence. The inventors have developed multiple non-wild-type tracrRNA sequences which display improved characteristics such as a reduced ability to fold into sterically unfavorable three-dimensional structures when cloned into an exverted or inverted repeat.

As used herein, the term "tracrRNA" refers to a trans-activating RNA that associates with the crRNA sequence through a region of partial complementarity and serves to recruit a Cas9 nuclease, or a CAS9 related nuclease or protein, to the protospacer motif. In one embodiment, the tracrRNA is at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more nucleotides in length. In one embodiment, the tracrRNA is about 85 nucleotides in length.

Sometimes, the crRNA and tracrRNA are engineered into one polynucleotide sequence referred to herein as a "single guide RNA" or "sgRNA." The crRNA equivalent portion of the sgRNA is engineered to guide the Cas9 nuclease to target any desired protospacer motif. In one embodiment, the tracrRNA equivalent portion of the sgRNA is engineered to be at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more nucleotides in length.

The protospacer motif abuts a short protospacer adjacent motif (PAM), which plays a role in recruiting a Cas9/RNA complex. Cas9 polypeptides recognize PAM motifs specific to the Cas9 polypeptide. Accordingly, the CRISPR/Cas9 system can be used to target and cleave either or both strands of a double-stranded polynucleotide sequence flanked by particular 3' PAM sequences specific to a particular Cas9 polypeptide. PAMs may be identified using bioinformatics or using experimental approaches. Esvelt et al., 2013, Nature Methods. 10(11):1116-1121, which is hereby incorporated by reference in its entirety.

In some embodiments, the method of the invention according to I and II is for the generation of vectors suitable for genome editing. Such genome editing vectors are usually characterized by the presence of a guide RNA expression cassette which comprises a site for the introduction of the gRNA sequence of choice which will guide the genome editing complex to the target site in the genome. As such the gRNA expression cassette comprises both the gRNA portion for targeting and the gRNA segment for binding to the genome editing nuclease (Cas). The gRNA expression cassette is usually in operable linkage (transcriptional control) with an RNA promoter such as the human or mouse U6 promoter or human 7SK promoter or mouse H1 promoter. However, other RNA promoters are known to the skilled artisan. The genome editing vector usually further includes an expressible genome editing nuclease such as Cas9. With regard to the invention according to aspect II, further disclosure is provided herein below.

As used herein, the term "guide RNA" generally refers to an RNA sequence or molecule (or a group of RNA molecules collectively) that can bind to a Cas protein and aid in targeting the Cas protein to a specific location within a target polynucleotide (e.g., a DNA or RNA). A guide RNA can comprise a crRNA segment and a tracrRNA segment. As used herein, the term "crRNA" or "crRNA segment" refers to an RNA molecule or portion thereof that includes a polynucleotide-targeting guide sequence, a stem sequence, and, optionally, a 5'-overhang sequence. The term "tracrRNA" or "tracrRNA segment" is further defined herein below but refers to an RNA molecule or portion thereof that includes a protein-binding segment (e.g., the protein-binding segment is capable of interacting with a CRISPR-associated protein, such as a Cas9). The term "guide RNA" encompasses also single guide RNA (sgRNA), where the crRNA segment and the tracrRNA segment are located in the same RNA molecule. The term "guide RNA" also encompasses, collectively, a group of two or more RNA molecules, where the crRNA segment and the tracrRNA segment are located in separate RNA molecules. Further preferred structures and embodiments of guide RNA are described herein below.

The term "scaffold" refers to the portions of guide RNA molecules comprising sequences which are substantially identical or are highly conserved across natural biological species. Scaffolds include the tracrRNA segment and the portion of the crRNA segment other than the polynucleotide-targeting guide sequence at or near the 5' end of the crRNA segment, excluding any unnatural portions comprising sequences not conserved in native crRNAs and tracrRNAs.

A genome editing vector of the various embodiments and aspects of the invention may encode a f1 bacteriophage origin of replication, a RNA polymerase promoter, a guide RNA scaffold for the CRISPR/Cas system, a RNA-guided nuclease, or any other suitable alternatives thereof. Preferred constructs are lenti virus-based constructs. Standard CRISPR/Cas vectors known in the art which may be used in context of the invention or may serve as a blueprint for the development of other genome editing vectors are the vectors known as pLentiCRISPR, pLentiCRISPRv2 or pLenti-Guide.

In some embodiments, the modified tracrRNA sequence and the wild type tracrRNA sequence have a binding affinity to a RNA/DNA or to a genome editing nuclease which differ not more than 50%, more preferably 20%, more preferably 10%, 5%, 3% most preferably 1%, from each other.

As used herein, the term "CRISPR nuclease" refers to a recombinant protein which is derived from a naturally occurring Cas nuclease which has nuclease or nickase activity and which functions with the gRNAs of the present invention to introduce DSBs (or one or two SSBs) in the targets of interest, e.g., the DYS gene. In embodiments, the CRISPR nuclease is SpCas9. In embodiments, the CRISPR nuclease is Cpf1. In other embodiments, the CRISPR nuclease is SaCas9. A CRISPR nuclease can also be a TALEN enzyme. In another embodiment, the CRISPR nuclease is a Cas9 protein having a nickase activity. As used herein, the term "Cas9 nickase" refers to a recombinant protein which is derived from a naturally occurring Cas9 and which has one of the two nuclease domains inactivated such that it introduces single stranded breaks (SSB) into the DNA. It can be either the RuvC or HNH domain. In a further embodiment, the Cas protein is a dCas9 protein fused with a dimerization-dependent FoKI nuclease domain. Exemplary CRISPR nucleases that may be used in accordance with the present invention are provided in Table 1 below. A variant of Cas9 can be a Cas9 nuclease that is obtained by protein engineering or by random mutagenesis (i.e., is non-naturally occurring). Such Cas9 variants remain functional and may be obtained by mutations (deletions, insertions and/or substitutions) of the amino acid sequence of a naturally occurring Cas9, such as that of S. pyogenes.

CRISPR nucleases such as Cas9/nucleases cut 3-4 bp upstream of the PAM sequence. CRISPR nucleases such as Cpf1 on the other hand, generate a 5' overhang. The cut occurs 19 bp after the PAM on the targeted (+) strand and 23 bp on the opposite strand (62). There can be some off-target DSBs using wildtype Cas9. The degree of off-target effects depends on a number of factors, including: how closely homologous the off-target sites are compared to the on-target site, the specific site sequence, and the concentration of nuclease and guide RNA (gRNA). These considerations only matter if the PAM sequence is immediately adjacent to the nearly homologous target sites. The mere presence of additional PAM sequences should not be sufficient to generate off target DSBs; there needs to be extensive homology of the protospacer followed or preceded by PAM.

TABLE 1

Non-exhaustive list of CRISPR-nuclease systems from different species. Also included are engineered variants recognizing alternative PAM sequences (see Kleinstiver, BP. et al. (2015). Broadening the targeting range of Staphylococcus aureus CRISPR-Cas9 by modifying PAM recognition. Nat Biotechnol 33(12): 1293-1298.).

| CRISPR nuclease | PAM Sequence |
|---|---|
| Streptococcus pyogenes (SP); SpCas9 | NGG + NAG |
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| Staphylococcus aureus (SA); SaCas9 | NNGRRT or NNGRR(N) |
| SaCas9 KKH variant | NNNRRT |
| Neisseria meningitidis (NM) | NNNNGATT |
| Streptococcus thermophilus (ST) | NNAGAAW |
| Treponema denticola (TD) | NAAAAC |
| AsCpf1 | TTTN |
| LbCpf1 | TTTN |

In some preferred embodiments the modified tracrRNA sequence of the invention comprises a nucleotide sequence according to any one of SEQ ID NOs: 8-10.

In context of the present invention the at least one sequence variation is a deletion, substitution, insertion, inversion, addition or chemical modification of at least one nucleic acid residue.

In another aspect the present invention provides a method for generating a modified tracrRNA sequence, the method comprising the steps of
 a) Analyzing the structure of an RNA/DNA or genome editing nuclease in complex with a wild-type tracrRNA,
 b) Identifying in the wild-type tracrRNA sequence at least one residue which is not in contact with the RNA/DNA or genome editing nuclease, preferably at least 2, more preferably at least 3 residues not in contact with the RNA/DNA or genome editing nuclease, and
 c) Mutating said at least one residue, preferably at least 2, more preferably at least 3 residues, not in contact with the RNA/DNA or genome editing nuclease, and thereby obtaining a modified tracrRNA sequence, comprising between 50 and 95% sequence identity to the wild type tracrRNA sequence, and wherein the modified tracrRNA sequence maintains a binding affinity to a RNA/DNA or genome editing nuclease of at least 50%, more preferably 80%, more preferably 90%, 95%, 97%, and most preferably 99%, compared to the binding affinity of the wild type tracrRNA sequence.

For example, the tracrRNA sequence is complexed with the respective CRISPR nuclease and then structurally analysed, for example by X-ray crystallography, NMR spectroscopy, and dual polarisation interferometry, to determine the structure of nuclease bound to its tracrRNA.

Preferably, the so generated mutated tracrRNA sequence is 50% (preferably 60%, 70%, 80%, 85%, or 90%) to 95% identical in sequence compared to the respective wild type sequence of the tracrRNA.

In yet another aspect the object of the invention is solved by a method for generating a covalently closed circularized (ccc) DNA vector for expressing a fixed pair of guide RNAs, the method comprising the steps of:
 (a) Providing a recipient vector comprising two extraverted [expression direction facing in outward orientation from each other] gRNA expression cassettes, wherein each gRNA expression cassette comprises a gRNA placeholder sequence and a tracrRNA (sgRNA) sequence,
 (b) Providing a mutagenic DNA primer comprising in this order
  i. a first homology region capable of binding to the first gRNA expression cassette,
  ii. a first predetermined gRNA sequence to be expressed,
  iii. a linker sequence,
  iv. a second predetermined gRNA sequence to be expressed,
  v. a second homology region capable of binding to the second gRNA expression cassette,
 (c) generating a cccDNA vector using the recipient vector and the mutagenic DNA primer,
 (d) introducing into the linker sequence of the cccDNA vector a promoter fragment comprising two extraverted RNA promoter sequences to obtain the cccDNA vector for expressing a fixed pair of guide RNAs.

A gRNA placeholder or gRNA placeholder sequence shall be understood as either a randomly selected gRNA sequence that is intended to get replaced by the first or second gRNA sequence to be expressed of the fixed pair of the invention in course of performing the above described method. Instead of a random gRNA sequence, also any other random sequence can be used. The length of the sequence is chosen to accommodate the overall length of the mutagenic DNA primer to allow for an efficient hybridization and primer synthesis.

In preferred embodiments, the tracrRNA sequence of one or both the gRNA expression cassettes is a modified or mutated tracrRNA sequence as described herein above. Preferably the tracrRNA sequence is a sequence according to any one of SEQ ID NO: 7 to 10. Most preferably one of the tracrRNA sequences is a sequence according to SEQ ID NO:10, or a sequence at least 80, 85, 90 or 95% identical thereto.

In some embodiments in step (a) the two gRNA placeholder sequences are separated by a linker, and wherein the linker sequence is identical to the linker sequence in the mutagenic DNA primer. Preferably the linker sequence comprises a restriction enzyme recognition site, such as a restriction enzyme recognition site for blunt ligation, or restriction enzyme recognition site for sticky end ligation. Ligation into a blunt or sticky end restriction enzyme breaking point does not allow for a directional cloning of an insert sequence. However, by using two different restriction nuclease recognition site, in sufficient spacing from each other, allows for a directional cloning, as the two different sticky end sequences of the two restriction enzyme recognition sites are incompatible and allow an insert sequence to be ligated into the breaking point in only one direction. Hence, in some embodiments, the linker sequence comprises two restriction enzyme recognition sites, preferably two different restriction enzyme recognition sites for directional RNA promoter ligation.

In some preferred embodiments the recipient vector comprises any one of, or all of, or any combination of:
 phage origin of replication (ORI), such as an f1 ORI,
 an expression cassette for a gene editing nuclease,
 one or more selection marker.

In some embodiments the method according to the invention is preferred, wherein in step (c) the cccDNA vector is generated by following step of:
 (a') providing the recipient vector as single stranded (ss) phagemid vector,
 (b') annealing the mutagenic DNA primer to said ss phagemid vector,
 (c') amplifying a covalently closed circularized (ccc)-heteroduplex dsDNA therefrom, and
 (d') removing residual wild type phagemid vector DNA.

In preferred embodiments in step (d) of the invention the promoter fragment is introduced into the linker sequence by inducing a double strand break in the linker sequence, for example using a restriction enzyme, ligating said promoter element into the so induced double strand break double strand break. The term "restriction enzyme sequence" refers to a specific double stranded-DNA sequence which is recognized and cut by bacterial enzymes, each of which cut double-stranded DNA at or near a specific nucleotide sequence.

The term "sticky end" or "overhang" as used herein is generally interpreted consistently with the understanding of one of ordinary skill in the related art and includes a linear double stranded nucleic acid molecule having one or more unpaired nucleotide species at the end of one strand of the molecule, where the unpaired nucleotide species may exist on either strand and include a single base position or a plurality of base positions (also sometimes referred to as "cohesive end"). The term "blunt end" or "blunt ended" as used herein generally refers to a linear double stranded nucleic acid molecule having an end that terminates with a pair of complementary nucleotide base species, where a pair of blunt ends are always compatible for ligation to each other. Preferred restriction enzyme sites are those used in the example section of this application. However, alternative endonuclease sites are however well known in the art. Preferred in context of the present invention is that the used restriction enzyme induces either a sticky end double strand break or a blunt ended double strand break. In some embodiments it might be preferable that the linker comprises two different restriction enzyme recognition sites in close proximity to each other that are used to allow for a directional introduction of said promoter element. A close proximity in some embodiments is that both recognition sites are not more than 50, preferably 20, 10 or 5 nucleic acids apart from each other.

In another aspect the present invention then pertains to a method for generating a covalently closed circularized (ccc) DNA based guide RNA expression vector or vector library, the method comprising the steps of
 (a) Providing a single stranded (ss) phagemid vector comprising (i) at least two guide RNA expression cassettes, wherein each of said guide RNA expression cassettes comprises a tracrRNA (sgRNA) sequence and an empty target-guide-RNA-sequence-introduction-site or a guide RNA placeholder sequence, or partial sequence thereof, (ii) at least one origin for replication (ORI) of single strand DNA such as a phage ORI, and in particular a f1-origin, (b) Providing at least one species of mutagenic DNA-primer, wherein the mutagenic DNA-primer has the following structure in 3' to 5' direction: a first homology region, a first target sequence region encoding for a first guide RNA to be expressed, a second homology region, a second target sequence region encoding for a second guide RNA to be expressed, and a third homology region, wherein the first homology region is complementary to, or is capable of annealing to, a sequence of the ss-phagemid vector construct flanking the empty first target-guide-RNA-sequence-introduction-site or the first guide RNA coding sequence, or partial sequence thereof, on the 5' side, and wherein the second homology region is complementary to, or is capable of annealing to, a sequence of the ss-phagemid vector construct flanking the empty first target-guide-RNA-sequence-introduction-site or the first guide RNA coding sequence, or partial sequence thereof, on the 3' side, and wherein the third homology region is complementary to, or is capable of annealing to, a sequence of the ss-phagemid vector construct flanking the empty second target-guide-RNA-sequence-introduction-site or the second guide RNA coding sequence, or partial sequence thereof, on the 3' side, (c) Annealing of at least one species of mutagenic DNA-primer to the ss-phagemid vector construct and amplifying a covalently closed circularized (ccc)heteroduplex dsDNA therefrom, (d) Removing residual wild type phagemid vector DNA, and (e) Providing an RNA promoter capable of expressing the first guide RNA and the second guide RNA.

As mentioned before it is preferable for the method of the invention that the tracrRNA sequences of the one of the at least two guide RNA expression cassettes is not identical to the tracrRNA sequence of the other of the at least two guide RNA expression cassettes. This is to avoid the formation of three dimensional structures in the construct due to the exverted repeat orientation of the tracrRNA sequences. Such three dimensional structures may impair the further method steps for generation of the fixed pair vector. It is preferable that the tracrRNA sequences of the one and the other guide RNA expression cassettes are characterized in that their sequence homology is between 50 and 95%, and/or wherein the tracrRNA sequences have the ability of binding to the same or different RNA/DNA or genome editing nuclease.

The two gRNA expression cassettes are preferably in extraverted orientation, preferably the first guide RNA is oriented in 3' to 5' direction, and the second guide RNA is oriented in 5' to 3' direction.

Also as mentioned before the sequence between the first guide RNA sequence and the second guide RNA sequence comprises at least one restriction endonuclease recognition sequence that is recognized by a restriction endonuclease. Such nucleases and their recognition sites are described herein above.

Preferably, in context of the invention step (e) comprises the following:

(i) Contacting the ccc-heteroduplex dsDNA with at least one restriction endonuclease, wherein the at least one restriction endonuclease is capable of cleaving the at least one restriction endonuclease recognition sequence located between the first guide RNA sequence and the second guide RNA sequence, and wherein the conditions are sufficient to produce a cleavage product comprising a first restriction endonuclease recognition sequence half-site and a second restriction endonuclease recognition sequence half-site, (ii) Providing a bidirectional DNA/RNA fragment comprising a first restriction endonuclease recognition sequence half-site, a first RNA promoter, a second RNA promoter, and a second restriction endonuclease recognition sequence half-site, wherein the first recognition sequence half-site is compatible with the first recognition sequence half-site of the cleavage product from step (i), and the second recognition sequence half-site is compatible with the second recognition sequence half-site of the cleavage product from step (i), and wherein the first RNA promoter is oriented in 3' to 5' direction, and the second RNA promoter is oriented in 5' to 3' direction, and (iii) Combining the cleavage product from step (i) and the bidirectional DNA/RNA fragment from step (ii) under ligation conditions sufficient to produce a ligation product composition, wherein the 5' end of the first guide RNA is operatively linked to the 3' end of the first RNA promoter, and the 5' end of the second guide RNA is operatively linked to the 3' end of the second RNA promoter.

The guide RNA sequences of the invention are ultimately expressed under control of an RNA promoter. Preferably the first RNA promoter and the second RNA promoter are identical or, preferably, are not identical. The term "promoter" is understood to mean a regulatory sequence/element or control sequence/element that is capable of binding/recruiting a RNA polymerase and initiating transcription of sequence downstream or in a 3' direction from the promoter. A promoter can be, for example, constitutively active or always on or inducible in which the promoter is active or inactive in the presence of an external stimulus. Example of RNA promoters include h7SK, T7 promoters or U6 promoters.

The vectors used in accordance with the invention in some embodiments further comprise a RNA/DNA or genome editing nuclease (CRISPR nuclease) expression sequence in wild type or engineered form, optionally operably linked to a promoter (stable or inducible), wherein the promoter is preferably suitable for the expression of mRNA.

Guide RNA (gRNA) coding sequence is at least 10 nucleotides to 200 nucleotides long, more preferably 10 to 50, more preferably 10 to 30, more preferably 15 to 30, more preferably 15 to 25, most preferably 17 to 23, and even more preferably about 20 nucleotides long.

In context of the herein described methods, the homology regions has a length of at least 5 nucleotides, preferably at least 10 nucleotides, more preferably 5 to 40 nucleotides, most preferably 10 to 30, or 10 to 20, most preferably 13 to 18, and even more preferably about 15 nucleotides. In other alternative or additional embodiments of the invention, the homology region consists of a sequence having an annealing temperature of about 40 to 60° C., and preferably about 45 to 55° C., and most preferably a Tm of 50° C.+/−3.

The methods of the invention in some aspects are used to generate a covalently closed circularized (ccc) DNA based guide RNA expression vector or vector library, wherein each vector comprises a defined combination of at least two different gRNAs (fixed pair).

As a non-limiting example of the invention a mutagenic DNA-primer may have a sequence according to any of SEQ ID NOs: 1-5.

Figure 11:
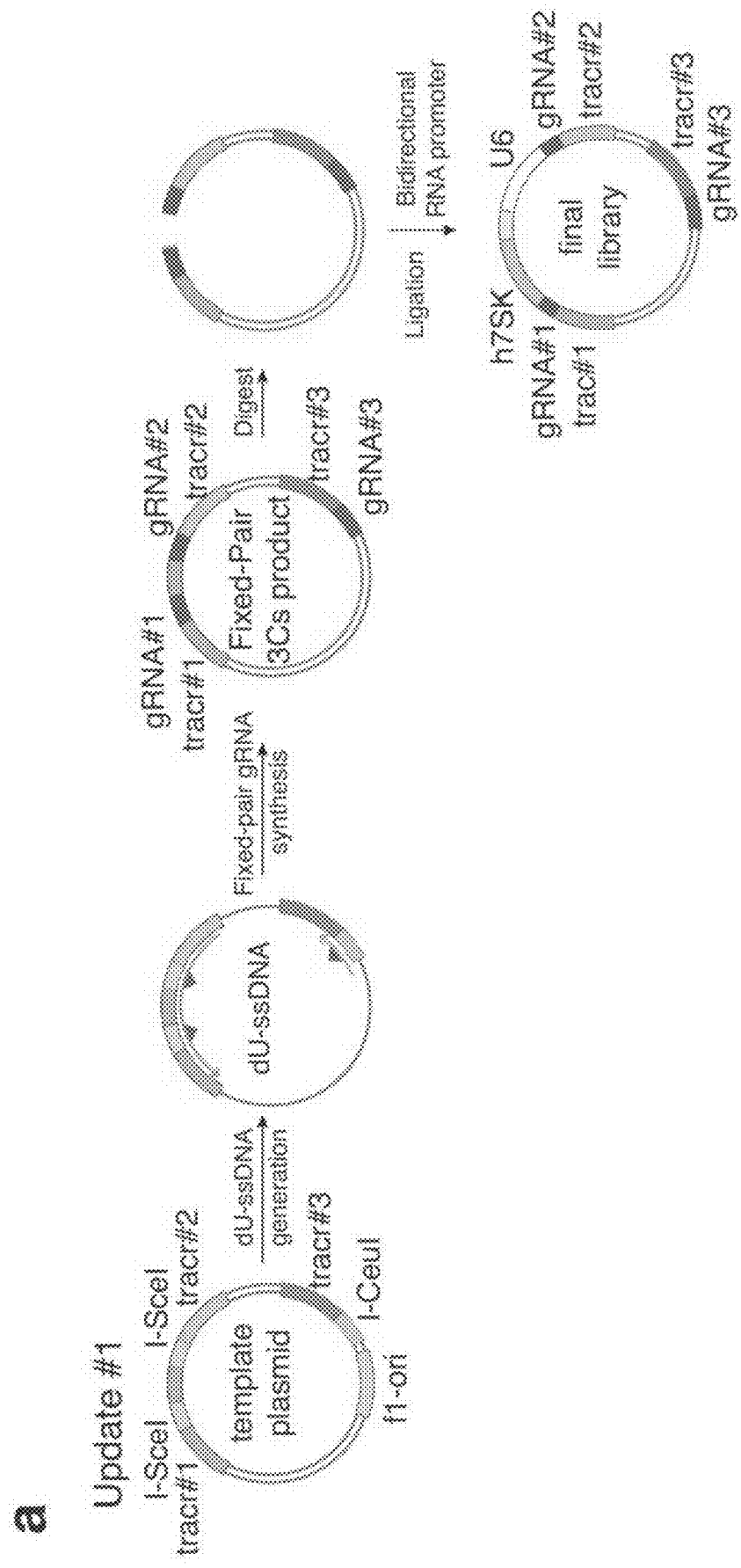
Figure 11:
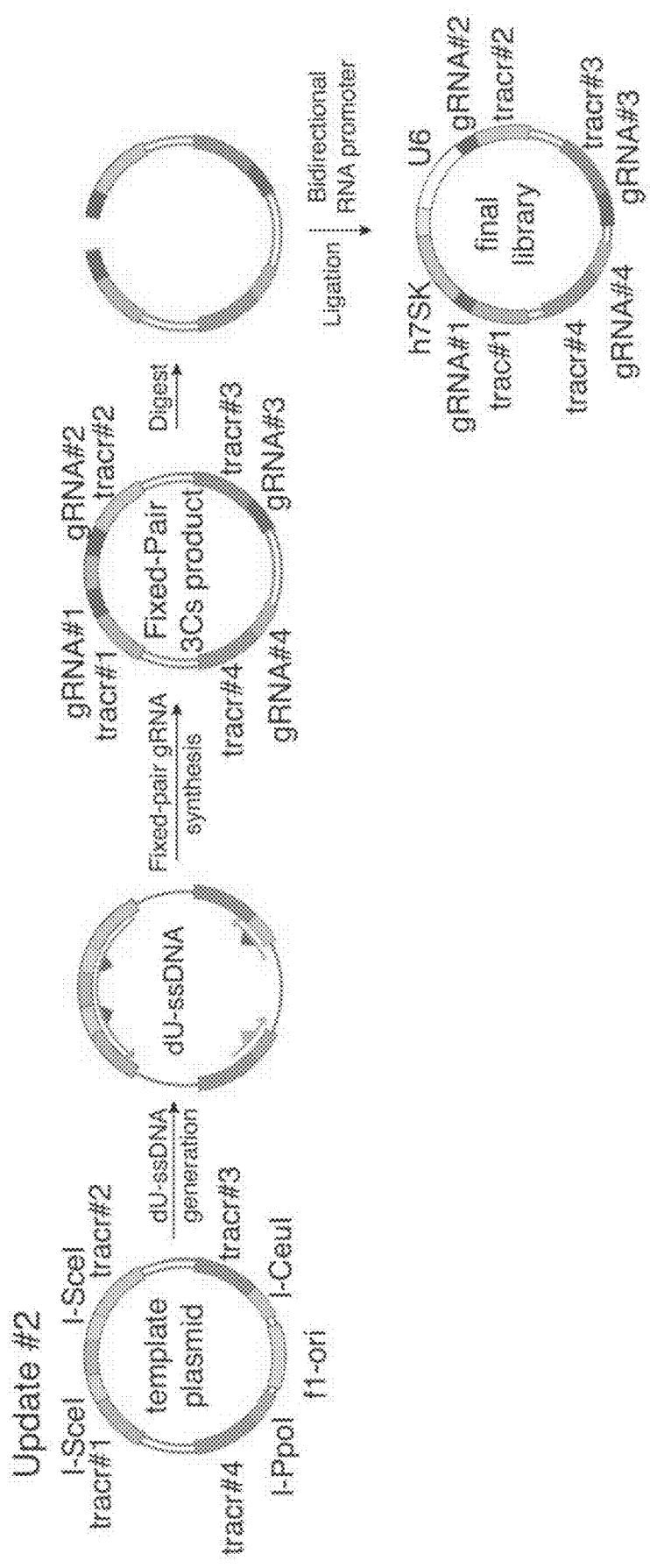
Figure 11:
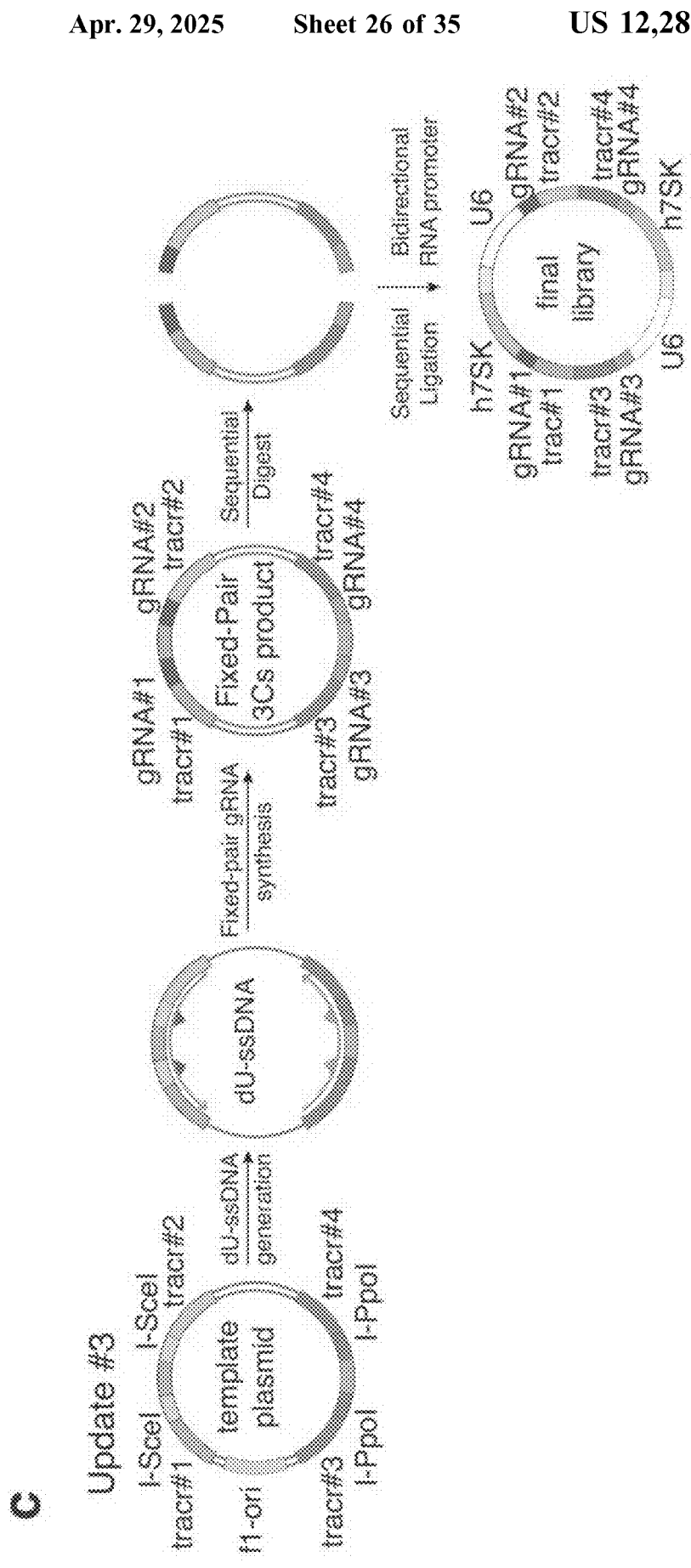

In further preferred embodiments the above described technology for generating a "fixed pair" gRNA expression vector is used according to the additional embodiments depicted in FIG. 11. In brief, the herein described fixed pair methods are used in a direct combination with the method of generating a gRNA expression vector as disclosed herein under section I. This embodiment may include that the additional used tracrRNA sequence of the additional gRNA expression cassettes are also not identical to the other tracrRNA sequences of the template vector. One additional or alternative embodiment then pertains to the method of the fixed pair technology, which is used twice concomitantly in the same vector (see FIG. 11c).

Part of the invention forms also a vector library obtainable by the herein described methods.

In another aspect the invention provides a nucleic acid vector for introducing and expressing two different guide RNA sequences, the vector comprising, in extraverted orientation, [expression direction facing in outward orientation from each other]:
(i) a first gRNA expression cassette, comprising a first tracrRNA (sgRNA) sequence and a first gRNA placeholder sequence, and
(ii) a second gRNA expression cassette, comprising a second tracrRNA (sgRNA) sequence and a second gRNA placeholder sequence. Preferably, the first and the second tracrRNA sequences are not identical. In some embodiments a nucleic acid sequence consisting of the first and the second tracrRNA sequences in an extraverted repeat orientation has a minimum free energy of not less than about 100 to −100 kcal/mol.

In some preferred embodiments, the vector comprises a linker between the first and the second gRNA expression cassette, wherein the linker is flanked by the gRNA placeholder sequences. Preferably, the linker comprises a restriction endonuclease recognition site, preferably suitable for introducing blunt end or sticky end double strand breaks (see above).

The above described embodiments for the template vector suitable for use in the method of generating the fixed-pair gRNA vector equally apply.

Yet another aspect of the invention then pertains to a kit of parts comprising any compounds of the herein described invention, optionally, further comprising any buffer or reagent suitable for any of the following: transformation of bacteria, and/or DNA/RNA isolation, and/or restriction enzyme digestion, and/or ligation.

III. Enhanced Fixed-Pair 3Cs Gene Editing

In yet another aspect the object of the invention is solved by an enhanced method for generating a covalently closed circularized (ccc) DNA vector for expressing a fixed pair of guide RNAs. Since the above method disclosed under section II above requires still a residual classical cloning step, a further strategy, however developed on the basis of the fixed-pair principle is disclosed.

CRISPR methods may include two possibilities for the generation of a functional RNA complex including the necessary structural elements as well as the guide sequence for complementary binding to the target DNA. Often used is a guide RNA as a single molecule comprising the target complementary region (sometimes referred to as "protospacer"), fused to a crRNA "repeat" sequence which is complementary to, and fused to a tracrRNA, resulting in the formation of a double strand of the crRNA repeat sequence and the tracrRNA sequence. However, also possible is that the target guide sequence is fused to the crRNA sequence and a tracrRNA are expressed as separate molecules but still form a complex via complementary base pairing of the crRNA sequence to the tracrRNA. The inventors used the latter strategy for the third aspect of the present invention.

Hence, the enhanced 3Cs fixed pair method of the invention comprises the steps of:
(a) Providing an enhanced recipient vector comprising (x) two inverted [expression direction facing in orientation against each other] enhanced gRNA expression cassettes (a first and a second enhanced gRNA expression cassette), wherein each enhanced gRNA expression cassette comprises in that order: (i) optionally an RNA promoter, (ii) a gRNA placeholder sequence, and (iii) a crRNA (an sgRNA sequence lacking the Tracer sequence) sequence, and (y) a tracrRNA expression cassette;
(b) Providing an enhanced mutagenic DNA primer comprising two gRNA sequences of interest and homology regions capable to mediate a binding of the mutagenic DNA primer to the two inverted enhanced gRNA expression cassettes; and
(c) Generating a cccDNA vector using the recipient vector and the mutagenic DNA primer.

The method in preferred embodiments comprises the steps of generative cccDNA as described herein elsewhere, preferably by using the so called Kunkel mutagenesis method for the introduction of the sequences of the enhanced mutagenic DNA primer into the enhanced recipient vector. Such method in may in preferred embodiments comprise the following sub-steps in method step (c): (a') Providing the recipient vector as single stranded (ss) phagemid vector, (b') Annealing the mutagenic DNA primer to said ss phagemid vector, (c') Amplifying a covalently closed circularized (ccc)-heteroduplex dsDNA thereFrom, and (d') Removing residual wild type phagemid vector DNA.

The enhanced 3Cs fixed pair method of the invention does not require a step of introducing a linker fragment comprising the RNA promoter regions for gRNA expression, and therefore is less prone to typical cloning problems and errors.

In some preferred embodiments of the invention the tracrRNA expression cassette is not located between the inverted enhanced gRNA expression cassettes of the enhanced recipient vector.

In some preferred embodiments of the invention, the tracrRNA expression cassette comprises a tracrRNA coding sequence lacking the crRNA sequence and being operably linked to a promoter suitable for expression of the tracrRNA.

In some preferred embodiments of the invention, the tracrRNA sequence lacking the crRNA sequence, and the crRNA sequence, when expressed by the recipient vector, will produce RNA molecules which interact with each other to form a functional crRNA-tracrRNA complex.

For the purposes of the present aspect of the invention the crRNA sequence is complementary to a part of the tracrRNA sequence lacking the crRNA sequence. Hence, upon expression of the crRNA (preferably when fused to the gRNA sequence), the crRNA binds to the tracrRNA and hence forms a functional RNA complex for mediating Cas9 dependent gene editing.

Figure 12:
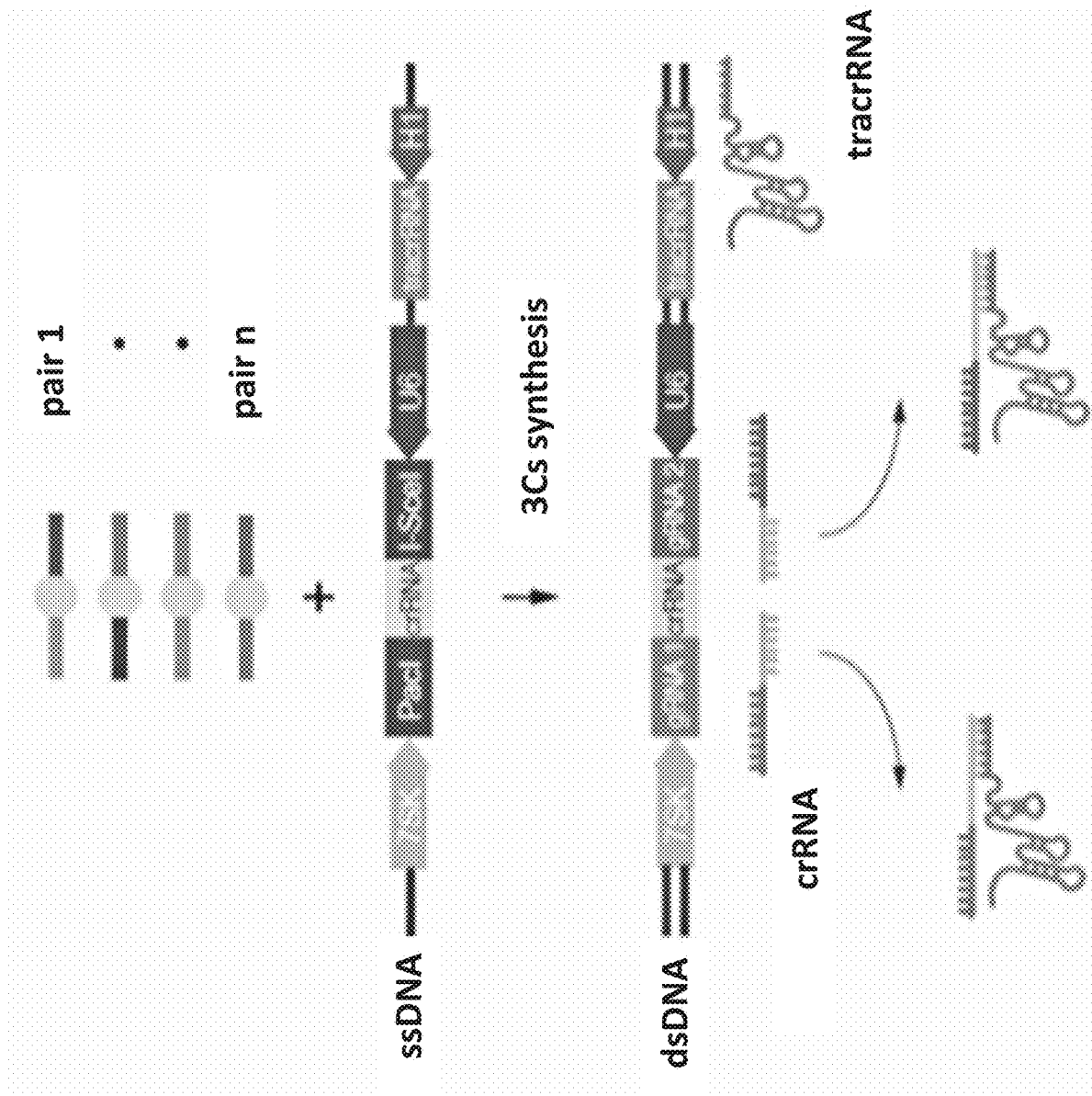
Figure 12:
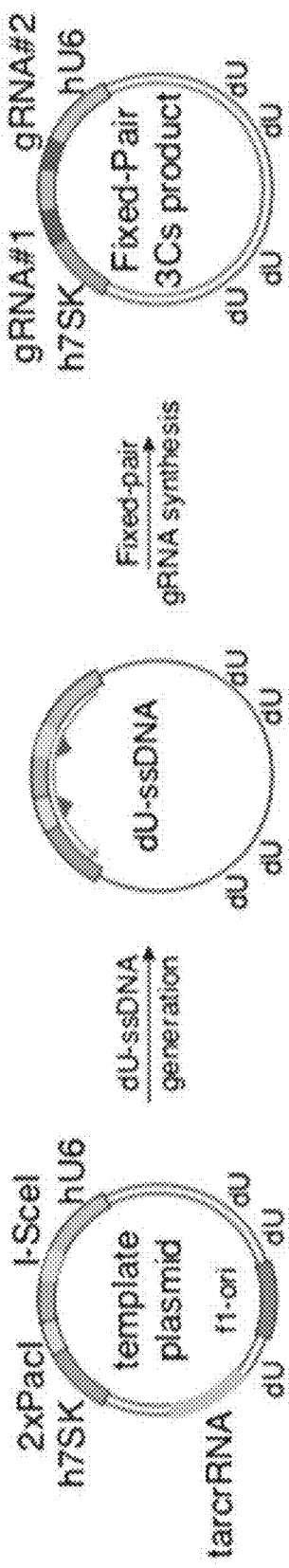
Figure 12:
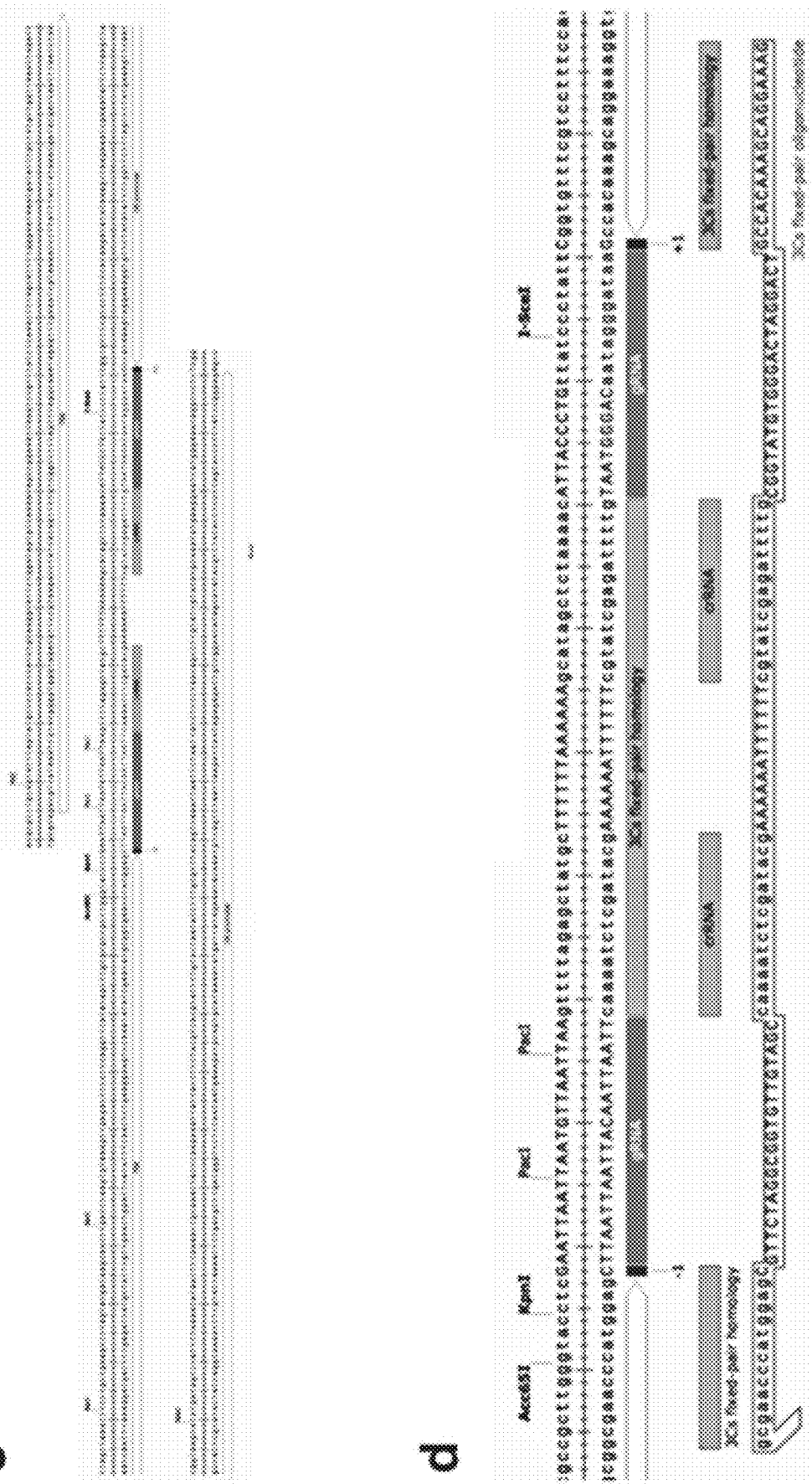

In some other preferred embodiments of the invention crRNA sequence comprises a known "repeat" sequence of a crRNA sequence, such as for example, of a *Streptococcus pyogenes* crRNA sequence (Kooning, E V et al *Curr. Opin. Microbiol.* 37, 67-78 2017, incorporated herein by reference in its entirety). A preferred crRNA sequence of the invention is disclosed for example in FIG. 12 *d*.

In some embodiments it is preferred that within each of the enhanced gRNA expression cassettes the RNA promoter sequence and the gRNA placeholder sequence are in operable linkage, which shall be understood such that when a gRNA sequence is introduced into the placeholder in accordance with the invention, the gRNA sequence is expressed under the control of the RNA promoter sequence.

In preferred embodiments of the invention the enhanced recipient vector therefore comprises the following elements in direct and uninterrupted consecutive order: (i) a first RNA promoter, (ii) a first gRNA placeholder or gRNA sequence, wherein (i) and (ii) are in operable linkage, (iii) a first crRNA (repeat) sequence (iv) optionally a linker, followed by the following elements, each in inverted orientation compared to (i) to (iii): (v) a second crRNA sequence, (vi) a second gRNA placeholder or gRNA sequence, (vii) a second RNA promoter, wherein (vii) and (vi) are in operable linkage.

In some preferred embodiments of the aspect the enhanced mutagenic DNA primer comprising in this order
  i. a first homology region capable of binding to the first enhanced gRNA expression cassette,
  ii. a first predetermined gRNA sequence to be expressed,
  iii. a second homology region capable of binding to the inverted crRNA sequences, and optionally a linker,
  iv. a second predetermined gRNA sequence to be expressed,
  v. a third homology region capable of binding to the second enhanced gRNA expression cassette.

In some embodiments the above method is preferred wherein the method between steps (a) and (c) does not include a step of cloning, preferably cloning referring to a step of nuclease based introduction of double strand breaks followed by ligation—for example after introduction or excision of a part of the vector.

Hence, the problem of the invention is further solved by an recipient enhanced recipient vector, comprising the following elements in direct and uninterrupted consecutive order: (i) a first RNA promoter, (ii) a first gRNA placeholder or gRNA sequence, wherein (i) and (ii) are in operable linkage, (iii) a first crRNA (repeat) sequence (iv) optionally a linker, followed by the following elements, each in inverted orientation compared to (i) to (iii): (v) a second crRNA sequence, (vi) a second gRNA placeholder or gRNA sequence, (vii) a second RNA promoter, wherein (vii) and (vi) are in operable linkage; the enhanced recipient vector further comprising a tracrRNA expression cassette.

All elements and embodiments mentioned in the above other aspects necessary for a successful 3Cs reaction shall be incorporated by reference where applicable or necessary.

Also all applications and uses as described for the other methods and compositions of the invention apply equally as preferred embodiments for this aspect.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

The present invention will now be further described in the following examples with reference to the accompanying figures and sequences, nevertheless, without being limited thereto. In the Figures:

FIG. 1
  a) Combinations of two gRNA-expressing cassettes for the generation of gRNA multiplexed or defined fixed-pair gRNA reagents. Conventional 3Cs-gRNA multiplexing will result in reagents containing all possible combinations of gRNAs targeting either gRNA-expressing cassette (complexity=number of gRNAs for cassette n*number of gRNAs for cassette m, c=n*m). In contrast, predetermining gRNA combinations through 3Cs fixed-pair gRNA synthesis will result in reagents with a complexity of the number of individual defined gRNA combinations (c=n=m).
  b) The two gRNAs of a single fixed-pair of gRNAs can be defined to target DNA in close proximity, leading to the loss of DNA residing between the two gRNA target sequences. As such, fixed-pair gRNA reagents can be utilized to precisely excise DNA sequences.
  c) The two gRNAs of a single fixed-pair of gRNAs can be defined towards the same genetic target (gene, element, noncoding sequence, etc.), thereby drastically improving the efficiency of the desired editing or modification event. Alternatively, the two gRNAs of a single fixed-pair of gRNAs can be defined towards two different genetic targets (gene, element, noncoding sequence, etc.). This enables the precise editing or modification of two defined sequence elements within the same cell.
  d) Fixed-pair gRNA reagents can be used with nuclease active wildtype Cas enzymes (i) or single active-site inactivated Cas enzymes, nickase (ii).
  e) The use of fixed-pair gRNAs is not limited to active Cas enzymes but can be extended to enzymatically-dead Cas enzymes for the inactivation (i), activation (ii), epigenetic modification (iii), or visualization (iv) of genetic elements.

Figure 2:
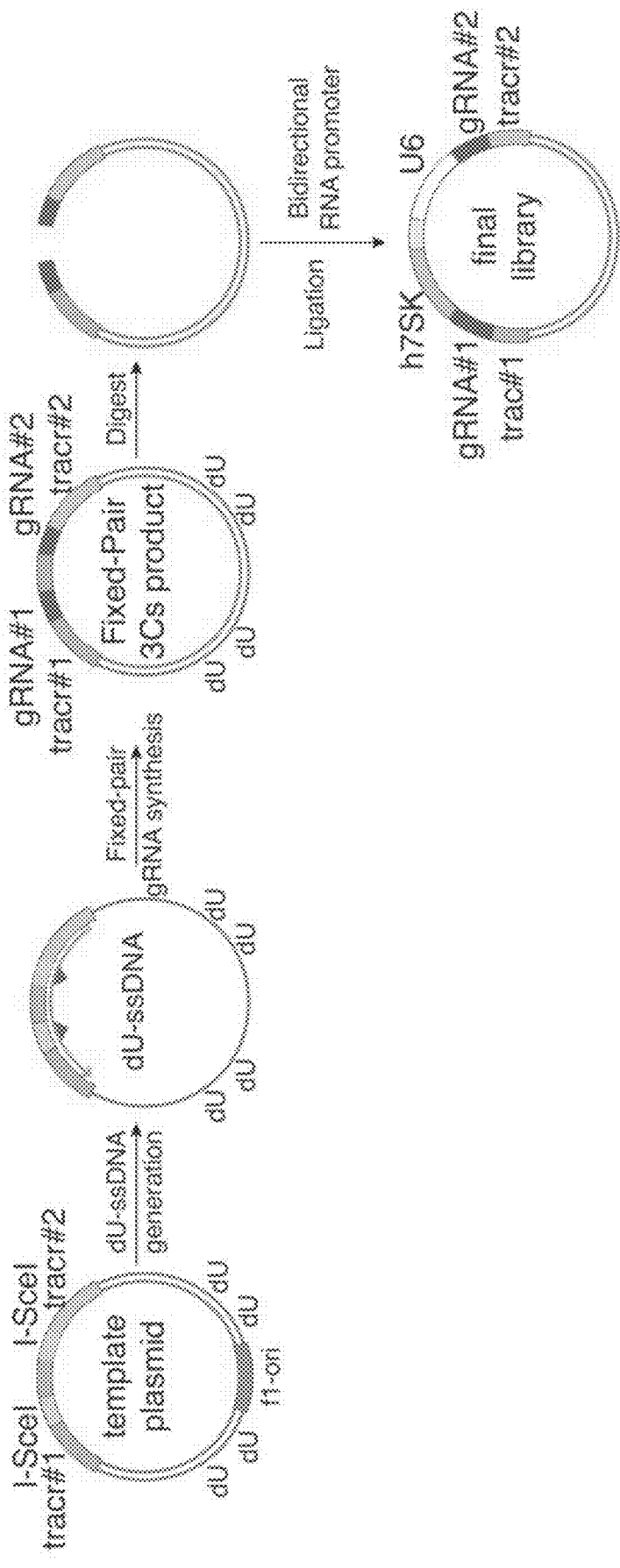
Figure 2:
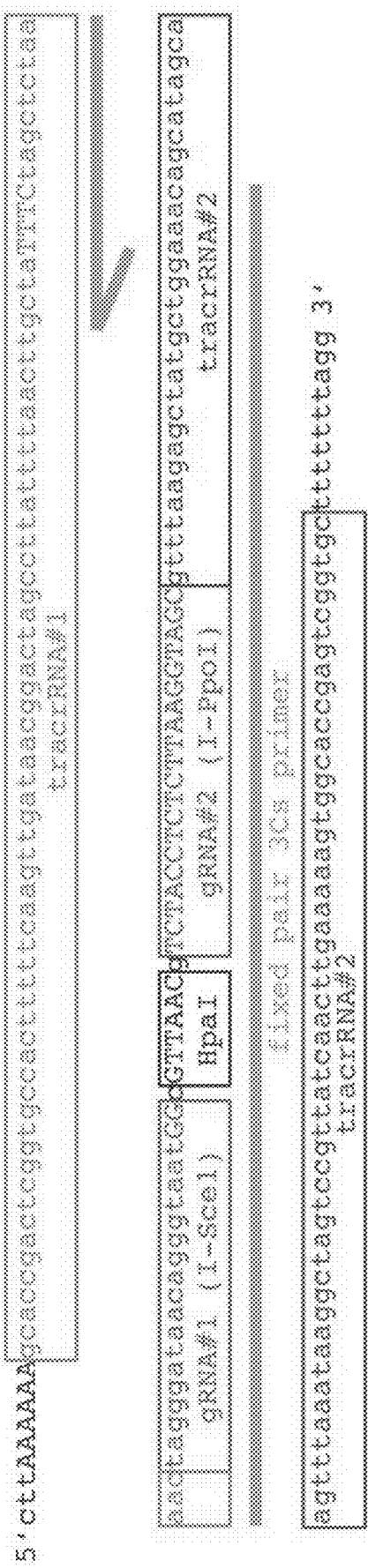
Figure 2:
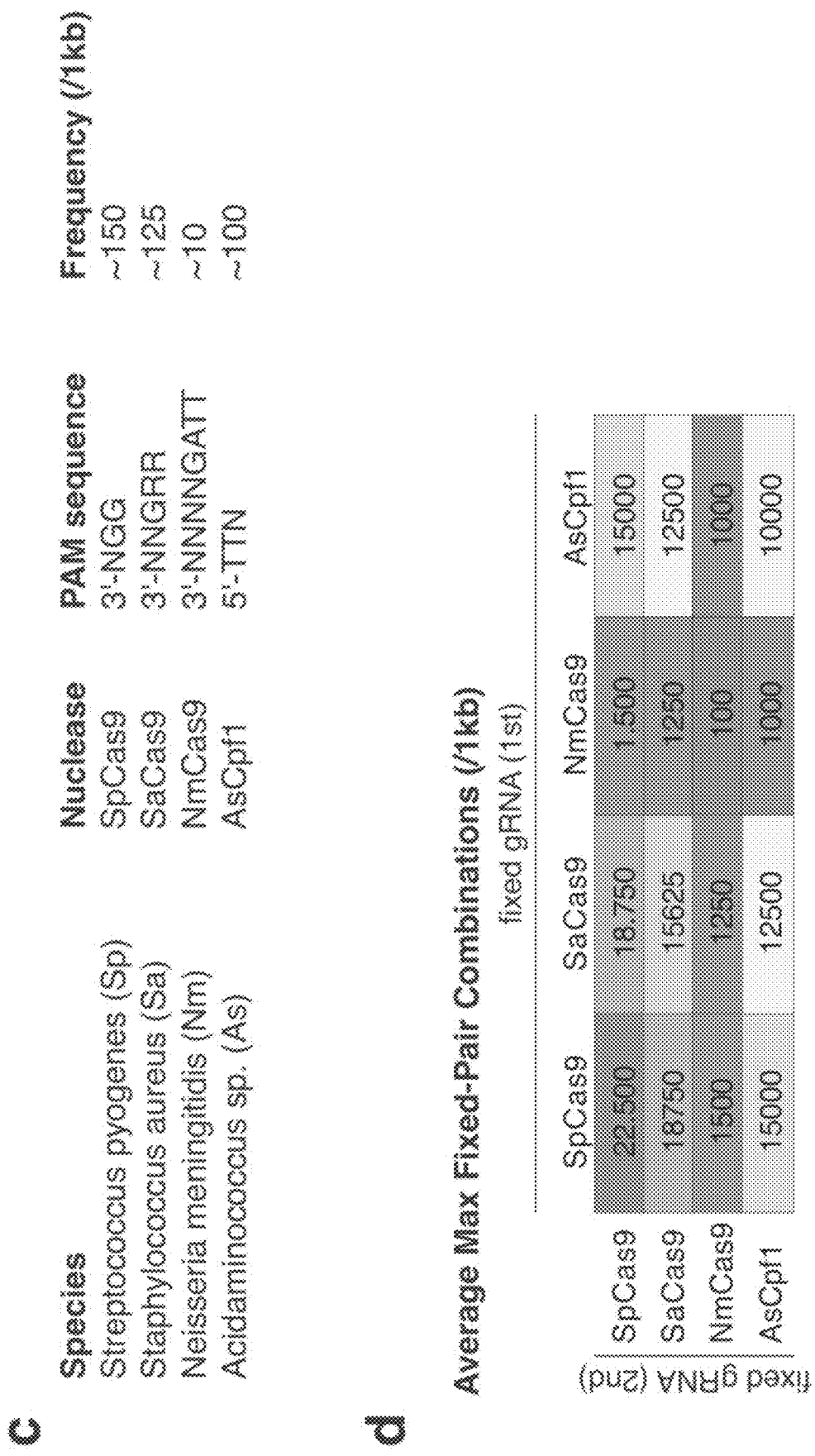

FIG. 2 a) Conceptual workflow for the generation of defined 3Cs fixed-pair gRNA reagents. Two extraverted tracrRNA and gRNA-encoding placeholders (I-SceI sites) are integrated in a template dsDNA plasmid that was amplified in CJ236 bacteria to incorporate randomly deoxy-Uracil. M13K07 superinfection of CJ236 bacteria results in bacteriophage particles containing a ssDNA copy of the template plasmid. A DNA oligonucleotide, encoding for 5' and 3' homology and two defined gRNA sequences, is annealed to the ssDNA and extended and ligated by the activity of T7 DNA polymerase and T4 ligase, respectively. The resulting heteroduplex dsDNA, consisting of template and newly synthesized 3Cs-DNA, is transformed into non-CJ236 bacteria to amplify the new DNA strand and degrade the dU-containg template DNA. The resulting dsDNA of defined gRNA combinations is subsequently opened-up by enzymatic digest in between the two new gRNA sequences and ligated with a bi-directional RNA promoter sequence, resulting in the final defined 3Cs fixed-pair gRNA reagent.

b) Detailed and exemplified sequence view of the oligonucleotide annealing site. Please note the presence of two restriction enzyme recognitions sites that enable a subsequent clean-up step to remove wildtype reminiscent plasmid DNA.

c) Defined 3Cs fixed-pair gRNA combinations are not limited to the use of a single Cas nuclease. Two different tracrRNA sequences can be used, thereby extending the range of target sequences and enabling the usage of combinations of wildtype and enzymatically dead or modified Cas nucleases (FIG. 1d,e).

d) The maximal number of defined fixed-pair gRNA combinations on a given DNA sequence, results from the number of target sequences for tracr #1 multiplied with the number of target sequences for tracr #2. In case of combining SpCas9 target sequences with themselves, the average defined fixed-pair gRNA combinations result from 150*150 (FIG. 2c). If different Cas-enzymes are combined, the number drops down due to the increased PAM selectivity of the Cas enzymes.

FIG. 3 a) Selected sequence elements within the SpCas9 tracrRNA sequence (#1-3) can be adapted to prevent the presence of two highly similar sequences in 3Cs template DNA. Sequence scheme adapted Konermann et al., 2015[14]. The sequence is provided in SEQ ID NO: 7.

b) Comparison of rationally engineered SpCas9 tracrRNA sequences v2 (SEQ ID NO: 9) and v3 (SEQ ID NO: 10) to the wildtype SpCas9 tracrRNA sequence (SEQ ID NO: 8). Blue and red letters indicate rational sequence changes. V2 was previously reported by Chen et al., 2013[16].

FIG. 4 a) On the basis of pLKO.1, the inventors generated 5 3Cs-template dsDNA plasmids containing tracrRNA sequences enabling the following combinations of Cas nucleases: SpCas9:SpCas9 (v1.v2, and v2.v3), SpCas9:SaCas9 (v2.Sa), SpCas9:NmCas9 (v2.Nm) and SpCas9:AsCpf1 (v2.As). All plasmids resulted in the expected band pattern when subjected to analytical restriction enzyme digest and analyzed by gel electrophoresis, confirming correct cloning and 3Cs-template generation.

b) All 3Cs-template dsDNA plasmids were converted to dU-containing ssDNA and resolved by gel electrophoresis revealing high purity of ssDNA.

c) Bacteriophages carrying all five 3Cs-template ssDNA were used to infect XL1 bacteria to convert the ssDNA back to dsDNA and indirectly analyze the quality of 3Cs-template ssDNA. Strikingly, ssDNA corresponding to SpCas9 tracrRNA combinations vi and v2, is subject to severe recombination. In contrast, ssDNA corresponding to all other tracrRNA combinations tested is free of recombination events and, therefore, is suitable as template for fixed-pair 3Cs reactions.

FIG. 5

Two-dimensional folding and structure prediction of different tracrRNA combinations for fixed-pair 3Cs-template design. Single stranded DNA folding predictions are based on Lorenz et al., 2011[13]. Importantly, the structure prediction of tracrRNA combination SpCas9:SpCas9 (SpV1.SpV2) displays a 64 nucleotide long stretch of perfect homology and ssDNA annealing that is absent in predicted structures of all other tracrRNA combinations. The sequences are provided in SEQ ID NO: 8 to 10, and their respective uracil containing RNA.

FIG. 6

Figure 4:
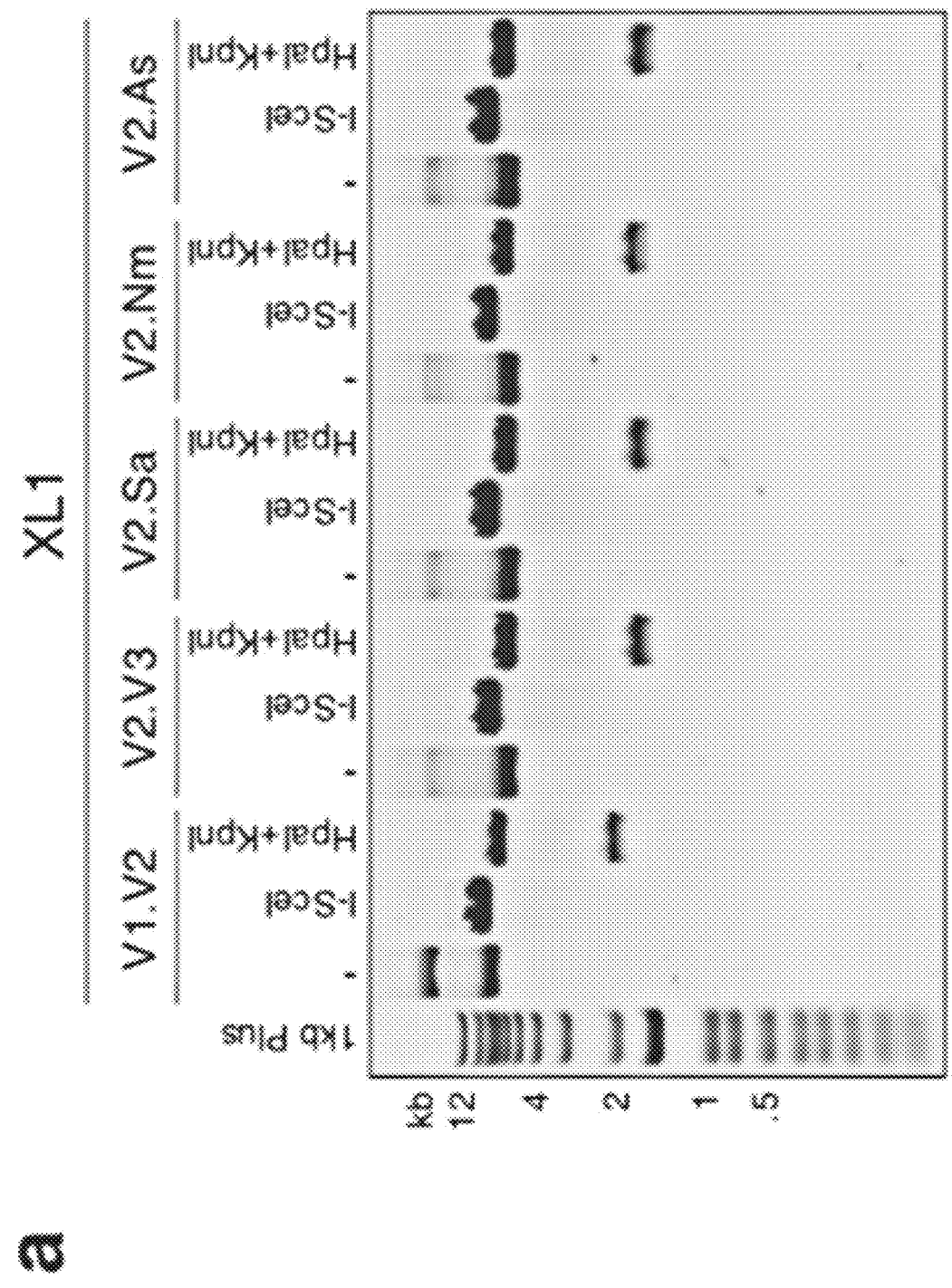
Figure 4:
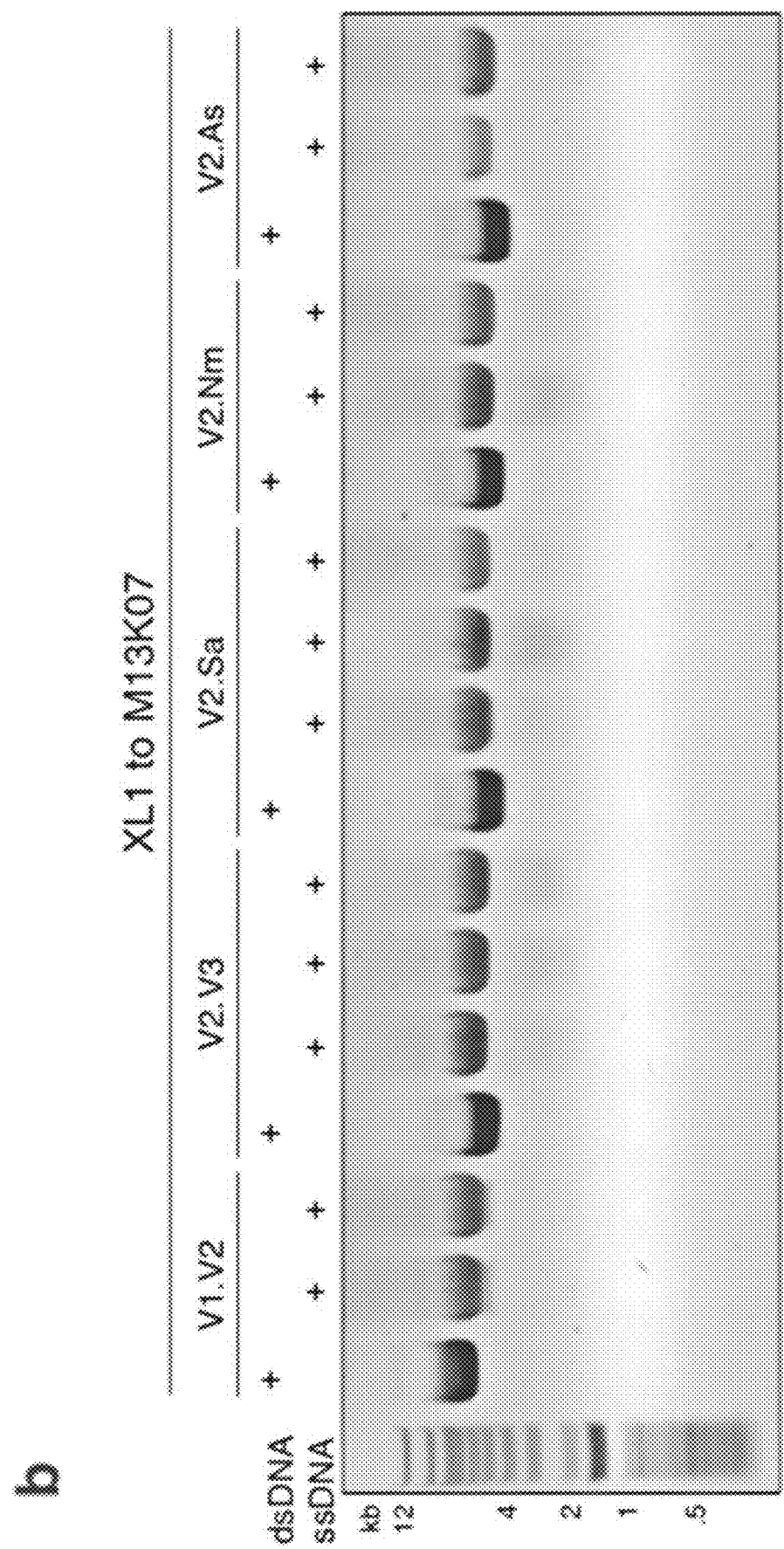
Figure 4:
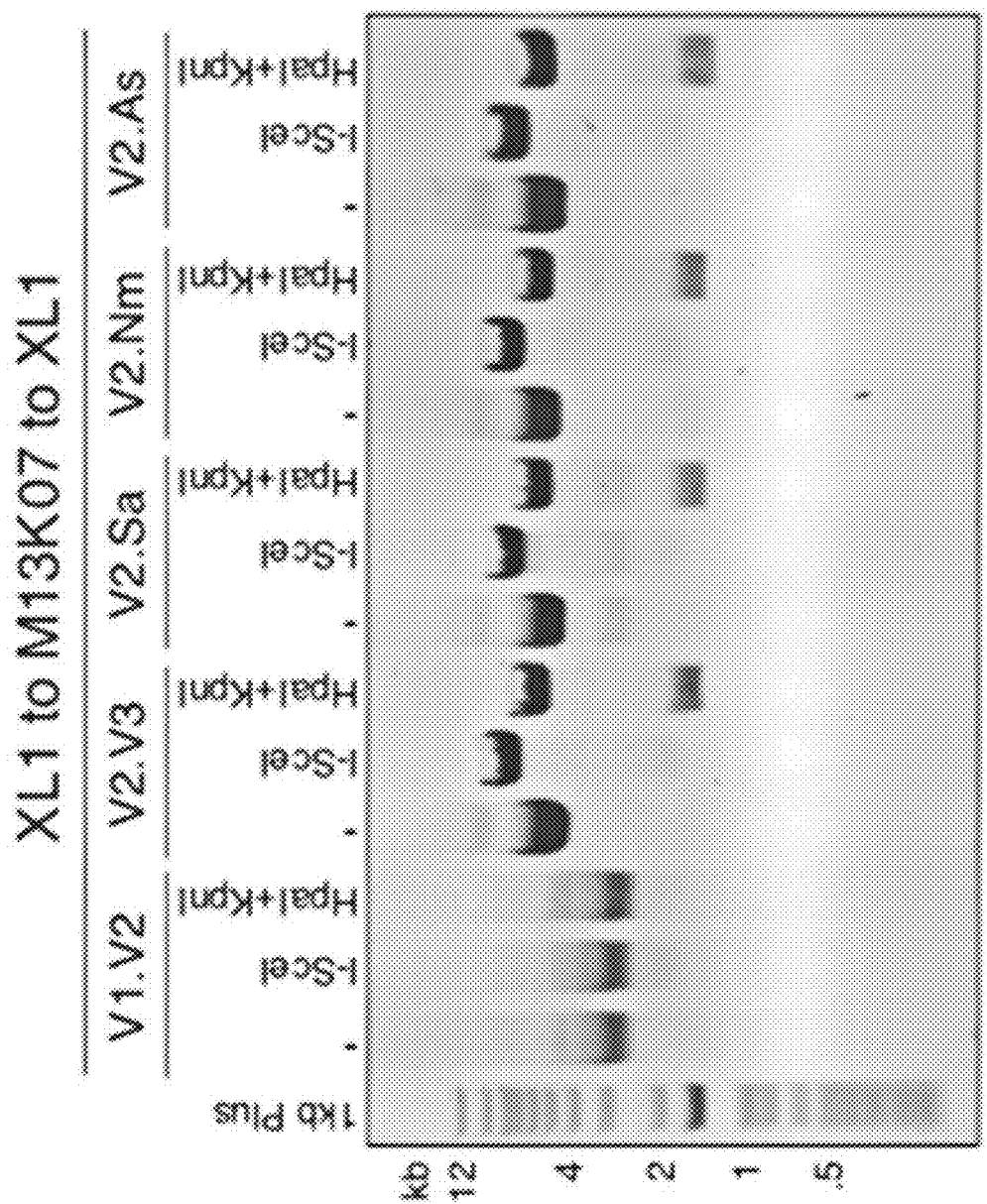

Scheme of tracrRNA combinations and SANGER sequencing of single bacterial clones derived from FIG. 4c. As expected from FIG. 4c, SANGER sequencing of single clones confirmed the recombination event and reveals a complete lack of sequences corresponding to the extraverted tracrRNA and the two gRNA sequences on SpV1.SpV2 fixed-pair template DNA. All other 3Cs fixed-pair template designs showed an error-free sequence.

FIG. 7 a) The genomic locus of the human retinoblastoma protein 1 (RB1) gene, zoomed in to exon 7 until exon 9 and highlighting the gRNA positions used for fixed-pair #1 and #2 in red. After successful DNA excision, a fragment of 219 bp or 207 bp will be lost for fixed-pair #1 or #2, respectively. Please note: gRNAs are designed to target noncoding intronic DNA to minimize coding InDels.

b) Induced Palbociclib (PD, iCdk4) resistance in RPE1 cells after transduction with fixed-pair gRNAs #1 or #2. When compared to control cells (empty, empty lentiviral backbone), cells transduced with fixed-pair #1 or #2 start to proliferate in the presence of the selective Cdk4 inhibitor Palbociclib.

FIG. 8

Single stranded DNA of the five tested tracrRNA combinations were individually combined with a 3Cs fixed-pair DNA oligonucleotide in an over-night 3Cs reaction. 3Cs products were analyzed by gel electrophoresis and compared to dsDNA and ssDNA of the corresponding tracrRNA combination template. Strikingly, all 3Cs reactions indicate successful heteroduplex 3Cs-DNA formation, including the 3Cs reaction performed on the SpCas9 v1.v2 template that the inventors previously demonstrated to contain recombined DNA, suggesting nonspecific DNA oligonucleotide to ssDNA binding in this setting.

FIG. 9

Figure 8:
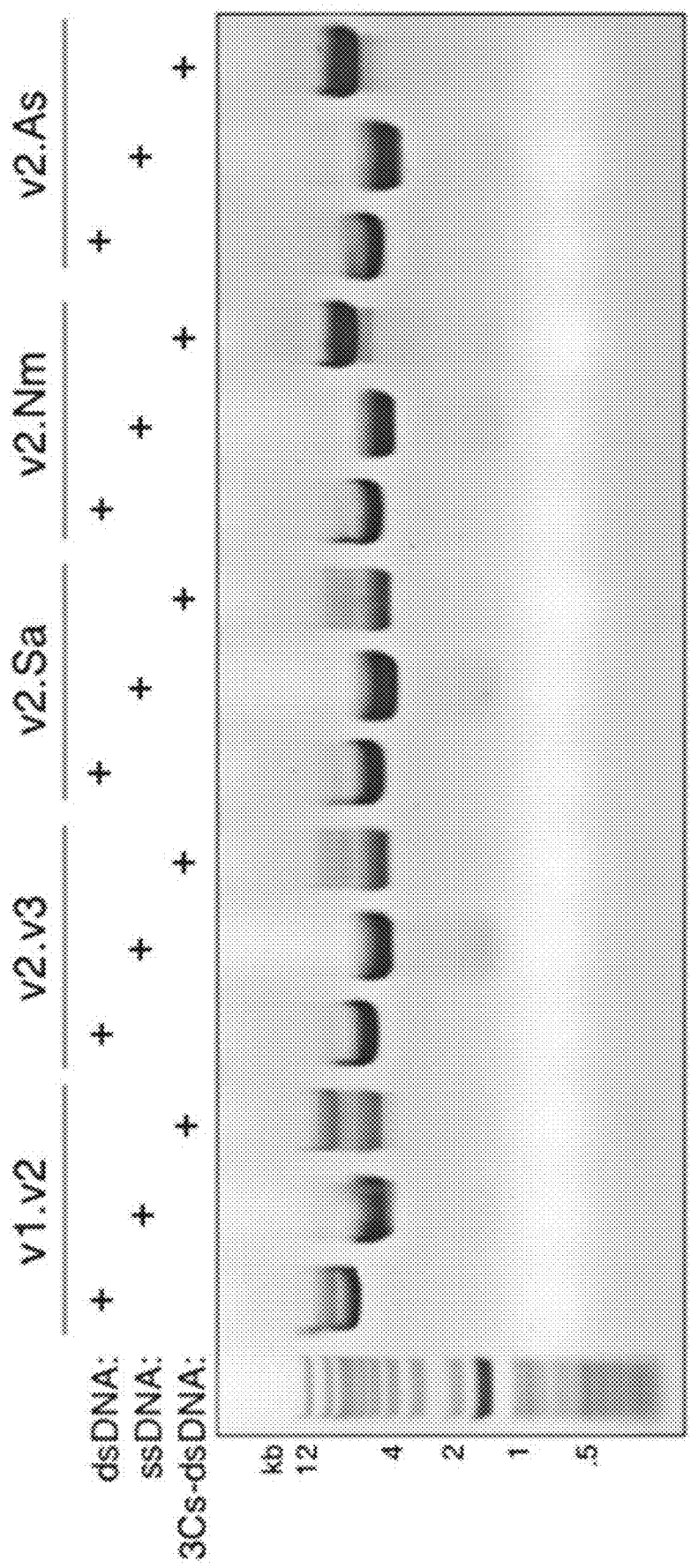

3Cs-DNA of FIG. 8 was transformed in non-CJ236 bacteria for polyclonal DNA amplification. Plasmid DNA of overnight cultures was purified and subjected to analytical restriction enzyme digest. Individual 3Cs-DNA preparations were compared to their corresponding wildtype plasmid DNA control of FIG. 4a. A successful 3Cs reaction will change the I-SceI restriction enzyme site in the 3Cs-template DNA to the defined gRNA sequence. Therefore, enzymatic cleavage with I-SceI will only linearize wildtype 3Cs-DNA. As expected, bacteria transformed with 3Cs-DNA of v1.v2 3Cs-template DNA did not grow well and the resulting DNA did not migrate as wildtype DNA, suggesting that mis-annealing of 3Cs-template DNA and 3Cs oligonucleotide results in DNA species that are non-transformable. In contrast, 3Cs-DNA of all other tracrRNA combinations resulted in non-cleavable DNA, suggesting successful 3cs fixed-pair reactions. Strikingly, the overall quality of the obtained DNA was very high in the absence of any DNA species migrating at unexpected sizes.

FIG. 10

Figure 9:
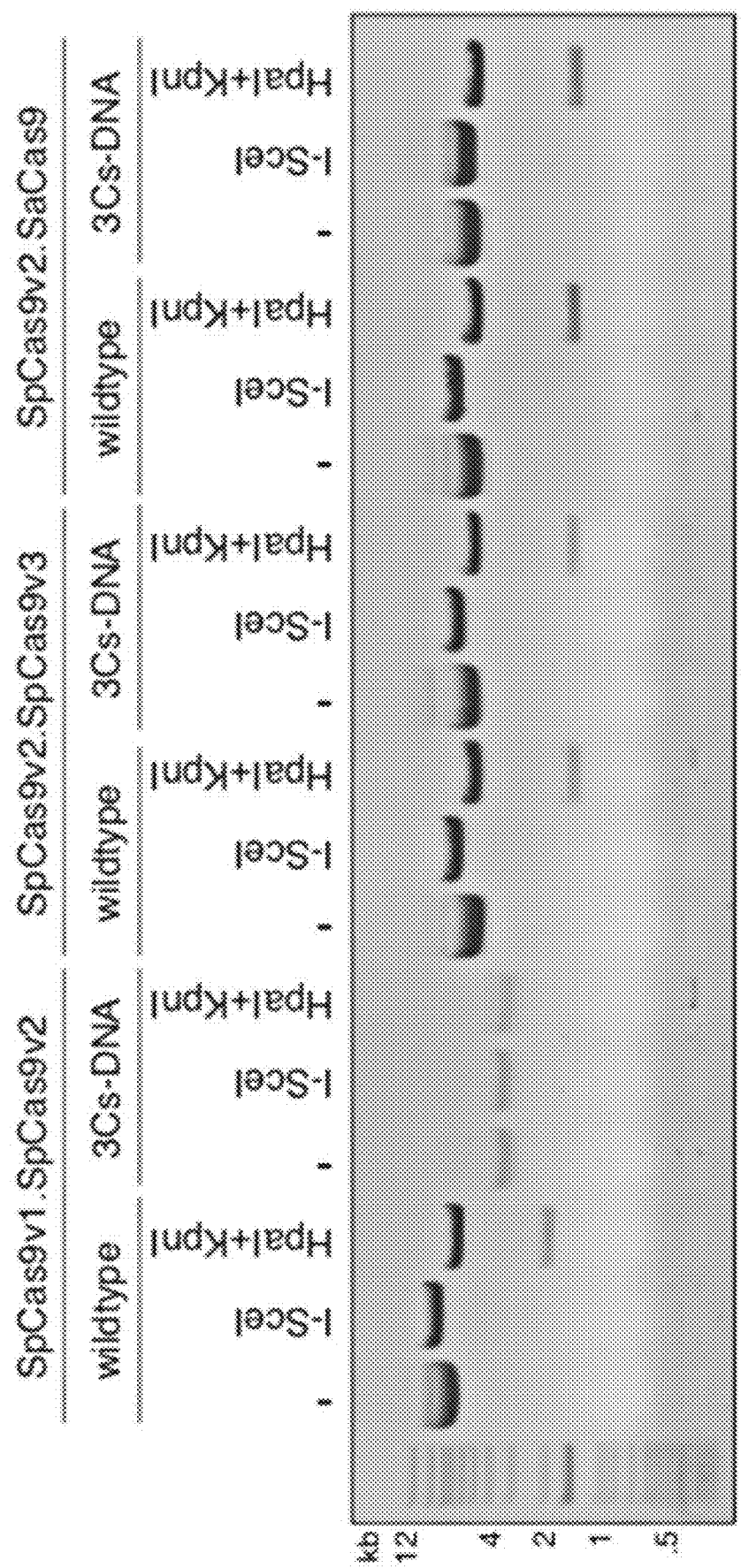
Figure 9:
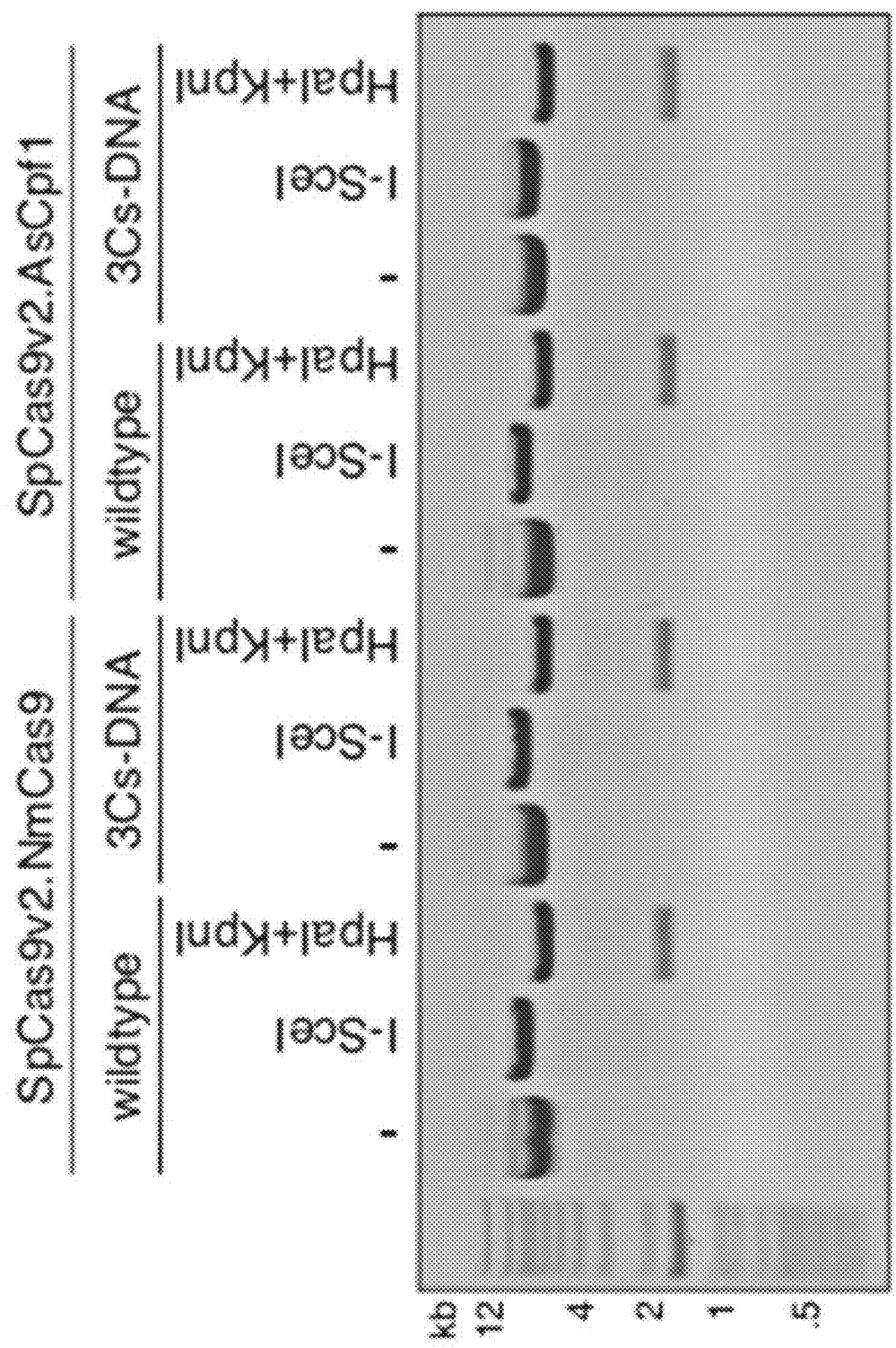

Similar to FIG. 9, 3Cs-DNA of FIG. 8 was transformed in non-CJ236 bacteria but streaked out on LB agar plates from which single bacterial colonies were amplified and their DNA analyzed by SANGER sequencing. When compared to the respective wildtype (WT) SANGER sequencing result, the inventors were able to identify for all tracrRNA combinations tested the correct RB1 fixed-pair gRNA sequences. This demonstrates that the inventors have successfully generated a new technology, based on the previously described 3Cs-technology, that enables the generation of defined fixed-pair gRNA reagents.

FIG. 11

As demonstrated above, the 3Cs fixed-pair technology enables the predetermination of two sequences in a single or pooled manner and therefor represents the first-of-its-kind technological solution. However, several adaptations of the 3Cs fixed-pair technology are logical consequences. As such, e.g. the combination of a single fixed-pair cassette with a single gRNA-expressing cassette on the same plasmid should be possible (a). Also, a single fixed-pair cassette can be combined with two separate gRNA-expressing cassettes, enabling a combination of fixed-pair gRNAs with gRNA multiplexing (b). Furthermore, it is technically feasible to design 3Cs-templates in which two fixed-pair gRNA cassettes are combined, enabling fixed-pair multiplexing.

FIG. 12

Enhanced 3Cs fixed-pair gRNAs. a) Scheme illustrating the logic of separating crispr (cr) RNA from tracrRNA in the process of fixed-pair gRNA combination generation. Briefly, oligonucleotides encoding for two predefined gRNA combinations are synthesized and pooled with ssDNA of template DNA to perform a 3Cs synthesis reaction. The resulting dsDNA product lead to the expression of two separate crRNA sequences, that anneal to the tracrRNA (co-expressed from same plasmid) to form, together with SpCas9, a functional ribonucleotide-complex. b) General workflow of 3Cs fixed-pair reactions and template design rules for ssDNA. c) Fixed-pair template DNA design. Highlighted are RNA promoter, gRNA and crRNA sequences. d) Design and annealing principle of 3Cs fixed-pair gRNA oligonucleotides.

FIG. 13 a) Two CJ236 clones were subject to ssDNA generation of our enhanced fixed-pair template DNA. SsDNA migrates faster than dsDNA. b) Agarose gel-electrophoresis of 3Cs products after fixed-pair 3Cs synthesis with individual primer pairs identifies 3Cs reaction products. c-d) Quality control step (P1) of amplified dsDNA 3Cs fixed-pair products, analyzed by PacI and I-SceI restriction enzyme digest. No cutting indicates successful integration of new sequences. Digested products of P1 are re-amplified (P2) and analyzed by restriction enzyme digest again and reveal the absence of wildtype remnants. e) SANGER sequencing of P1 and P2 of 3Cs DNA derived from (c). 8 nucleotides are identified to be changed (highlighted by arrows). Importantly, already at the level of P1, sufficient randomization at these 8 nucleotide positions is identified, while at the level of P2 a complete randomization has occurred.

FIG. 14

Agarose gel-electrophoresis of amplified dsDNA of 3Cs synthesis products. Different ratios of ssDNA to oligonucleotide and total DNA amounts are tested to have an influence on quality of P1. No apparent bias towards a single ratio or amount was identified (all tested conditions worked), revealing a high performance of 3Cs fixed-pair reactions.

Figure 15:
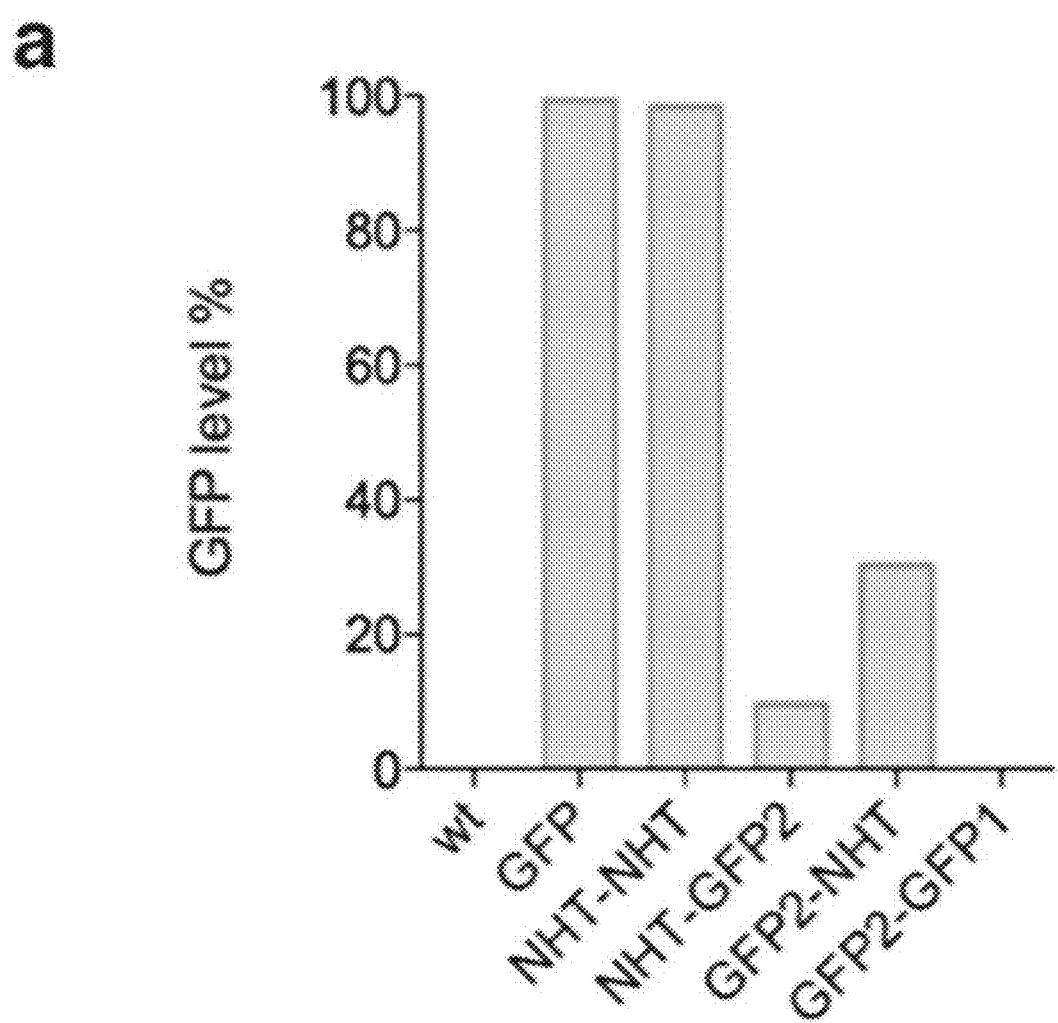
Figure 15:
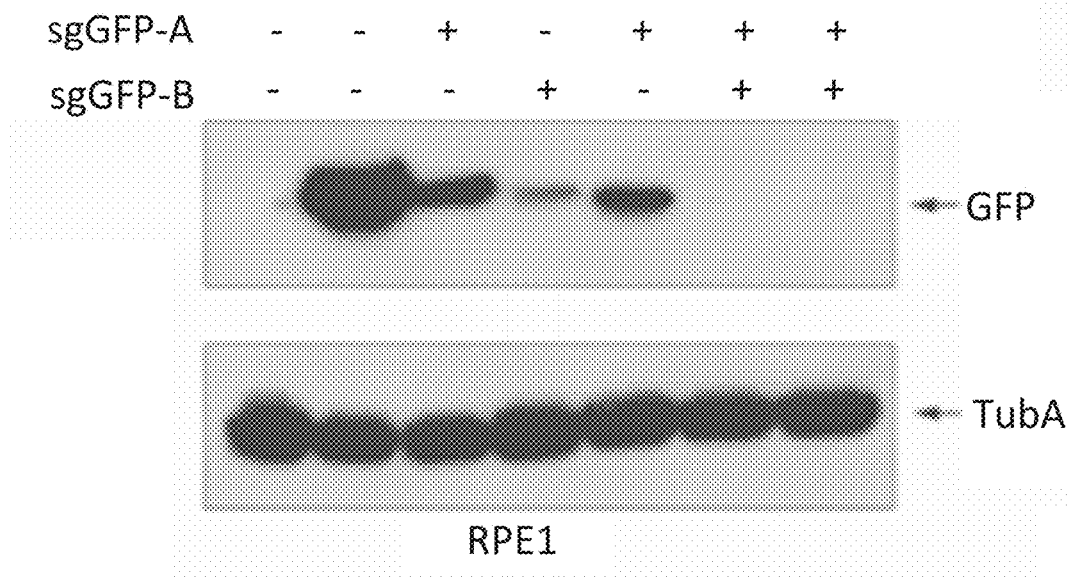
Figure 15:
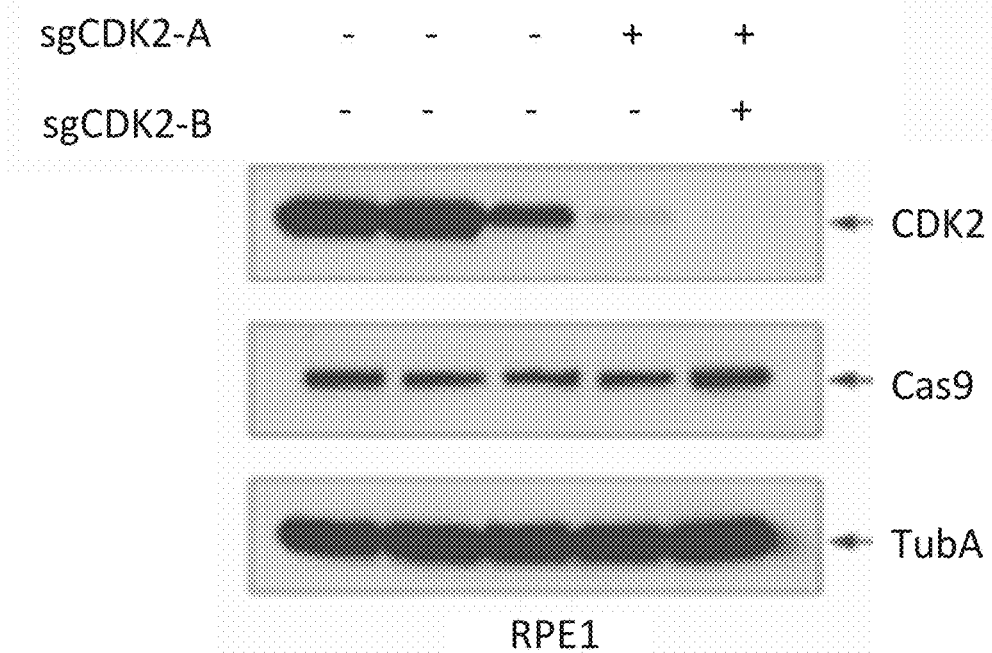

FIG. 15. Cell functionality of 3Cs fixed-pair gRNA reagents. a) Fixed-pair constructs derived from FIG. 13b, were subject to the generation of lentiviral particles and used to transduce GFP-positive RPE1 cells. GFP depletion was analyzed by FACS. As reported previously, single gRNAs robustly reduce GFP-positive cells, while a fixed-pair combination of GFP-targeting gRNAs completely abolishes the population of GFP-positive cells. b) Immunoblot analysis of cells derived from (a), confirming the loss of GFP fluorescence by FACS is due to the loss of GFP protein. c) Similar to the fixed-pair targeting of GFP, 3Cs fixed-pair constructs targeting Cdk2 are used either single or in combination and reveal an improved depletion of Cdk2 when two functional gRNAs are used as fixed-pair combination. This demonstrates that two gRNAs in the form of 3Cs fixed-pair gRNAs have an improved on-target activity when compared to either of these gRNAs individually.

TABLE 2

Sequences of the Invention

| SEQ ID NO: | Sequence | Description |
| --- | --- | --- |
| 1 | GTttccagcatagctcttaaacCCGTCCTCGAAGTTCATCAC-CGTTAACgGTCGCCCTCGAACTTCACCTgttttagagctaG-AAAtagcaa | SpV1-SpV2-R |
| 2 | cttgctcTAGCTCTAAAACtgcgattttctctcatacaaCGTTAACGgct-gaatgagaaagtaaaagGTTTAAGAGCTATGCTGG | SpV2-SpV3-R: |
| 3 | ctgtttccagagtactaaaactgcgattttctctcatacaaCGTTAACGgct-gaatgagaaagtaaaagGTTTAAGAGCTATGCTGG | SpV2-SaV1-R |
| 4 | agaaagggagctacaacatggactttgcccataagtaCGTTAACGgctgaat-gagaaagtaaaagGTTTAAGAGCTATGCTGG | SpV2-NmV1-R |

TABLE 2-continued

Sequences of the Invention

| SEQ ID NO: | Sequence | Description |
|---|---|---|
| 5 | ttcgaccgacaattaaaaaagcaactgctgaatgagaaagatctacaagagtag-aaattaCGTTAACGgctgaatgagaaagtaaaagGTT-TAAGAGCTATGCTGG | SpV2-As-R |
| 6 | ATTCATAATGATAGTAGGAGGCTTGGTAGG | pLKO-1-Seq-F |
| 7 | NNNNNNNNNNNNNNNNNNNNGUUUUAGAGCUAGAAAUAGCAAGUUAAAAUAAGGCUAGUCCGUUAUCAACUUGAAAAAGUGGCACCGAGUCGGUGCUU | wt RNA |
| 8 | GTTTTAGAGCTAGAAATAgcaagttaaaataaggctagtccgttatca-ACTTGAAAAAGTGGCACCGAGTCGGTGC | tracrRNA wt (V1) |
| 9 | GTTTTAGAGCTAGGCTGGAAACAGCATAGCAAGTTTAAATAAGGCTAGTCCGTTATCAACTTGAAAAAGTGGCACCGAGTCGGTGC | tracrRNA V2 |
| 10 | GTTTTAGAGCTAGAGCAAGCTCTAGCAAGTTAAATAAGGCTAGTCCGAATAGAACTTCCACAAGTGGCAGGCAGTGCCTGC | tracrRNA V3 |
| 11 | GAAAGGACGAAACACCGTCAGGATCAGGGTG-TATGGCgttttagagctatgcTTTTTTAAAAAAgcatagctctaaaac-CTCGCACCCATATAGCAAGCCgaggtacccaagcg | NHT-NHT |
| 12 | GAAAGGACGAAACACCGTCAGGATCAGGGTG-TATGGCgttttagagctatgcTTTTTTAAAAAAgcatagctctaaaac-CGATGTTGTGGCGGATCTTGCgaggtacccaagcg | GFP2-NHT |
| 13 | GAAAGGACGAAACACCGGAAGGG-CATCGACTTCAAGGgttttagagctatgcTTTTTTAAAAAA-gcatagctctaaaacGCATGTTGTGGCGGATCTTGCgaggtacccaa-gcg | NHT-GFP2 |
| 14 | GAAAGGACGAAACACCGGAAGGG-CATCGACTTCAAGGgttttagagctatgcTTTTTTAAAAAA-gcatagctctaaaacCGATGTTGTGGCGGATCTTGCgaggtacccaa-gcg | GFP1-GFP2 |
| 15 | GAAAGGACGAAACACCGAAGCAGAGAGATCTCTCGGAGTTTAGAGACGCTCGTCTCTAAACCCATCAGGCGGAAGCTTTTTCGAGGTACCCAAGCG | NHT-Cdk2 |
| 16 | GAAAGGACGAAACACCGAAAAAGCTTCCGCCTGATGGGTTTAGAGACGCTCGTCTCTAAACAGATGCGGTTTTCCTCGCAGCGAGGTACCCAAGCG | Cdc27-NHT |
| 17 | GAAAGGACGAAACACCGACAGGTTGCCAGTAAAAACAGTTTAGAGACGCTCGTCTCTAAACCTCCCGTCAACTTGTTTCTGCGAGGTACCCAAGCG | Cdc27-Cdk2 |

EXAMPLES

Comparative Example: Covalently Closed Circular Synthesized Mutated CRISPR/Cas9 Plasmids While conventional site-directed mutagenesis does not work efficiently on large retroviral elements-containing plasmids, it was anticipated that T7 DNA polymerase and T4 DNA ligase-mediated 5' oligonucleotide extension on the basis of ssDNA would be an efficient approach to generate high quality and unbiased gRNA-libraries (FIG. 12A). To this end, dut–/ung–, F-factor containing, K12 *Escherichia coli* CJ236 bacteria were transformed with the most widely used f1-origin (f1-ori)-containing CRISPR/Cas9 plasmids pLentiGuide and pLentiCRISPRv2. In contrast to conventional K12 *E. coli* strains, CJ236 bacteria tolerate the presence of deoxyuridine in genomic and plasmid DNA due to the lack of the enzymes dUTPase (dut–) and uracil glycosylase (ung–). Subsequent super infection of transformed CJ236 with M13K07 bacteriophage allows the production of bacteriophage particles that package a deoxyuridine containing ssDNA (dU-ssDNA) template of pLentiGuide and pLentiCRISPRv2. In a next step, the dU-ssDNA is purified from the precipitated bacteriophage particles (FIG. 12B). In general, this approach can be applied to any plasmid that encodes an f1-ori.

Figure 13:
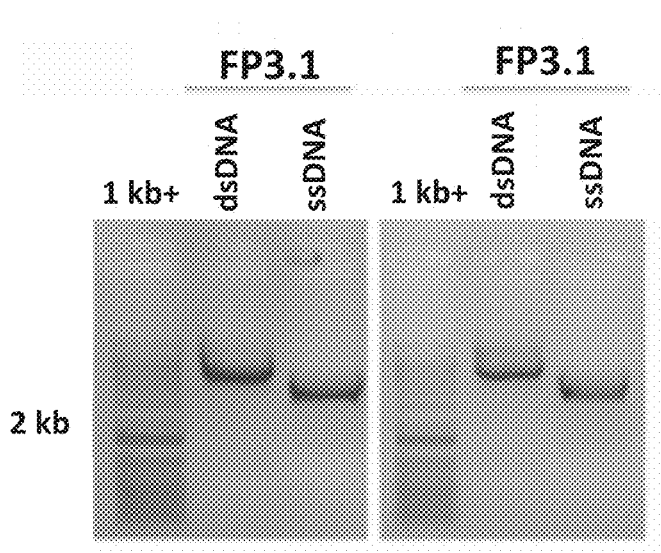
Figure 13:
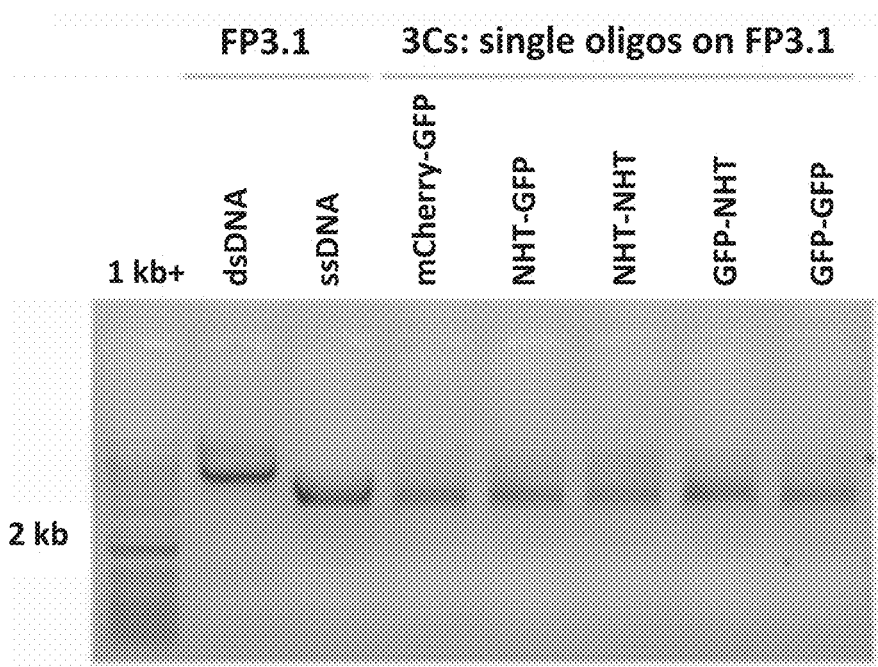
Figure 13:
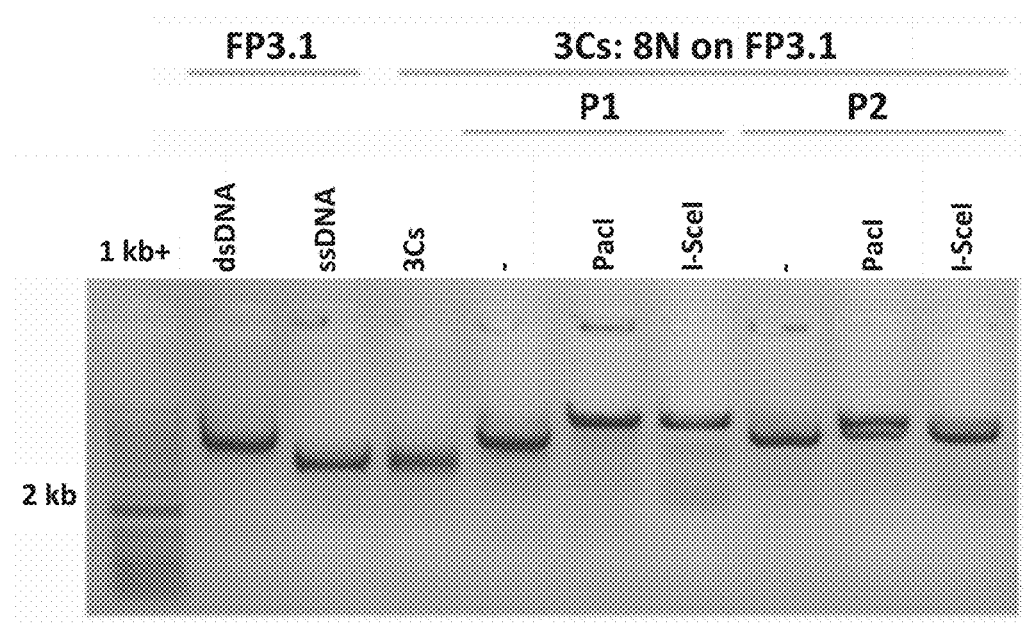
Figure 13:
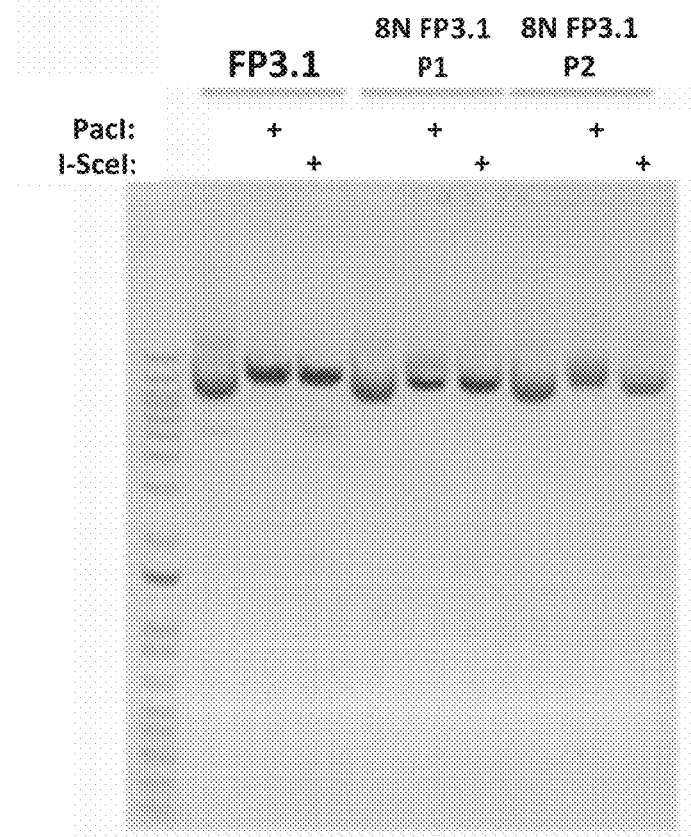
Figure 13:
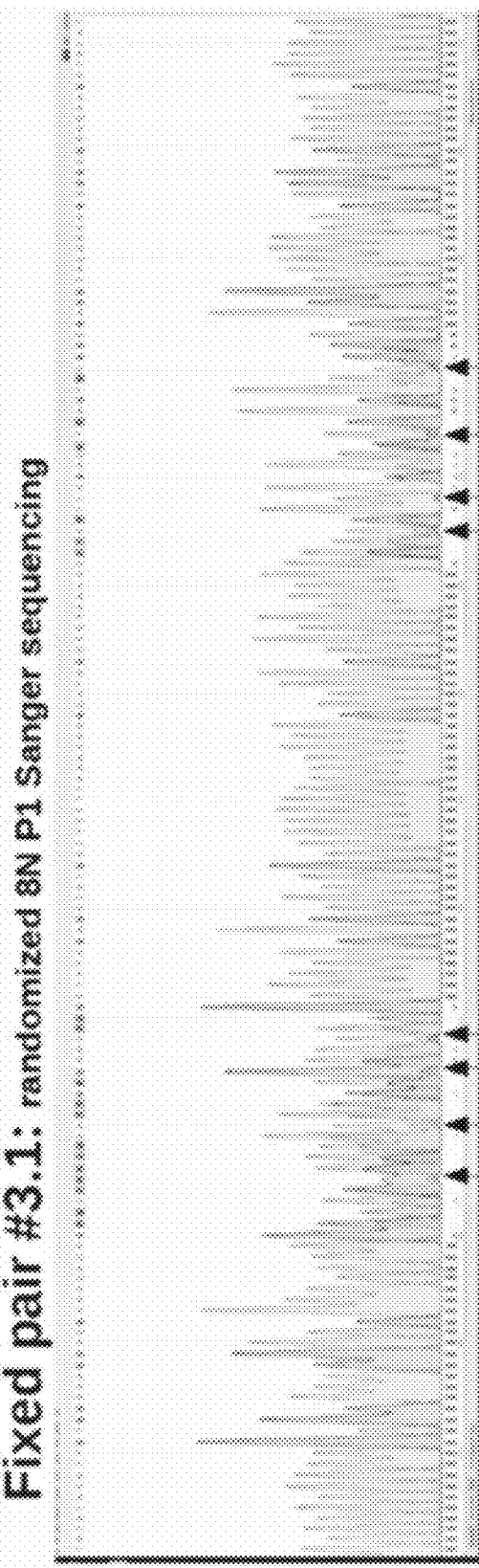
Figure 13:
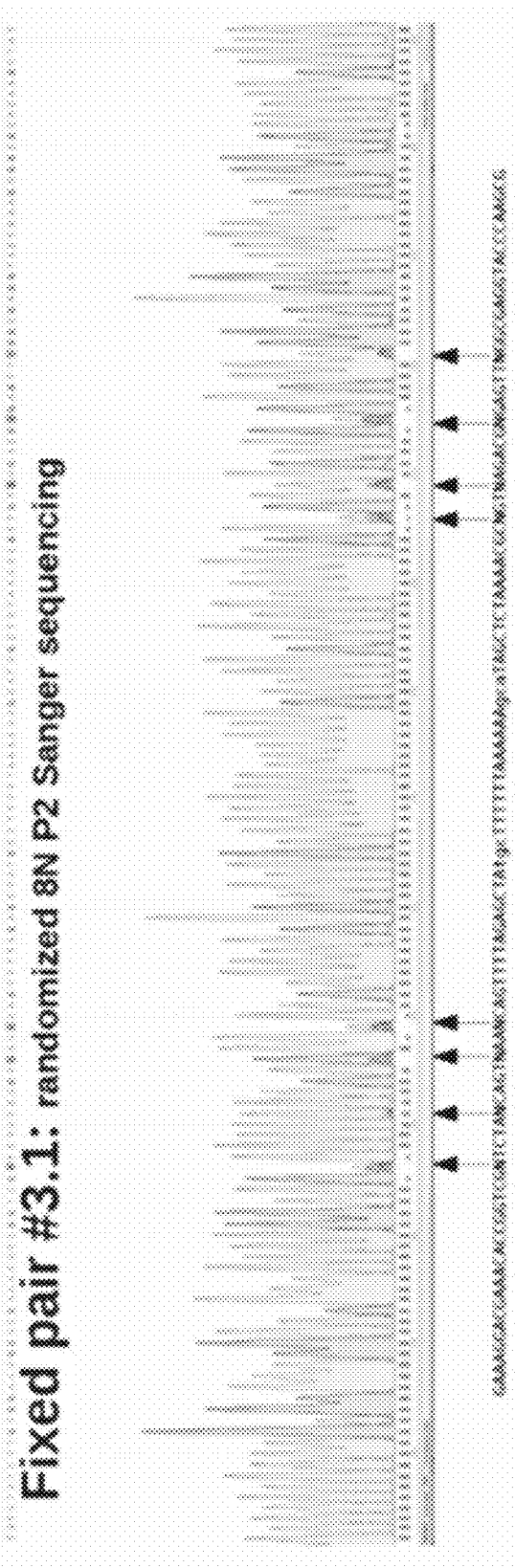

To successfully generate heteroduplexed, covalently closed circular synthesized dsDNA (3Cs-dsDNA) from dU-ssDNA templates, the optimal primer/homology length by comparing 10, 13, 15, and 18 nucleotides (nts) of 5' and 3' homology in a 2 hr in vitro 3Cs reaction was tested (FIG. 13A). The dU-CCC-dsDNA reaction products were resolved by gel-electrophoresis and the typical three-band pattern of heteroduplex dsDNA reactions (33, 34) was identified. The optimal ratio between correctly extended, nicked and strand-displaced 3Cs products was achieved with 15 nts of primer homology (FIG. 13A), hence, the inventors used this length for all subsequent reactions.

Next, the inventors tested this protocol for the generation of in cell active gRNAs that target the enhanced green fluorescent protein (eGFP) gene. Six gRNA sequences were designed using the rule set 2 (RS2) algorithm and cloned using a 3Cs reaction into pLentiGuide and pLentiCRISPRv2 containing a non-human targeting (NHT) control sequence under the control of the U6 promoter and followed by the gRNA scaffold DNA sequence responsible for binding to Cas9 (FIG. 2B) (32). The resulting heteroduplex dU-CCC-dsDNA was used to transform XL1 bacteria to determine the ratio of correctly mutated to wild type (NHT)-containing sequences. The inventors individually sequenced 20 clones and determined that 81% of pLentiGuide and 82% of plentiCRISPRv2 were modified with GFP targeting gRNAs (FIG. 13C,D). Addition of uridine to the M13K07 culture media significantly reduced the wild type rate to about 12% indicating that the occurrence of unmodified plasmid is most likely due to insufficient incorporation of dU into the dU-ssDNA template (FIG. 13E).

Importantly, the inventors were able to identify several copies of all 6 eGFP-targeting gRNA sequences (FIG. 13D), even though the inventors sequenced only 20 individual clones suggesting that the highly efficient protocol is suitable for library constructions.

Figure 14:
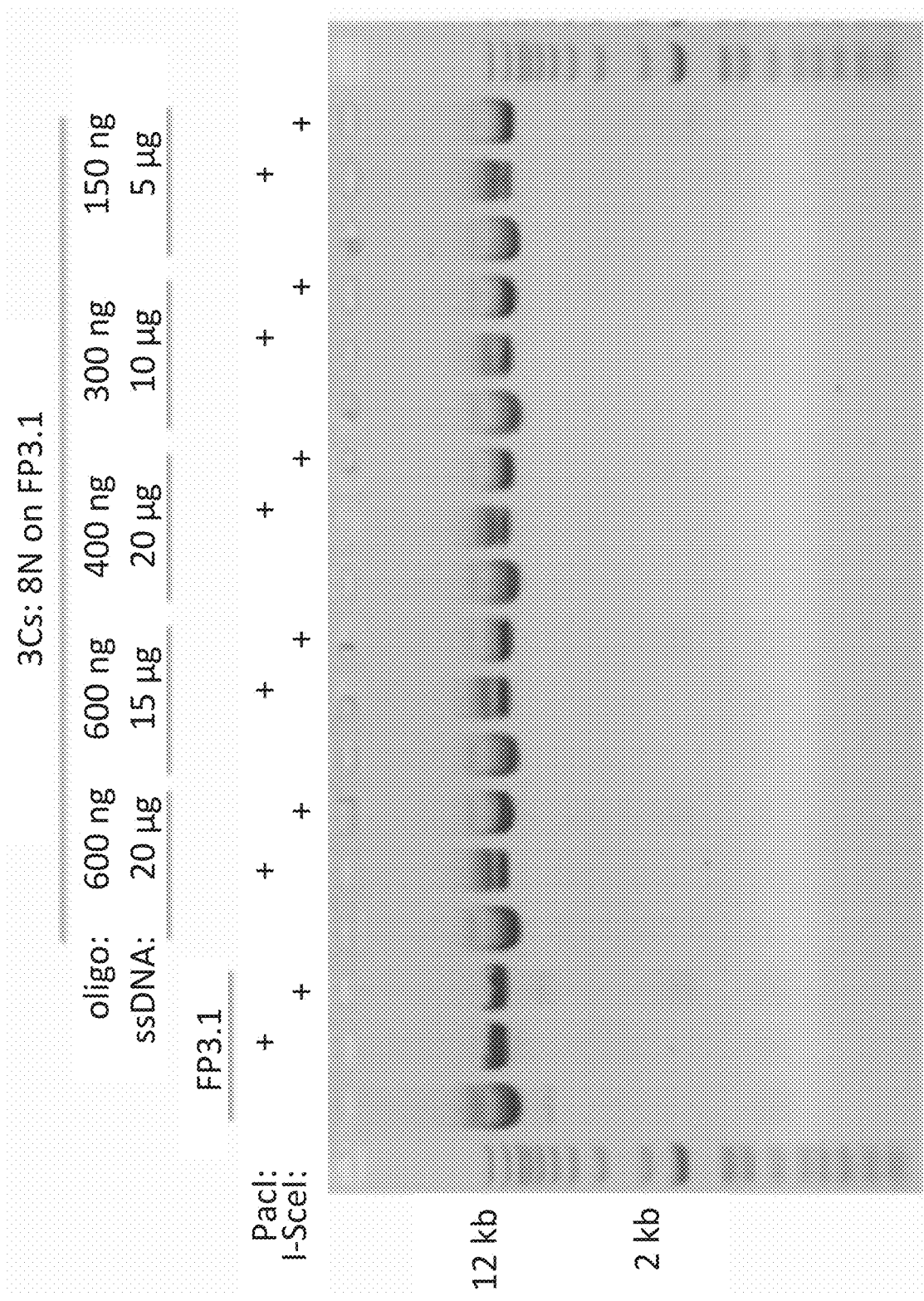

To test in cell functionality of the eGFP-targeting gRNA constructs, infectious lentiviral particles were generated and used to transduce eGFP-positive human telomerase-immortalized retina pigmented epithelial (RPE1) cells. After 7 days without any selective pressure, the presence of eGFP-positive and negative cells was analyzed by flow-cytometry. The reduction of green fluorescence using the lentiviral 3Cs-gRNA constructs was very potent, while the control plasmid had no effect on eGFP fluorescence (FIG. 14). Interestingly, the inventors observed a dose-dependent fluorescence reduction, indicating that lentiviral transduction of RPE1 cells is equally efficient as with conventionally generated lentiviral CRISPR/Cas particles (FIG. 14). Hence, covalently closed circular synthesized CRISPR/Cas gRNAs can be rapidly generated using the newly established 3C approach and are fully functional in cells.

Example 1: A 3Cs Strategy Towards Fixed-Paired CRISPR/Cas gRNAs

In order to generate gRNA combinations or fixed-pairs of gRNAs, the inventors designed a 3Cs-strategy based on the previously invented 3Cs-technology (FIG. 2a). To do so, the inventors in silico designed a template plasmid on the basis of pLKO.1 in which the shRNA-expressing cassette (RNA promoter and shRNA cloning site) was replaced by two tracrRNAs in opposite directions that are essential for RNA-binding to Cas nuclease. The extraverted tracrRNAs are separated by two restriction site-encoding gRNA placeholders (FIG. 2a,b). The inventors cloned and amplified this plasmid in CJ236 bacteria and converted it to single stranded circular dU-DNA (dU-ssDNA) through amplification and purification of bacteriophage M13K07 particles. The resulting circular dU-ssDNA is then annealed with a DNA oligonucleotide featuring sufficient 5' and 3' homology to the extraverted tracrRNA sequences (tracr #1 and tracr #2) and containing the two defined bidirectional gRNA sequences (FIG. 2a,b). The annealed DNA oligonucleotide is then extended and ligated to its own tail by the activity of T7 polymerase and T4 ligase, respectively, generating a heteroduplex DNA (3Cs-DNA) consisting of template and newly synthesized DNA strand. 3Cs-DNA is then transformed into non-CJ236 bacteria for the selective degradation of dU-containing DNA and the amplification of newly synthesized plasmid DNA. Purified non-dU containing plasmid DNA is purified and subject to a clean-up step (restriction enzyme digest) to remove wildtype reminiscent plasmids. To enable gRNA expression, a bidirectional RNA promoter (composed of two non-homologous sequences, e.g. hU6, h7SK, H1, etc.) is cloned in between the two defined gRNA sequences by utilizing a restriction enzyme cleavage site (blunt or sticky cloning) resulting in the final CRISPR/Cas gRNA library of defined ("fixed-pair") gRNA combinations (FIG. 2a).

Since the initial description of the CRSIPR/Cas system and the characterization of the most widely used Cas enzyme SpCas9[3,4], many additional Cas nucleases have been described and functionally characterized. The inventors selected several commonly used Cas enzymes (SpCas9, SaCas9, NmCas9, and AsCpf1) and estimated their average target site occurrence in 1.000 random nucleotides (GC-content of 50%) on the basis of their individual PAM sequence selectivity (FIG. 2c)[3-7]. As previously reported, SpCas9 has the highest target site occurrence with roughly 150 target sites per kilobase DNA, followed by SaCas9 with 125, NmCas9 with 10 and AsCpf1 with about 100 target sites per kilobase (FIG. 2c). Theoretically, fixed-pair gRNA combinations can be generated not only on the basis of the same tracrRNA (utilizing the same Cas enzyme), but also in combination with different tracrRNA molecules (relying on different Cas enzymes), expanding the range of targets and their specificity. As such, combinations of SpCas9 with SaCas9 or AsCpf1 have the broadest range of targets with an average fixed-pair target number of about 20.000 gRNA combinations per kilobase (FIG. 2d).

Example 2: A Rationally Engineered SpCas9 tracrRNA for Fixed Pair 3Cs-gRNAs

Figure 3:
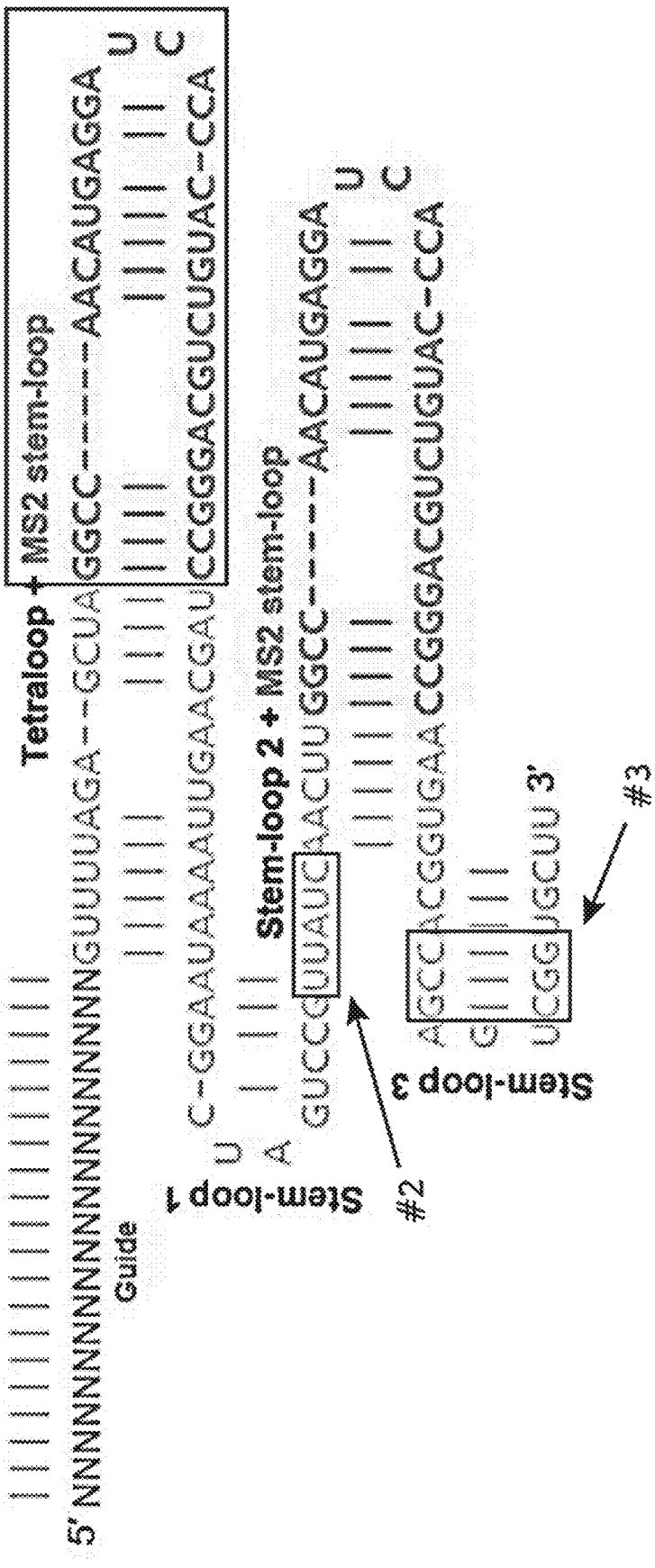
Figure 5:
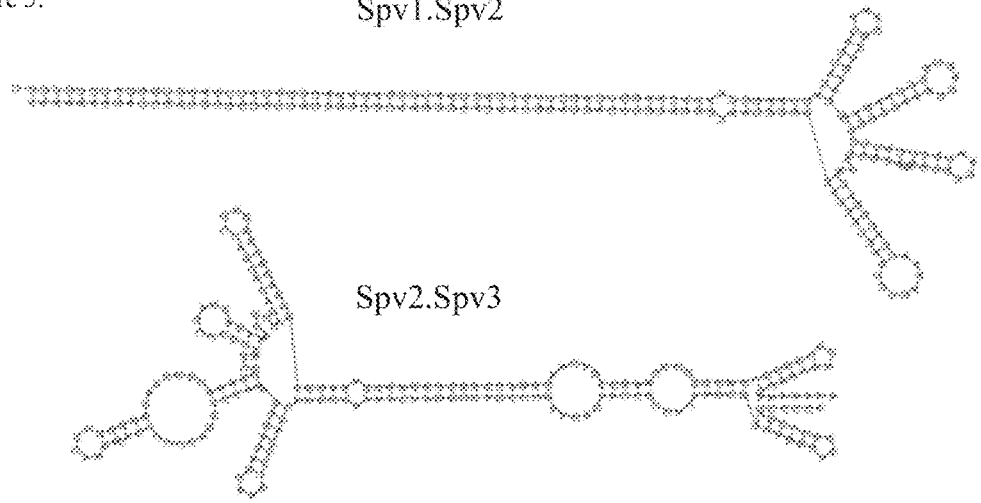
Figure 5:
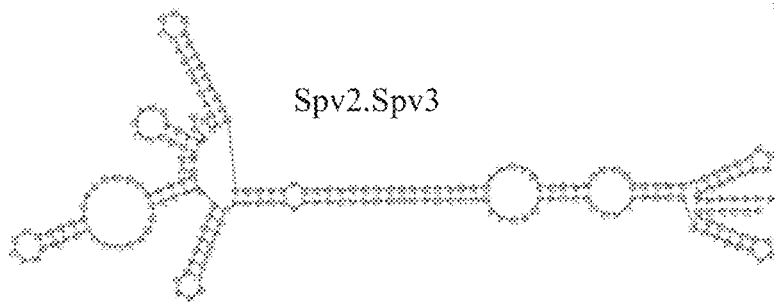
Figure 5:
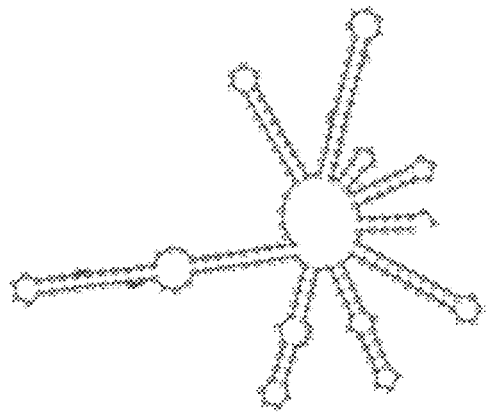
Figure 5:
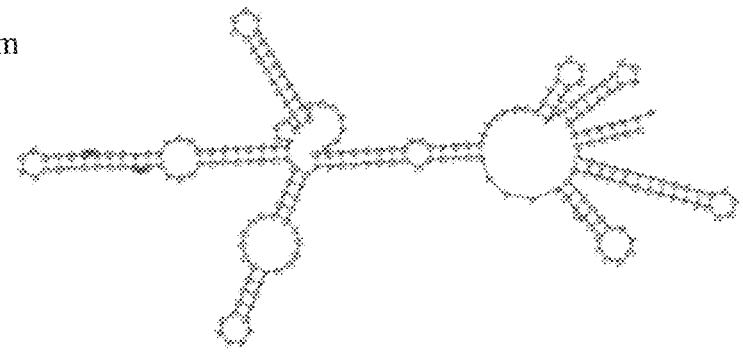
Figure 5:
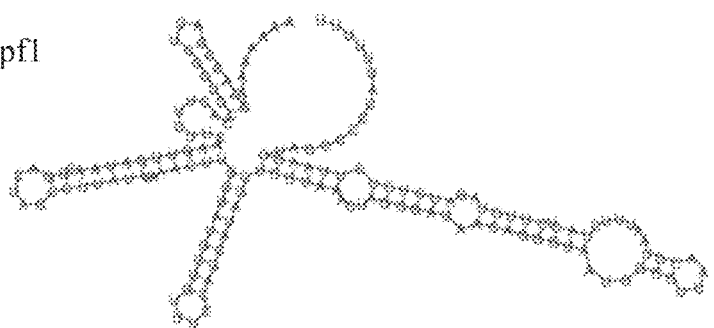
Figure 6:
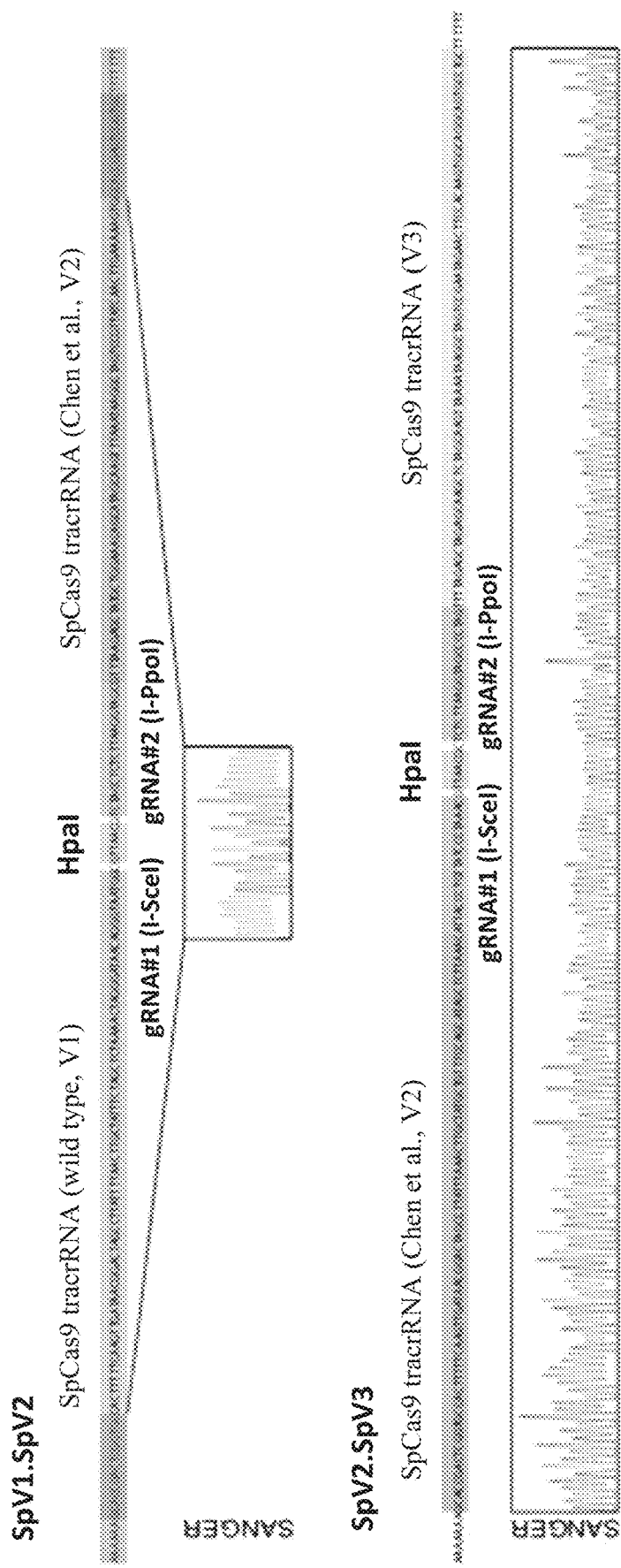
Figure 6:
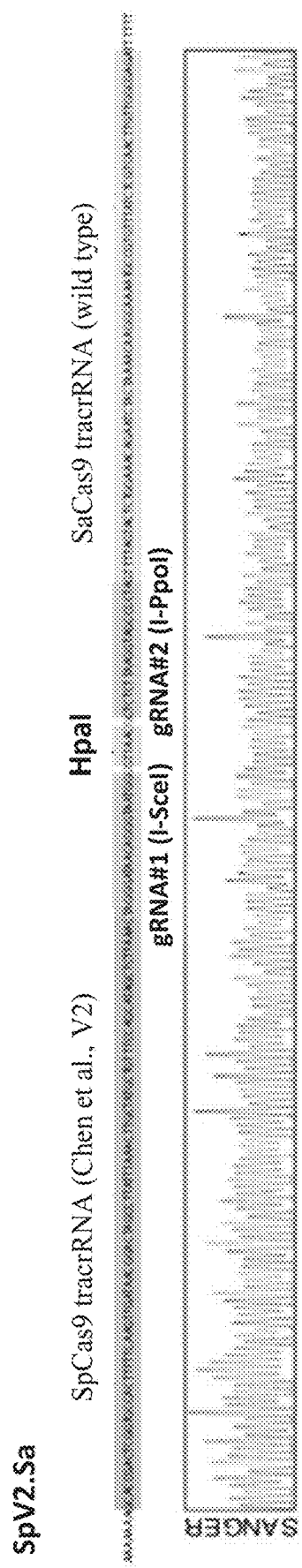
Figure 6:
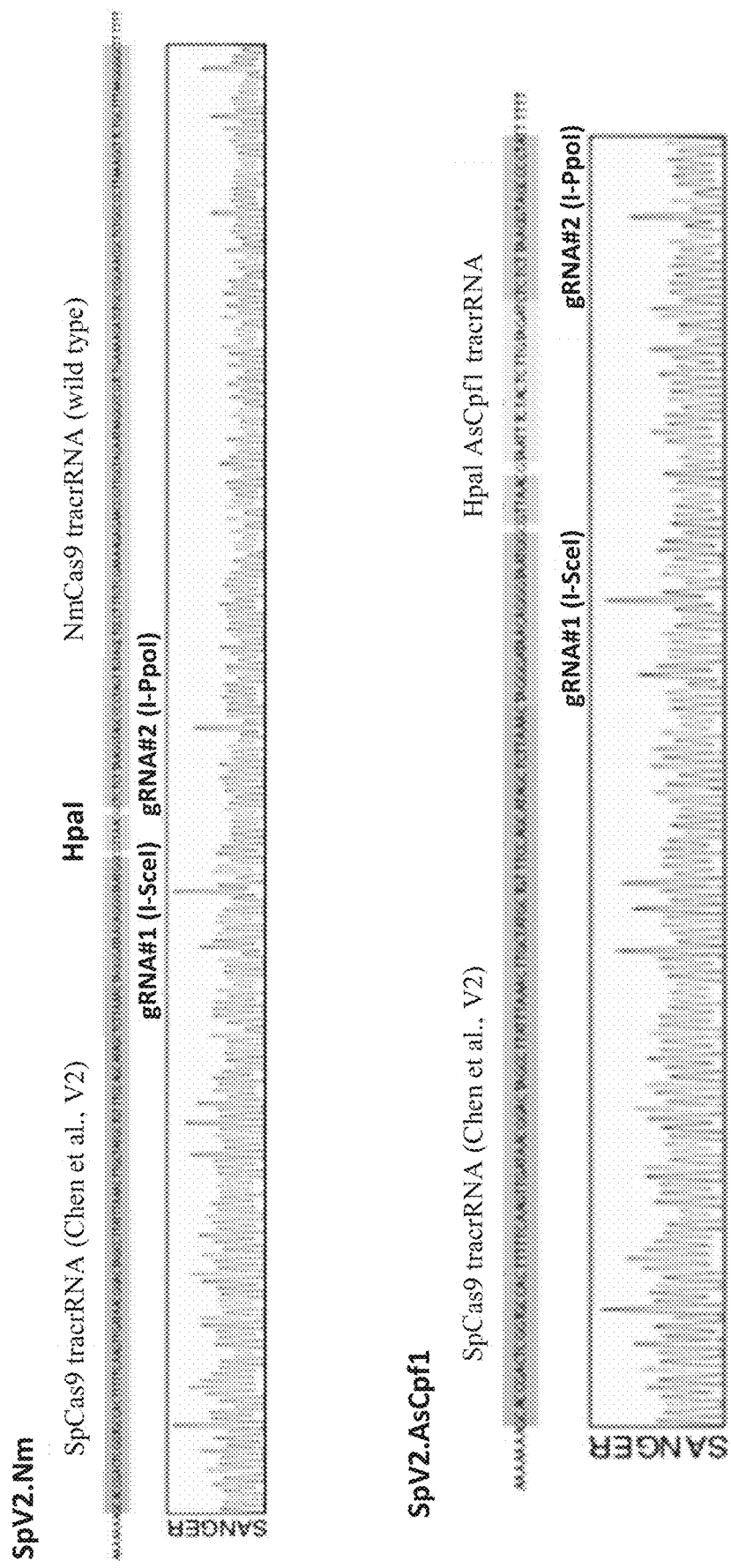

Plasmids containing highly homologous or identical nucleotide sequences have been demonstrated to recombine during viral packaging leading to the loss of sequence information and resulting in inactive viral particles[8-11]. To circumvent this issue during bacteriophage particle packaging, the inventors combined the wildtype SpCas9 tracrRNA (vi) sequence with the recently engineered and improved SpCas9 tracrRNA version 2 (v2) for the generation of fixed-pair template plasmid DNA (v1.v2) (FIG. 2a)[12]. Additionally, the inventors generated fixed-pair template plasmid DNA of extraverted tracrRNA-combinations of SpCas-SaCas9 (v2.Sa), SpCas9-NmCas9 (v2.Nm) and SpCas9-AsCpf1 (v2.As), all of which generated the expected DNA fragments when subjected to analytical restriction enzyme digests (FIG. 4a). Furthermore, the inventors predicted the folding of the extraverted tracrRNA and gRNA sequences by conventional bioinformatic tools and while most tracrRNA combinations did not result in strong folding[13], the inventors identified a strong homology-based folding of vi and v2 of SpCas9 tracrRNA molecules (FIG. 5). To prevent vi and v2 from recombination, the inventors rationally engineered a new SpCas9 tracrRNA sequence based on the previously reported crystal structure of SpCas9 in complex with tracrRNA and gRNA molecules[14]. The inventors identified three sequence regions that are not in direct contact with SpCas9 and therefore may contain engineering potential to break sequence homology (FIG. 3a). The inventors rationally changed the three sequences to nucleotides that would most effectively break the refolding of ssDNA and named the new tracrRNA molecule version three (v3) (FIG. 3b, 5). Similar to all other template plasmids, v2 combined with v3 (v2.v3) resulted in a correct digestive pattern after enzymatic restriction analysis (FIG. 4a). Next, the inventors tested the portfolio of fixed-pair template plasmids for the generation of circular ssDNA. Single stranded DNA from all fixed-pair template plasmids from multiple clones, including v1.v2 of SpCas9 tracrRNA combinations, resulted in high quality circular ssDNA that migrated as a single band when analyzed by gel-electrophoresis (FIG. 4b). However, the loss of highly homologous sequence information may not be visible by gel-electrophoresis of ssDNA. Therefore, the inventors used purified bacteriophage particles containing the fixed-pair template DNA to retransform XL1 bacteria for the generation of dsDNA based on the ssDNA delivered to them through phage infection. The resulting plasmid dsDNA was subjected to an analytic restriction enzyme digest to confirm the correctness of the fixed-pair template dsDNA. As predicted, dsDNA resulting from v1.v2 tracrRNA ssDNA was subject to severe recombination events, demonstrated by faster migrating bands, the lack of a correct digestive pattern and the absence of correct SANGER sequence information (FIG. 4c, 6). However, all other tracrRNA combinations, including the newly engineered v3 SpCas9 tracrRNA were free of DNA recombination and contained the correct nucleotide sequence, as determined by SANGER sequencing (FIG. 4c, 6). This demonstrates that circular ssDNA from the respective fixed-pair templates is of high quality and contains the correct homology sequences to enable 3Cs-DNA generation.

TracrRNA Designs

```
TracrRNA designs
grey highlight: modified from wt
underlined: MS2 stem loop
wt(v1) - 136.50 kcal/mol, 76bp,
                                    SEQ ID No: 8
GTTTTAGAGCTAGAAATAGCAAGTTAAAATAAGGCTAGTCCGTTATCAA
CTTGAAAAAGTGGCACCGAGTCGGTGC v2 - 167.90 kcal/mol, 86 bp,
                                    SEQ ID No: 9
GTTTAAGAGCTATGGGGGGGGGGGGGGTAGCAAGTTTAAATAAGGCTAG
TCCGTTATCAACTTGAAAAAGTGGCACCGAGTCGGTGC v3 (engineered) - 90.90 kcal/mol, 82bp,
                                    SEQ ID No: 9
GTTTTAGAGCTAGGGGGGGGGGGGGGTAGCAAGTTAAAATAAGGCTAGTCCG
GGGGGGAACTTCCACAAGTGGCAGGGAGTGGGGTGC
```

Example 3: Proof-of-Principle: Functionality of Sequentially Cloned Fixed-Pair gRNAs In order to test 3Cs fixed-pair gRNA performance, the inventors set out to design an experimental setting that would enable to selectively quantify a full DNA excision event over the occurrence of individual insertions or deletions (InDels) at the two gRNA target sites. To do so, the inventors designed two pairs of gRNAs each targeting the intronic region of the human retinoblastoma gene RB1 gene, whose depletion or inactivation results in resistance to the selective Cdk4/6 inhibitor Palbociclib. Both pairs were designed in such a way, that individual gRNAs are at least 50 nucleotides away from the 5' or 3' end of the closest coding exon of RB1. Pair 1 was designed to include exon 7, while pair 2 was designed to include exon 9 of RB1 (FIG. 7a). Of note, gRNAs are designed to target noncoding intronic DNA to minimize coding InDels. The two sets of paired gRNAs were individually and sequentially cloned by conventional cloning into the previously described lentiviral plasmid pKLV2.2[15]. Both plasmids were subject to the generation of infectious lentiviral particles that were subsequently used to transduce SpCas9-expressing RPE1 cells. One day after lentiviral transduction, cells were exposed to 1 µM of the selective Cdk4 inhibitor Palbociclib (PD) and their proliferation quantified by a daily AlamarBlue assay for a total duration of 11 days. In striking contrast to cells transduced with empty pKLV2.2-carrying lentiviral particles, cells transduced with pair 1 or pair 2 of RB1-targeting gRNA pairs displayed a sharp increase in proliferation after 4 to 7 days of Palbocilcib exposure (FIG. 7b).

This demonstrates that defined pairs of gRNAs are active and result in full DNA excision events including the exons flanked by gRNAs rather than small InDels at the individual sites. Therefore, fixed-pair of gRNAs have the potential to be suitable for large cellular functional screenings.

Example 4: Defined gRNA Combinations in Pooled Fixed-Pair 3Cs-Technology

In order to demonstrate 3Cs performance of the above described fixed-pair circular ssDNA templates, the inventors combined them with a DNA oligonucleotide composed of 1) 5' and 3' homology to the extraverted tracrRNA combinations and 2) bidirectional gRNA sequences targeting the two intronic regions flanking exon 7 of the RB1 gene (pair 1, FIG. 7a,b). When analyzing the 3Cs-DNA by gel-electrophoresis, the inventors were surprised to observe slower migrating DNA species in the 3Cs reaction performed on v1.v2 template DNA for which the inventors previously demonstrated recombination and the lack of tracrRNA sequences (FIG. 8). The inventors hypothesize that the slower migrating DNA results from the complete lack of oligonucleotide to template homology that may cause non-specific binding of the oligonucleotide and results in partial 3Cs-DNA products. However, regardless of the tracrRNA to tracrRNA combinations used, all other 3Cs reactions also resulted in slower migrating DNA species, indicating the generation of 3Cs-DNA in all tested conditions (FIG. 8).

To accurately quantify fixed-pair 3Cs reaction efficiency by pooled restriction enzyme digest and direct SANGER sequencing of single bacterial clones, the inventors transformed the resulting 3Cs-DNA into XL1 bacteria. In line with the previous observations, bacteria transformed with 3Cs-products resulting from the use of v1.v2 template ssDNA did not grow and no plasmid DNA could be extracted or analyzed. This confirmed the hypothesis that unspecific oligonucleotide to template DNA binding does not result in transformable 3Cs-DNA. In contrast, bacteria from all other tracrRNA combinations grew normally and their amplified DNA was extracted. Importantly, a successful 3Cs reaction will change the I-SceI restriction enzyme site in the 3Cs-template DNA to a defined gRNA sequence, thereby rendering I-SceI inactive on correctly generated 3Cs-DNA. Purified DNA of polyclonal over-night bacterial cultures was subsequently subject to analytical restriction enzyme digests and compared to the respective wildtype plasmid. Most importantly, all fixed-pair tracrRNA-combinations revealed an uncleaved plasmid DNA species when subject to I-SceI digest, indicating the presence of plasmid DNA in which the I-SceI restriction site has been changed (FIG. 9).

Figure 7:
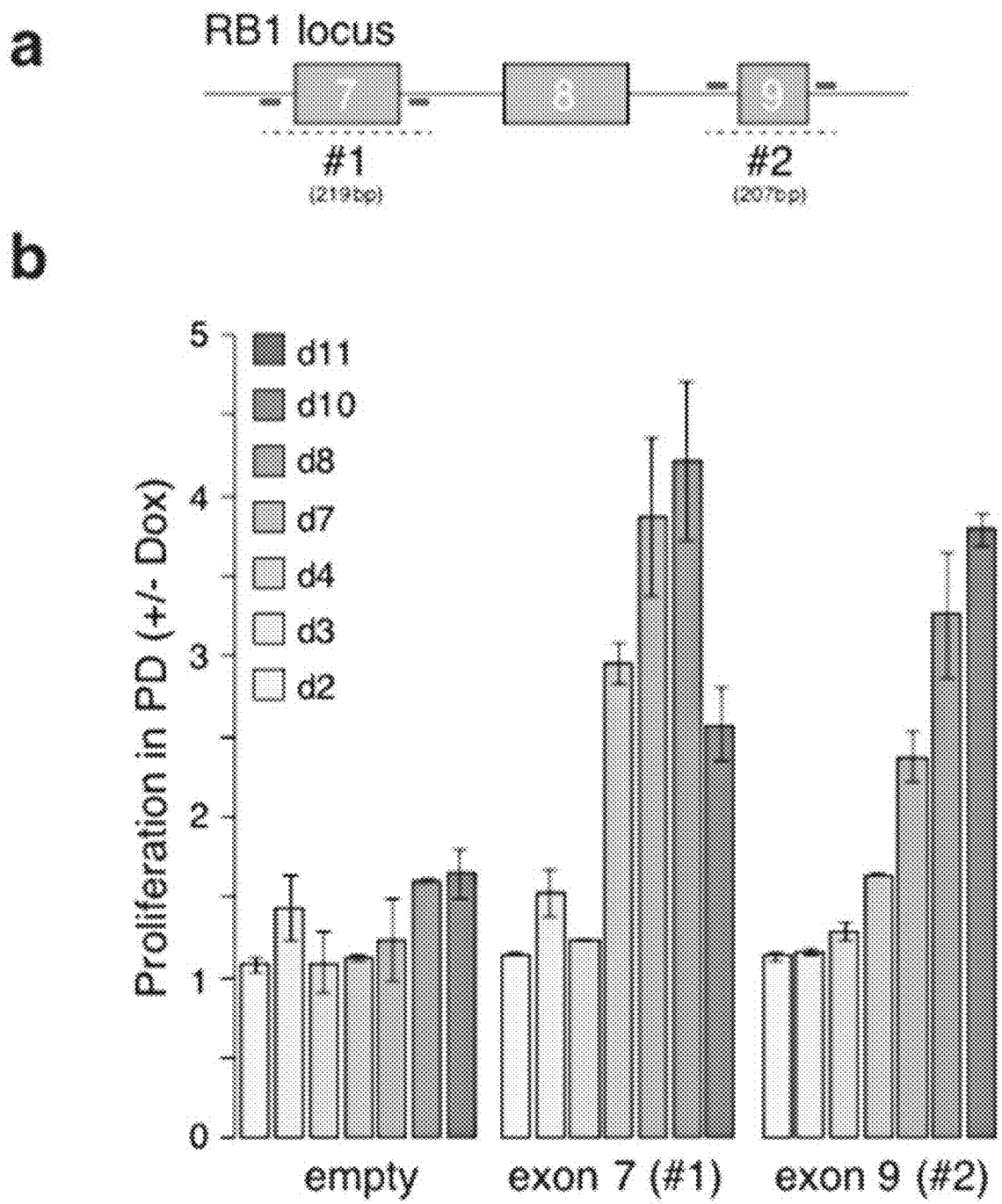
Figure 10:
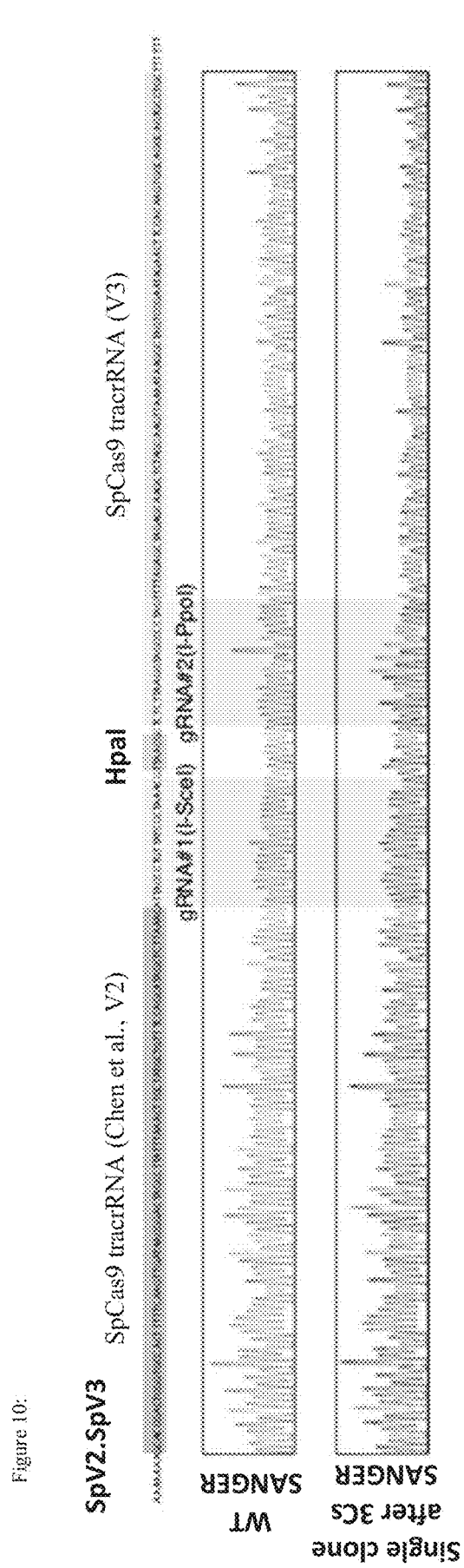
Figure 10:
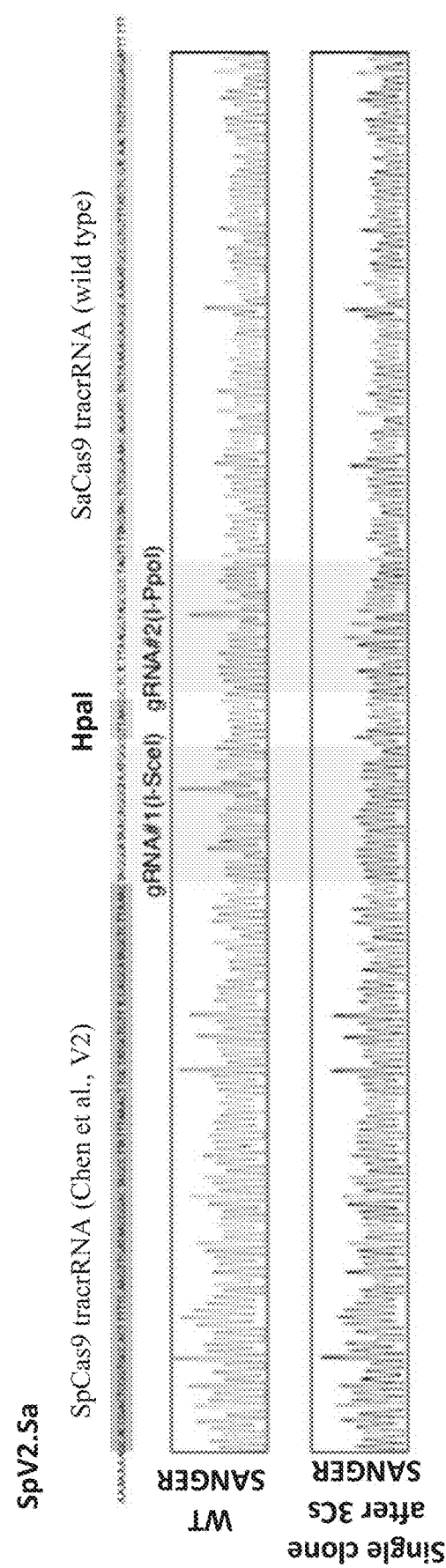
Figure 10:
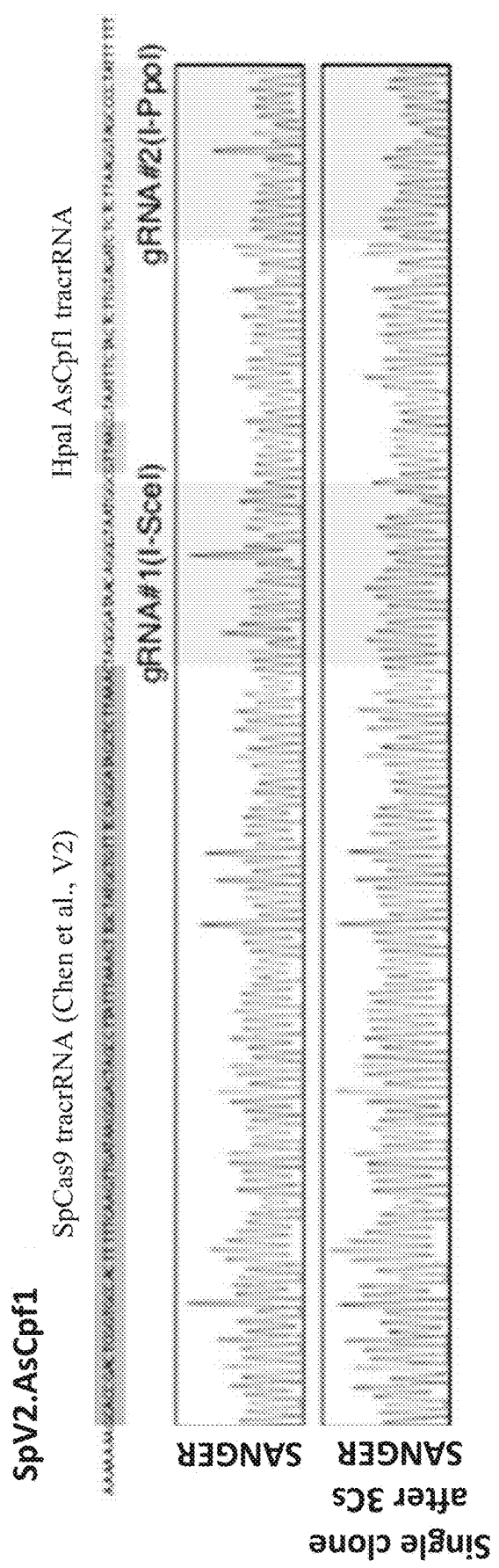

To confirm the I-SceI sequence change, the inventors analyzed single bacterial clones by SANGER sequencing and identified the two RB1 gRNA sequences corresponding to excision pair 1 of FIG. 7 (FIG. 10a-c).

In summary, the inventors have developed a novel method for the generation of defined combinations of CRISPR/Cas gRNAs, for the generation of pooled fixed-pair gRNA libraries. This innovative technology has the potential for a wide field of applications, including but not limited to improved on-target efficiency for the generation of gene knockouts, activation or inhibition or effector-mediated editing, as well as the precise excision of genetic information (CRISPRex). Fixed-pair gRNA reagents are of special importance for the fields of CRISPRa and CRISPRi, both of which have been demonstrated to significantly depend on multiple gRNAs for efficient activation (a) or inactivation (i). The inventors believe this technology has broad implications for investigations of coding and noncoding genetic information in health and disease.

Example 5: Expending the 3Cs Fixed-Pair gRNA Toolbox

The 3Cs fixed-pair technology enables further technological developments in the used gRNA combinations as shown by the following adaptations (FIG. 11).
1) 3Cs fixed-pair gRNAs can be combined with one single gRNA-expressing cassette to enable multiplexing of one single gRNA with fixed-pair gRNAs (FIG. 11a).
2) 3Cs fixed-pair gRNAs can be combined with two single gRNA-expressing cassettes to enable multiplexing of two single gRNAs with fixed-pair gRNAs (FIG. 11b).
3) A single 3Cs fixed-pair gRNA-expressing cassette can be multiplexed with a second 3Cs fixed-pair gRNA-expressing cassette to enable 3Cs fixed-pair gRNA multiplexing (FIG. 11c).

Example 6: Preventing 3Cs Library Amplification

To ensure that 3Cs reagents cannot be amplified by third second/parties, final 3Cs reagents can be linearized by restriction enzyme digest to remove essential parts of the plasmid/library that prevents growth/amplification in bacteria. The transfection of linearized plasmid/library, however, is active in generating lentiviral particles for experimental purposes.

Bacterial plasmid amplification requires antibiotic drug selection/pressure to ensure the selective outgrowth of bacteria carrying the desired plasmid/library. As such, e.g. 1) the antibiotic promoter can be excised, 2) the entire or parts of the antibiotic drug resistance gene can be removed, or 3) the origin-of-replication (ORI) sequence can be excised.

Example 7: Cloning-Free Enhanced 3Cs Fixed-Pair gRNA Generation

3Cs reagents benefit from the lack of PCR amplification and conventional cloning steps. However, the integration of the bidirectional promoter to complete 3Cs fixed-pair reagent production potentially interferes with the overall quality (diversity and distribution) of 3Cs fixed-pair reagents. Therefore, the inventors designed an enhanced 3Cs fixed-pair protocol completely avoiding the need for any conventional cloning steps. To do so, the inventors took advantage of the fact that the non-engineered type II CRISPR system of *Streptococcus pyogenes* uses two separate RNA molecules (crRNA and tracrRNA) that intracellularly form, together with Cas9, a functional RNA-guided DNA nuclease complex (FIG. 12a).

By modifying the 3Cs fixed-pair template plasmid to contain two bidirectionally located (towards another) human RNA promoter (7SK and U6) sequences that are separated by two placeholder gRNA sequences that are further separated by bidirectional crRNA sequences that anneal to the tracrRNA, the 3Cs fixed-pair reaction would be sufficient to produce fixed-pair compositions of crRNAs from the same plasmid (enhanced plasmid #3.1) (FIG. 12b, c). A separate SpCas9 tracrRNA-expressing cassette on the same plasmid ensures expression of both RNA molecules within the same cell. In contrast to previous designs, 3Cs fixed-pair oligonucleotides for enhanced plasmid #3.1 contains three regions of homology (3Cs fixed-pair homology), potentially improving oligonucleotide annealing and thereby performance in 3Cs reactions (FIG. 12d).

Example 8: Producing Enhanced 3Cs Fixed-Pair Reagents

To demonstrate performance and robustness of the enhanced 3Cs fixed-pair template, the inventors transformed plasmid #3.1 into CJ236 bacteria and selected two clones for ssDNA generation. Agarose gel-electrophoresis identified a single band of ssDNA for the CJ236 clones, demonstrating robust ssDNA generation of plasmid #3.1 (FIG. 13a).

To identify robustness and quality of 3Cs reactions on plasmids #3.1, the inventors designed 5 oligonucleotides, encoding for combinations of control (non-human-target, NHT), mCherry, GFP targeting gRNAs, and performed individual 3Cs fixed-pair reactions. All designed oligonucleotides performed well in 3Cs fixed-pair reactions, revealed by the expected band pattern visualized by agarose gel-electrophoresis (FIG. 13b). Since single oligonucleotide 3Cs fixed-pair synthesis performed well, the inventors asked if pooled primer reactions are possible with this protocol. To identify this, the inventors designed a single oligonucleotide containing 8 randomized nucleotide positions (8N primer), with a calculated diversity of 65,536 and performed the in vitro 3Cs reaction. Reaction products were purified, electroporated and amplified in bacteria before a first quality controls step (P1) removed wildtype remnants by applying enzymes Pad and I-SceI. Non-cleaved products of P1 were again electroporated and a second quality control step (P2) was applied to identify the degree of wildtype remnants in the final 8N library preparation by agarose gel-electrophoresis (FIG. 13c, d). As expected, both quality control steps removed wildtype remnants to below the detection limit. To visualize the randomized nucleotides and potentially identify any unwanted mutations juxtaposed to the 3Cs primer homology regions, the inventors performed SANGER sequencing on the level of P1 and P2 on the pooled 8N plasmids. Surprisingly, already at the level of P1, all 8 randomized nucleotides could be identified by SANGER sequencing and quality step P1 had only little effect on the overall degree of nucleotide randomization (FIG. 13e). This suggests that the 8N 3Cs fixed-pair reaction was very efficient, potentially due to the long intra-oligonucleotide 3Cs homology, and demonstrates that 3Cs fixed-pair plasmid #3.1 is very well suited for the generation of pooled libraries of gRNAs with predefined combinations.

The inventors previously demonstrated that the ratio of ssDNA to 3Cs oligonucleotide is critical for robust 3Cs performance. Hence, the inventors tested which ratio is most efficient for 3Cs fixed-pair reactions. To do so, the inventors set up 3 reactions with ratios of 600/20 (1:33), 600/15 (1:25), and 400/20 (1:50) (ng of ssDNA to µg of oligonucleotide), and 2 reactions with a ration 1:33 for which the total amount of ssDNA was adjusted to be either 10 or 5 µg. All reaction products were electroporated and amplified as described earlier and processed by quality control step P1. Interestingly, the inventors were unable to observe any notable difference in 3Cs performance in all tested conditions (FIG. 14a). While a precise ratio of ssDNA to oligonucleotide in single or multiplexed 3Cs reactions is important, the additional internal 3Cs homology of fixed-pair primers may circumvent this need and broadens the performing ratios of ssDNA to oligonucleotide.

Example 9: Cellular Functionality of Enhanced 3Cs Fixed-Pair Reagents

To demonstrate functionality of the enhanced 3Cs fixed-pair plasmid and reagents, the inventors took the above generated NHT and GFP targeting constructs and made infectious lentiviral particles of them. GFP-expressing hTERT-RPE1 cells were transduced with them for 48 hours, after which a selection pressure (puromycin) for another 4 days was applied before the cells where analyzed by FACS and immunoblotting for which wildtype (wt) and GFP-positive cells (GFP) served as controls. Importantly, the fixed-pair combination of two NHT-gRNA sequences did not influence the percentage of GFP-positive cells, while both NHT-GFP2 and GFP2-NHT induced a strong reduction of GFP-positive cells by FACS. However, the combination of GFP2-GFP1 (two different GFP-targeting gRNAs) reduced the GFP-positive cell population to below the detection limit (FIG. 15a, b). In addition, GFP deletion efficiency was confirmed by immunoblotting of GFP, confirming the FACS finding (FIG. 15b). Fluorescent proteins expressed in human cells reflect an artificial situation, the inventors therefore asked if endogenously expressed genes in RPE1 cells would similarly be depleted more efficiently by two gRNAs. To address this question, RPE1 cells were transduced with fixed-pair gRNA constructs encoding for NHT/NHT, NHT/Cdk2, Cdk2/NHT, or Cdk2/Cdk2. As expected, endogenous Cdk2 was more efficiently depleted by two fixed-pair gRNAs than by either single gRNA (FIG. 15c). This demonstrates that 3Cs fixed-pair reagents are functional in cells and that a 3Cs fixed-pair gRNA combinations that target the same gene has enhanced on-target activity over a single gRNA.

Material and Methods
dU-DNA Template Amplification and Purification

KCM competent and dut⁻/ung⁻ *Escherichia coli* cells (*E. coli* strain K12 CJ236, NEB) were transformed with 50 ng of CRISPR/Cas template plasmid according to the following protocol: DNA was mixed with 2 µL of 5×KCM solution (1M KCl, 1M CaCl$_2$, 1M MgCl$_2$) set to 10 µL and chilled on ice for 10 minutes. An equal volume of CJ236 bacteria was added to the DNA/KCM mixture, gently mixed and incubated on ice for 15 minutes. The bacteria/DNA mixture was then incubated at room temperature for 10 minutes, and subsequently inoculated in 200 µL SOC media. The bacteria were incubated at 37° C. and 200 rpm for 1 hour. After 1 hour, bacteria were selected with ampicillin on LB-agar plates and incubated over-night at 37° C.

The next morning, a single colony of transformed CJ236 was picked into 1 mL of 2YT media supplemented with M13KO7 helper phage to a final concentration of 1×10$^8$ pfu, optional 6.25 µg/ml uridine, chloramphenicol (final concentration 35 µg/mL) and ampicillin (final concentration 100 µg/mL) to maintain host F' episome and phagemid, respectively. After 2 hours of shaking at 200 rpm and 37° C., kanamycin (final concentration 25 µg/mL) was added to select for bacteria that have been infected with M13KO7. Bacteria were kept at 200 rpm and 37° C. for additional 6 hours before the culture was transferred to 30 mL of 2YT media supplemented with ampicillin (final concentration 100 µg/mL) and kanamycin (final concentration 25 µg/mL). After 20 hours of shaking at 200 rpm and 37° C., the bacterial culture was centrifuged for 10 minutes at 10,000 rpm and 4° C. in a Beckman JA-12 fixed angle rotor. To precipitate phage particles, the supernatant was transferred to 6 mL (⅕ of culture volume) PEG/NaCl (20% polyethylene glycol 8000, 2.5 M NaCl), incubated for 1 hour at RT and subsequently centrifuged for 10 minutes at 10,000 rpm and 4° C. in a Beckman JA-12 fixed angle rotor. The phage pellet was resuspended in 1 mL PBS.

Circular ssDNA was purified from the resuspended phages using the E.Z.N.A. M13 DNA Mini Kit (Omega) according to the manufacturer's protocol.

Generating 3Cs-DNA

Oligonucleotides that were used for 3Cs-reactions are listed separately. For each 3Cs reaction, 600 ng of oligonucleotides were phosphorylated by mixing 2 µL 10× TM buffer (0.1 M MgCl$_2$, 0.5 M Tris-HCl, pH 7.5), 2 µL 10 mM ATP, 1 µL 100 mM DTT, 20 units of T4 polynucleotide kinase and H$_2$O in a total volume of 20 µL. The mixture was incubated for 1 h at 37° C.

Annealing of the phosphorylated oligonucleotides with the circular dU-ssDNA template was performed by adding the 20 µL phosphorylation product to 25 µL 10× TM buffer, 20 µg of dU-ssDNA template, and H$_2$O to a total volume of 250 µL. The mixture was incubated for 3 min at 90° C., 5 min at 50° C. and 5 min at room temperature.

3Cs-DNA was generated by adding 10 µL of 10 mM ATP, 10 µL of 100 mM dNTP mix, 15 µL of 100 mM DTT, 2000 ligation units (or 30 Weiss units) of T4 DNA ligase and 30 units of T7 DNA polymerase to the annealed oligonucleotide/ssDNA mixture. The 3Cs-synthesis mix was incubated for 12 hours (over-night) at room temperature, affinity purified and desalted through gel extraction columns (Thermo Fisher Scientific). The 3Cs-reaction product was analyzed by gel electrophoresis alongside the ssDNA template on a 0.8% TAE/agarose gel (100 V, 30 min).

Cell Culture

As standard, HEK293T (ATCC CRL-3216) were maintained in Dulbecco's Modified Eagle's Medium (DMEM, Thermo Fisher Scientific) and hTERT-RPE1 (CRL-4000) in DMEM: Nutrient Mixture F-12 (DMEM/F12, Thermo Fisher Scientific), supplemented with 10% fetal bovine serum (FBS) and 1% penicillin-streptomycin (Sigma) at 37° C. with 5% CO$_2$.

Lentiviral Transduction

RPE1 cells were seeded at an appropriate density for each experiment with a maximal confluency of 60-70% in DMEM/F12 (Thermo Fisher Scientific), supplemented with 10% FBS and 1% penicillin-ptreptomycin (Sigma). At the day of transduction, polybrene was added to the media to a final concentration of 8 µg/mL, as well as viral supernatant according to the previously determined viral titer. The next morning, the media was replaced with fresh media and the cells were subjected to antibiotic selection or experimental analysis.

Generation and Quantification of Lentiviral Particles

The day before transfection, HEK293T cells were seeded to 5×10$^5$ cells/mL. To transfect HEK293T cells, transfection medium containing 1/10 of culture volume Optimem (Thermo Fisher Scientific), 105 µl/ml lipofectamin 2000 (Invitrogen), 1.65 µg transfer vector, 1.35 µg pPAX2 (addgene plasmid #12260) and 0.5 µg pMD2.G (addgene plasmid #12259). The mixture was incubated for 30 minutes at room temperature before adding it drop-wise to the medium. The next morning, transfection media was replaced with fresh media to generate transfection reagent-free lentiviral supernatant. Lentiviral supernatant was harvested at 24 h and 48 h, pooled and stored at −80° C.

To determine the lentiviral titer, RPE1 cells were plated in a 24 well plate with 20,000 cells per well. The following day, cells were transduced using 8 µg/ml polybrene and a series of 0.5, 1, 5 and 10 µL of viral supernatant. After 3 days of incubation at 37° C., the percentage of fluorescence-positive cells was determined by flow cytometry. The following formula was used to calculate the viral titer:

$$\text{Virus titer (transducing units/mL)} = \frac{20.000 \text{ target cells} \times \frac{\text{of GFP positive cells}}{100}}{\text{volume of supernatant (mL)}}.$$

Flow Cytometry

All samples were analyzed on a FACSCanto II flow cytometer (BD Biosciences), and data were processed by FlowJo software (FlowJo, LLC). Gating was carried out on the basis of viable and single cells that were identified on the basis of their scatter morphology.

Immunoblotting

Preparation of lysates and immunoblot analyses were performed as described previously using Tris lysis buffer (50 mM Tris-HCl (pH 7.8), 150 mM NaCl, 1% IGEPAL CA-630) containing 20 mM NaF, 20 mM β-glycerophosphate, 0.3 mM Na-vanadate, 20 µg/ml RNase A, 20 µg/ml DNase and 1/300 protease inhibitor cocktail (Sigma-Aldrich, P8340) and phosphatase inhibitor cocktail #2 (Sigma-Aldrich, P5726). The antibodies used in this study were purchased from the following sources: mouse anti-GFP (GFP (B-2): sc-9996, 1:2,000, Santa Cruz Biotechnology, Inc.), mouse anti-Tubulin (clone 12G10, 1:1,000, Developmental Studies Hybridoma Bank, University of Iowa), mouse anti-Cdk2 (clone M2 (sc-163), 1:1,000, Santa Cruz Biotechnology, Inc.). Secondary antibodies used for western blot analysis were goat anti-mouse (Thermo Scientific, 31430) and goat anti-rabbit (Thermo Scientific, 31460). The mouse anti-Tubulin hybridoma cell line (clone #12G10) was developed by J. Frankel and E. M. Nelson under the auspices of the NICHD and maintained by the Developmental Studies Hybridoma Bank. Protein levels were visualized with Pierce ECL Western Blotting Substrate on a BioRad ChemiDoc MP imaging system and analyzed with Bio-Rad Image Lab software (version 4.1 build 16).

DNA oligonucleotides used
First strategy:
Double Underline: 3'-homology to tracrRNA sequence
Curved Underline: 5'-homology to tracrRNA sequence
italic: homology to restriction enzyme site sequence
underlined: gRNA-encoding sequence (PAM specific)
bold: AsCpf1 tracrRNA sequence -continued SpV1-SpV2-R: (3Cs synthesis oligonucleotide)
SEQ ID NO: 1
5'-GTTTCCAGCATAGCTCTTAAACCCGTCCTCGAAGTTCATCAC*CGTTAACG*GTCGCCCTCGAACTTCACCTGTTTTAGAGCTAGAAATAGCAA-3'

SpV2-SpV3-R: (3Cs synthesis oligonucleotide)
SEQ ID NO: 2
5'-CTTGCTCTAGCTCTAAAACTTGCGATTTTCTCTCATACAA*CGTTAACG*GCTGAATGAGAAAGTAAAAGTTTAAGAGCTATGCTGG-3'

SpV2-SaV1-R: (3Cs synthesis oligonucleotide)
SEQ ID NO: 3
5'-CTGTTTCCAGAGTACTAAAACTGCGATTTTCTCTCATACAA*CGTTAACG*GCTGAATGAGAAAGTAAAAGTTTAAGAGCTATGCTGG-3'

SpV2-NmV1-R: (3Cs synthesis oligonucleotide)
SEQ ID NO: 4
5'-AGAAAGGGAGCTACAACATGGACTTTGCCCATAAGTA*CGTTAACG*GCTGAATGAGAAAGTAAAAGTTTAAGAGCTATGCTGG-3'

SpV2-As-R: (3Cs synthesis oligonucleotide)
SEQ ID NO: 5
5'-TTCGACCGACAATTAAAAAAGCAACTGCTGAATGAGAAACATCTACAAGAGTAGAAATTA*CGTTAAC*GGCTGAATGAGAAAGTAAAAGGTTTAAGAGCTATGCTGG-3' pLKO-1-Seq-F: (SANGER sequencing oligonucleotide)
SEQ ID NO: 6
5'-ATTCATAATGATAGTAGGAGGCTTGGTAGG-3'

Enhanced strategy:
Dot-dashed underline: 3'-homology to h7SK sequence
Dashed underline: 5'-homology to hU6 sequence
Dotted Underline: intramolecular-homology to crRNA
underlined: gRNA-encoding sequence (PAM specific)

NHT-NHT (3Cs synthesis oligonucleotide)
SEQ ID NO: 11
GAAAGGACGAAACACCGTCAGGATCAGGGTGTATGGCgttttagagctatgcTTTTTTAAAAAAgcatagctctaaaacCTCGCACCCATATAGCAAGCCgaggtacccaagcg GFP2-NHT (3Cs synthesis oligonucleotide)
SEQ ID NO: 12
GAAAGGACGAAACACCGTCAGGATCAGGGTGTATGGCgttttagagctatgcTTTTTTAAAAAAgcatagctctaaaacCGATGTTGTGGCGGATCTTGCgaggtacccaagcg NHT-GFP2 (3Cs synthesis oligonucleotide)
SEQ ID NO: 13
GAAAGGACGAAACACCGGAAGGGCATCGACTTCAAGGgttttagagctatgcTTTTTTAAAAAAgcatagctctaaaacGCATGTTGTGGCGGATCTTGCgaggtacccaagcg GFP1-GFP2 (3Cs synthesis oligonucleotide)
SEQ ID NO: 14
GAAAGGACGAAACACCGGAAGGGCATCGACTTCAAGGgttttagagctatgcTTTTTTAAAAAAgcatagctctaaaacCGATGTTGTGGCGGATCTTGCgaggtacccaagcg NHT-Cdk2 (3Cs synthesis oligonucleotide)
SEQ ID NO: 15
GAAAGGACGAAACACCGAAGCAGAGAGATCTCTCGGAGTTTAGAGACGCTCGTCTCTAAACCCATCAGGCGGAAGCTTTTTTCGAGGTACCCAAGCG Cdc27-NHT (3Cs synthesis oligonucleotide)
SEQ ID NO: 16
GAAAGGACGAAACACCGAAAAAGCTTCCGCCTGATGGGTTTAGAGACGCTCGTCTCTAAACAGATGCGGTTTTCCTCGCAGCCGAGGTACCCAAGCG -continued Cdc27-Cdk2 (3Cs synthesis oligonucleotide)

SEQ ID NO: 17

GAAAGGACGAAACACCGACAGGTTGCCAGTAAAAACA
GTTTAGAGACGCTCGTCTCTAAACCTCCCGTCAACTTGTTTC
TGCGAGGTACCCAAGCG

REFERENCES

1. Kim, H. K. et al. In vivo high-throughput profiling of CRISPR-Cpf1 activity. *Nat Methods* (2016). doi:10.1038/nmeth.4104
2. Han, K. et al. Synergistic drug combinations for cancer identified in a CRISPR screen for pairwise genetic interactions. *Nat. Biotechnol.* 35, 463-474 (2017).
3. Mali, P. et al. RNA-guided human genome engineering via Cas9. *Science (80-.).* 339, 823-826 (2013).
4. Cong, L. et al. Multiplex genome engineering using CRISPR/Cas systems. *Science (80-.).* 339, 819-823 (2013).
5. Ran, F. A. et al. In vivo genome editing using *Staphylococcus aureus* Cas9. *Nature* 520, 186-191 (2015).
6. Kleinstiver, B. P. et al. Genome-wide specificities of CRISPR-Cas Cpf1 nucleases in human cells. *Nat Biotechnol* (2016). doi:10.1038/nbt.3620
7. Hou, Z. et al. Efficient genome engineering in human pluripotent stem cells using Cas9 from *Neisseria meningitidis*. *Proc. Natl. Acad. Sci.* 110, 15644-15649 (2013).
8. Kuate, S., Marino, M. P. & Reiser, J. Analysis of Partial Recombinants in Lentiviral Vector Preparations. *Hum. Gene Ther. Methods* 25, 126-135 (2014).
9. Sack, L. M., Davoli, T., Xu, Q., Li, M. Z. & Elledge, S. J. Sources of Error in Mammalian Genetic Screens. G3& #58; *Genes|Genomes|Genetics* 6, 2781-2790 (2016).
10. Miller, A. D. & Buttimore, C. Redesign of retrovirus packaging cell lines to avoid recombination leading to helper virus production. *Mol. Cell. Biol.* 6, 2895-902 (1986).
11. Barlett, M. M., Erickson, M. J. & Meyer, R. J. Recombination between directly repeated origins of conjugative transfer cloned in M13 bacteriophage DNA models ligation of the transferred plasmid strand. *Nucleic Acids Res.* 18, 3579-86 (1990).
12. Chen, B. et al. Dynamic Imaging of Genomic Loci in Living Human Cells by an Optimized CRISPR/Cas System. *Cell* 155, 1479-1491 (2013).
13. Lorenz, R. et al. ViennaRNA Package 2.0. *Algorithms Mol. Biol.* 6, 26 (2011).
14. Konermann, S. et al. Genome-scale transcriptional activation by an engineered CRISPR-Cas9 complex. *Nature* 517, 583-588 (2015).
15. Tzelepis, K. et al. A CRISPR Dropout Screen Identifies Genetic Vulnerabilities and Therapeutic Targets in Acute Myeloid Leukemia. *Cell Rep* 17, 1193-1205 (2016).
16. Chen, B. et al. Dynamic imaging of genomic loci in living human cells by an optimized CRISPR/Cas system. *Cell* 155, 1479-1491 (2013).

The invention claimed is:

1. A method for generating a covalently closed circularized (ccc) DNA vector for expressing a fixed pair of guide RNAs (gRNAs) comprising the steps of:
   (a) Providing an enhanced recipient vector comprising:
      (x) two inverted or extraverted enhanced gRNA expression cassettes, wherein each enhanced gRNA expression cassette comprises in that order: (i) optionally an RNA promoter, (ii) a gRNA placeholder sequence, and (iii) optionally a crRNA sequence; and
      (y) a tracrRNA expression cassette;
   (b) Providing an enhanced mutagenic DNA primer comprising two gRNA coding sequences of interest and homology regions capable to mediate a binding of the mutagenic DNA primer to the two inverted or extraverted enhanced gRNA expression cassettes; and
   (c) Generating a cccDNA vector using the recipient vector and the mutagenic DNA primer.

2. The method according to claim 1, wherein each of the gRNA coding sequences is at least 10 nucleotides to 200 nucleotides long, more preferably 10 to 50, more preferably 10 to 30, more preferably 15 to 30, more preferably 15 to 25, most preferably 17 to 23, and even more preferably about 20 nucleotides long.

3. The method according to claim 1, wherein the method is used to generate a covalently closed circularized (ccc) DNA based guide RNA expression vector or vector library, wherein each vector comprises a defined combination of at least two different gRNAs.

4. The method according to claim 1, wherein the enhanced mutagenic DNA primer provided in step (b) comprises in this order:
   i. a first homology region capable of binding to the first enhanced gRNA expression cassette,
   ii. a first predetermined gRNA sequence to be expressed,
   iii. a linker sequence,
   iv. a second predetermined gRNA sequence to be expressed, and
   v. a second homology region capable of binding to the second gRNA expression cassette,
   and wherein the method further comprises the step:
   (d) introducing into the linker sequence of the cccDNA vector a promoter fragment comprising two extraverted RNA promoter sequences to obtain the cccDNA vector for expressing a fixed pair of guide RNAs.

5. The method according to claim 4, wherein in step (a) the enhanced recipient vector comprises two gRNA placeholder sequences, and wherein the two gRNA placeholder sequences are separated by a linker, and wherein the linker sequence is identical to the linker sequence in the enhanced mutagenic DNA primer as provided in step (b).

6. The method according to claim 4, wherein the linker sequence comprises a restriction enzyme recognition site, such as a restriction enzyme recognition site for blunt ligation, or restriction enzyme recognition site for sticky end ligation.

7. The method according to claim 4, wherein in step (c) the cccDNA vector is generated by following the steps of:

(a') Providing the recipient vector as single stranded (ss) phagemid vector,
(b') Annealing the mutagenic DNA primer to said ss phagemid vector,
(c') Amplifying a covalently closed circularized (ccc)-heteroduplex dsDNA therefrom, and
(d') Removing residual wild type phagemid vector DNA.

8. The method according to claim 4, wherein in step (d) the promoter fragment is introduced into the linker sequence by inducing a double strand break in the linker sequence, for example using a restriction enzyme, ligating said promoter element into the so induced double strand break.

9. The method according to claim 4, wherein the tracrRNA expression cassette of one of the at least two enhanced gRNA expression cassettes is not identical to the tracrRNA expression cassette of the other of the at least two enhanced gRNA expression cassettes.

10. The method according to claim 9, wherein the tracrRNA expression cassette of the one and the other enhanced gRNA expression cassettes are characterized in that their sequence homology is between 50 and 95%, and/or wherein the tracrRNA expression cassettes have the ability of binding to the same or different RNA/DNA or genome editing nuclease.

\* \* \* \* \*

SEQUENCE LISTING

```
<160> NUMBER OF SEQ ID NOS: 17

<210> SEQ ID NO 1
<211> LENGTH: 92
<212> TYPE: DNA
<213> ORGANISM: Artificial
<220> FEATURE:
<223> OTHER INFORMATION: mutagenic oligonucleotide

<400> SEQUENCE: 1
gtttccagca tagctcttaa acccgtcctc gaagttcatc accgttaacg gtcgccctcg      60
aacttcacct gttttagagc tagaaatagc aa                                    92

<210> SEQ ID NO 2
<211> LENGTH: 85
<212> TYPE: DNA
<213> ORGANISM: Artificial
<220> FEATURE:
<223> OTHER INFORMATION: mutagenic oligonucleotide

<400> SEQUENCE: 2
cttgctctag ctctaaaact gcgatttct ctcatacaac gttaacggct gaatgagaaa       60
gtaaaaggtt taagagctat gctgg                                            85

<210> SEQ ID NO 3
<211> LENGTH: 87
<212> TYPE: DNA
<213> ORGANISM: Artificial
<220> FEATURE:
<223> OTHER INFORMATION: mutagenic oligonucleotide

<400> SEQUENCE: 3
ctgtttccag agtactaaaa ctgcgatttt ctctcataca acgttaacgg ctgaatgaga      60
```

```
aagtaaaagg tttaagagct atgctgg                                         87

<210> SEQ ID NO 4
<211> LENGTH: 83
<212> TYPE: DNA
<213> ORGANISM: Artificial
<220> FEATURE:
<223> OTHER INFORMATION: mutagenic oligonucleotide

<400> SEQUENCE: 4
agaaagggag ctacaacatg gactttgccc ataagtacgt taacggctga atgagaaagt     60
aaaaggttta agagctatgc tgg                                             83

<210> SEQ ID NO 5
<211> LENGTH: 106
<212> TYPE: DNA
<213> ORGANISM: Artificial
<220> FEATURE:
<223> OTHER INFORMATION: mutagenic oligonucleotide

<400> SEQUENCE: 5
ttcgaccgac aattaaaaaa gcaactgctg aatgagaaag atctacaaga gtagaaatta     60
cgttaacggc tgaatgagaa agtaaaaggt ttaagagcta tgctgg                    106

<210> SEQ ID NO 6
<211> LENGTH: 30
<212> TYPE: DNA
<213> ORGANISM: Artificial
<220> FEATURE:
<223> OTHER INFORMATION: mutagenic oligonucleotide

<400> SEQUENCE: 6
attcataatg atagtaggag gcttggtagg                                      30

<210> SEQ ID NO 7
<211> LENGTH: 98
<212> TYPE: RNA
<213> ORGANISM: Artificial
<220> FEATURE:
<223> OTHER INFORMATION: tracrRNA
<220> FEATURE:
<221> NAME/KEY: misc_feature
<222> LOCATION: (1)..(20)
<223> OTHER INFORMATION: n is a, c, g, or u

<400> SEQUENCE: 7
nnnnnnnnnn nnnnnnnnnn guuuuagagc uagaaauagc aaguuaaaau aaggcuaguc     60
cguuaucaac uugaaaaagu ggcaccgagu cggugcuu                             98

<210> SEQ ID NO 8
<211> LENGTH: 76
<212> TYPE: DNA
<213> ORGANISM: Artificial
<220> FEATURE:
<223> OTHER INFORMATION: tracrRNA

<400> SEQUENCE: 8
gttttagagc tagaaatagc aagttaaaat aaggctagtc cgttatcaac ttgaaaaagt     60
ggcaccgagt cggtgc                                                     76

<210> SEQ ID NO 9
<211> LENGTH: 86
<212> TYPE: DNA
<213> ORGANISM: Artificial
```

```
<220> FEATURE:
<223> OTHER INFORMATION: tracrRNA

<400> SEQUENCE: 9
gttttagagc taggctggaa acagcatagc aagtttaaat aaggctagtc cgttatcaac      60
ttgaaaaagt ggcaccgagt cggtgc                                           86

<210> SEQ ID NO 10
<211> LENGTH: 82
<212> TYPE: DNA
<213> ORGANISM: Artificial
<220> FEATURE:
<223> OTHER INFORMATION: tracrRNA

<400> SEQUENCE: 10
gttttagagc tagagcaagc tctagcaagt taaaataagg ctagtccgaa tagaacttcc      60
acaagtggca ggcagtgcct gc                                               82

<210> SEQ ID NO 11
<211> LENGTH: 114
<212> TYPE: DNA
<213> ORGANISM: Artificial
<220> FEATURE:
<223> OTHER INFORMATION: mutagenic oligonucleotide

<400> SEQUENCE: 11
gaaaggacga acaccgtca ggatcagggt gtatggcgtt ttagagctat gcttttttaa      60
aaaagcatag ctctaaaacc tcgcacccat atagcaagcc gaggtaccca agcg          114

<210> SEQ ID NO 12
<211> LENGTH: 114
<212> TYPE: DNA
<213> ORGANISM: Artificial
<220> FEATURE:
<223> OTHER INFORMATION: mutagenic oligonucleotide

<400> SEQUENCE: 12
gaaaggacga acaccgtca ggatcagggt gtatggcgtt ttagagctat gcttttttaa      60
aaaagcatag ctctaaaacc gatgttgtgg cggatcttgc gaggtaccca agcg          114

<210> SEQ ID NO 13
<211> LENGTH: 114
<212> TYPE: DNA
<213> ORGANISM: Artificial
<220> FEATURE:
<223> OTHER INFORMATION: mutagenic oligonucleotide

<400> SEQUENCE: 13
gaaaggacga acaccggaa gggcatcgac ttcaagggtt ttagagctat gcttttttaa      60
aaaagcatag ctctaaaacg catgttgtgg cggatcttgc gaggtaccca agcg          114

<210> SEQ ID NO 14
<211> LENGTH: 114
<212> TYPE: DNA
<213> ORGANISM: Artificial
<220> FEATURE:
<223> OTHER INFORMATION: mutagenic oligonucleotide

<400> SEQUENCE: 14
gaaaggacga acaccggaa gggcatcgac ttcaagggtt ttagagctat gcttttttaa      60
aaaagcatag ctctaaaacc gatgttgtgg cggatcttgc gaggtaccca agcg          114
```

```
<210> SEQ ID NO 15
<211> LENGTH: 96
<212> TYPE: DNA
<213> ORGANISM: Artificial
<220> FEATURE:
<223> OTHER INFORMATION: mutagenic oligonucleotide

<400> SEQUENCE: 15
gaaaggacga aacaccgaag cagagagatc tctcggagtt tagagacgct cgtctctaaa      60
cccatcaggc ggaagctttt tcgaggtacc caagcg                                96

<210> SEQ ID NO 16
<211> LENGTH: 96
<212> TYPE: DNA
<213> ORGANISM: Artificial
<220> FEATURE:
<223> OTHER INFORMATION: mutagenic oligonucleotide

<400> SEQUENCE: 16
gaaaggacga aacaccgaaa aagcttccgc ctgatgggtt tagagacgct cgtctctaaa      60
cagatgcggt tttcctcgca gcgaggtacc caagcg                                96

<210> SEQ ID NO 17
<211> LENGTH: 96
<212> TYPE: DNA
<213> ORGANISM: Artificial
<220> FEATURE:
<223> OTHER INFORMATION: mutagenic oligonucleotide

<400> SEQUENCE: 17
gaaaggacga aacaccgaca ggttgccagt aaaaacagtt tagagacgct cgtctctaaa      60
cctcccgtca acttgtttct gcgaggtacc caagcg                                96
```